(12) United States Patent
Denby et al.

(10) Patent No.: US 10,717,972 B2
(45) Date of Patent: Jul. 21, 2020

(54) MONOTERPENE-PRODUCING GENETICALLY MODIFIED HOST CELLS AND METHODS OF USE OF SAME

(71) Applicant: The Regents of the University of California, Oakland, CA (US)

(72) Inventors: Charles M. Denby, Berkeley, CA (US); Jay D. Keasling, Berkeley, CA (US); James Kirby, Berkeley, CA (US); Rachel Alexandra Li, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 22 days.

(21) Appl. No.: 15/777,037

(22) PCT Filed: Dec. 9, 2016

(86) PCT No.: PCT/US2016/065944
§ 371 (c)(1),
(2) Date: May 17, 2018

(87) PCT Pub. No.: WO2017/100655
PCT Pub. Date: Jun. 15, 2017

(65) Prior Publication Data
US 2018/0327733 A1 Nov. 15, 2018

Related U.S. Application Data

(60) Provisional application No. 62/312,368, filed on Mar. 23, 2016, provisional application No. 62/265,943, filed on Dec. 10, 2015.

(51) Int. Cl.
| | |
|---|---|
| *C12N 9/88* | (2006.01) |
| *C12P 5/00* | (2006.01) |
| *C12N 9/04* | (2006.01) |
| *C12C 11/00* | (2006.01) |
| *C12N 9/16* | (2006.01) |
| *C12P 7/04* | (2006.01) |
| *C12N 9/10* | (2006.01) |

(52) U.S. Cl.
CPC ............ *C12N 9/88* (2013.01); *C12C 11/003* (2013.01); *C12N 9/0006* (2013.01); *C12N 9/1085* (2013.01); *C12N 9/16* (2013.01); *C12P 5/007* (2013.01); *C12P 7/04* (2013.01); *C12Y 101/01034* (2013.01); *C12Y 205/0101* (2013.01); *C12Y 301/07011* (2015.07); *C12Y 402/03025* (2013.01)

(58) Field of Classification Search
None
See application file for complete search history.

(56) References Cited

U.S. PATENT DOCUMENTS

| | | | | |
|---|---|---|---|---|
| 8,257,957 | B2 * | 9/2012 | Keasling | C12N 9/88 |
| | | | | 435/252.33 |
| 9,809,829 | B2 * | 11/2017 | Keasling | C12N 9/1085 |
| 2004/0023395 | A1 | 2/2004 | Kim et al. | |
| 2004/0063182 | A1 | 4/2004 | Ohto et al. | |
| 2010/0209969 | A1 | 8/2010 | Pichersky et al. | |
| 2015/0087042 | A1 | 3/2015 | Keasling et al. | |
| 2015/0259705 | A1 | 9/2015 | Huembelin et al. | |

FOREIGN PATENT DOCUMENTS

| | | |
|---|---|---|
| WO | WO 2011/123576 | 10/2011 |
| WO | 2016/0098883 | * 7/2015 |

OTHER PUBLICATIONS

Crowell et al. (Molecular cloning and characterization of a new linalool synthase, Archives of Biochemistry and Biophysics 405 (2002) 112-121).*
Ignea, et al.; "Engineering monoterpene production in yeast using a synthetic dominant negative geranyl diphosphate synthase"; ACS Synthetic Biology; vol. 3, No. 5, pp. 298-306 (May 16, 2014).
UniProtKB Asscession No. Q8H2B4 (LLOS_MENAQ) "R-linalool synthase, chloroplastic" Mar. 1, 2003 [found online Mar. 30, 2017 at http://www.uniprot.org/uniprot/Q8H2B4].

* cited by examiner

*Primary Examiner* — Manjunath N Rao
*Assistant Examiner* — Jae W Lee
(74) *Attorney, Agent, or Firm* — Bozicevic Field & Francis, LLP; Paula A. Borden

(57) ABSTRACT

The present disclosure provides a genetically modified host cell capable of producing linalool (or 3,7-dimethylocta-1,6-dien-3-ol).

17 Claims, 39 Drawing Sheets
Specification includes a Sequence Listing.

FIG. 2A

| | |
|---|---|
| C. breweri | MQLITNESSSSSELQFLVDKVKRESLSSSSNTQNLFLSTSPYDTAWLALIPHPHHHHHGRPMFEKCLQWLLHNQTPQGFWAAAGDNISDTDDD |
| A. polygama | MASFHRFCVSSLLVPNNSPQISNAYRAPAVPSMPTTQKWSITEDLAFTSNPSKQHNHQTGYRTFSDEFYVKREKLLKDVRRALREVEETPLEGLV |
| F. x ananassa | MPVHATPAAESQIISKPEVVKRTANFKPSVWGDRFANYAEDITQTQMQEQVELKQVRKEVFTNAADDSSHQLKLIIDETQRLGVAYHFESEID |
| P. frutescens | MSSMRIYVAIMKKPSVKHVDNVDKKASKPSWRMSSATAGLRASSSLQDVKKFADEITARRSGNYQPSLMDFNYLQPLNTTHYKEERHLKREA |
| M. citrata | MCTIISVNHHHVALLSKPKVKLFHTKNKRSASINLPWSLSPSSSAASRPICSTISSKLYTISSAQEERRSGNYHPSVWDFDTQSLDTDHYKEE |
| L. esculentum | MVSILSNIGMMVVTFKRPSLFTSLRRRSANNIITKHSHPISTIRRSGNYKPTMWDFQFTQSLHNPYEGDKYMKRLNKLKKEVKKMMTVEGSHD |

FIG. 2B

| | |
|---|---|
| C. jambhiri | MSSSINPSTLVTSVNGFKCLPLTTNKAAIRMAKNKPLQCLVSAKYDNLTVERSANYQPSIWDHFLQSLNSKYTDEAYKRAEGLKGKVKIAT |
| O. europaea | MDCTMTSISLFSQSSNGISGTARSPFQWPINHRFSSGQRDFICKSLPVSSPSATPLIFAENGAMYNIRQPVIVTPEVDDGTKHSELVERIRREL |
| P. frutescens | MSSISQKVIGLNKAANNLQNLDRRGEKTRCVSSSKAASCLRASCSLQDVKPVQEGRRSGNYQPSIWDFNYVQSLNTFYKEERYLNTRHAELL |
| P. dulcis | MASARSTISLSSQSSHHGFSKNSFPWQLRHSRFVMGSRARTCACMSSSVSLPTATTSSSVITGNDALLKYIRQPMVIPLKEKEGTKRREYLLEKT |
| V. vinifera | MSRFVTMPSHVLPSSFVAPSLQVSSSPCSWRTRPSPCTSCHLSPSSSSKPLLGSHDYSLLKSLTTLSPHAVNSEADSSTRRMKEVKERTWEAFYRA |
| O. basilicum | MSCARITVTLPYRSAKTSIQRGITHYPALIRPRFSACTPLASAMPLSSTPLINGDNSQRKNTRCHMEESSSKRREVLLEETTRKLQRNDTESVEK |

FIG. 4

*Actinidia polygama* linalool synthase

GenBank ADD81295

```
  1 masfhrfcvs sllvpnnspq isnayrapav psmpttqkws itedlafisn pskqhnhqtc
 61 yrtfsdefyv krekklkdvr ralreveetp leglvmidtl qrlgidyhfq geigallqkq
121 qrkskcdype hdlfevstrf rllrqeghnv padvfnhfrd kkgrfksels rdirglmsly
181 easqlsigge dildqaadfs sqllsgwatn pdhhqarlvr nalthpyhks latftarnfh
241 ydckgqngwv nnlqelakmd ltvvqsmhqk evlqvsqwwk drglanelkl vrnqplkwym
301 wpmaaltdpr fseerveltk pisfiyiidd ifdvygtlee ltlftdavnr weltaveqlp
361 dymkvcfkal yditneiayk iykkhgwnpi dslrrmwasl cnaflveakw fasghlpkae
421 eylkngiiss gmhvvtvhmf fllggcftde svnlvdehag itssiatilr lsddlgsakd
481 edqdgydgsy veyylkdhkg ssvenareev irmisdawkr lneeclspnp fsatfrkgcl
541 niarmvplmy syddnhnlpl leehmkamly dsss
```

FIG. 5

*Mentha aquatica (Mentha citrata)* linalool synthase

GenBank AAL99381

```
  1 mctiisvnhh hvailskpkv klfhtknkrs asinlpwsls psssaasrpi scsissklyt
 61 issaqeetrr sgnyhpsvwd fdfiqsldtd hykeekqler eeelimevkk llgakmeatk
121 qleliddlqn lglsyffrde iknilnsiyk ifqnnnstkv gdlhftslgf rllrqhgfnv
181 sqgvfdcfkn ehgsdfektl igedtkgvlq lyeasfllre gedtlevark fstefleekl
241 kagidqdnls ssighsleip lhwriqrlee rwfldaysrr kdmnpiifel akldfniiqa
301 tqqeelkdls rwwndsslpq klpfvrdrlv esyywalglf eahkfgyerk taakiitlit
361 alddvydiyg tldelqlfth virrwdtesa tqlpyylqlf yfvlynfvse vayhilkeeg
421 fisipflhra wvdlvegylq eakwyytkyt ptmeeylnya sitigapavi sqiyfmlaks
481 kekpviesfy eydeiirlsg mlvrlpddlg tlpfemkrgd vaksiqiymk eqnatreeae
541 ehvrfmirea wkemnttmaa nsdlrgdvvm aaanlgrdaq fmyldgdgnh sqlqhrianl
601 lfkpyv
```

FIG. 6A

Nucleotide sequence encoding modified *Mentha citrata* linalool synthase

T67 M.c. Linalool Synthase
atgactagaagatccggtaattatcacccatctgtttgggatttcgacttcatccaatctttggata
ccgaccactacaaagaagaaaagcaattggaaagagaagaagaattgatcatggaagtcaaa
aagttgttgggtgctaaaatggaagctaccaaacaattggaattgatcgacgacttgcaaaactt
gggtttgtcttacttcttcagggacgaaatcaagaacatcttgaactccatctacaagatcttccaa
aacaacaactctaccaaggttggtgacttgcattttacatctttgggtttcagattattgagacaaca
cggtttcaacgtttcccaaggtgttttgattgcttcaagaacgaacacggttccgattttgaaaa
gaccttgattggtgaagataccaagggtgtcttgcaattatacgaagcttcattcttgttgagaga
aggtgaagatactttggaagttgccagaaagttctctaccgaattcttagaagaaaagttgaagg
ccggtatcgacggtgataacttatcttcttctatcggtcactccttggaaattccattgcattggag
aattcaaagattagaagaaagatggttcttggacgcctactctagaagaaaggatatgaaccca
atcatcttcgaattggccaagttggatttcaacattattcaagccacacaacaagaagaattgaa
ggacttgtctagatggtggaatgattcttccttgccacaaaaattgccattcgttagagatagattg
gtcgaatcttattactgggccttgggtttatttgaagctcataagtttggttacgaaagaaagaccg
ctgccaagattattactttgattaccgctttggatgacgtctacgatatctatggtactttggacga
attacaattattcacccacgtcatcagaagatgggatactgaatctgctactcaattgccttactact
tgcaattattctacttcgtcttgtacaatttcgtcagtgaagttgcctaccatatcttgaaagaaga
aggtttcatctccatcccattcttgcatagagcatgggttgatttggttgaaggttacttgcaagaa
gctaaatggtactacactaagtacactccaaccatggaagaatacttgaactacgcttctattacc
attggtgctccagctgttatttcccaaatctactttatgttggctaagtccaaagaaaagccagtca
tcgaatctttctacgaatacgacgaaattatcagattgtccggtatgttggttagattgccagatga
tttgggtactttgccttcgaaatgaagagaggtgacgttgctaagtctattcaaatctacatgaag
gaacaaaacgccaccagagaagaagcagaagaacacgttagattcatgattagagaagcct
ggaaagaaatgaacactactatggctgctaactccgatttgagaggtgatgtagttatggctgca
gctaatttgggtagagatgctcaattcatgtacttggatggtgatggtaaccactctcaattgcaa
catagaattgccaacttgttgttcaagccatacgtctaa

FIG. 6B modified *Mentha citrata* linalool synthase

```
MTRRSGNYHP SVWDFDFIQS LDTDHYKEEK QLEREEELIM EVKKLLGAKM EATKQLELID
DLQNLGLSYF FRDEIKNILN SIYKIFQNNN STKVGDLHFT SLGFRLLRQH GFNVSQGVFD
CFKNEHGSDF EKTLIGEDTK GVLQLYEASF LLREGEDTLE VARKFSTEFL EEKLKAGIDG
DNLSSSIGHS LEIPLHWRIQ RLEERWFLDA YSRRKDMNPI IFELAKLDFN IIQATQQEEL
KDLSRWWNDS SLPQKLPFVR DRLVESYYWA LGLFEAHKFG YERKTAAKII TLITALDDVY
DIYGTLDELQ LFTHVIRRWD TESATQLPYY LQLFYFVLYN FVSEVAYHIL KEEGFISIPF
LHRAWVDLVE GYLQEAKWYY TKYTPTMEEY LNYASITIGA PAVISQIYFM LAKSKEKPVI
ESFYEYDEII RLSGMLVRLP DDLGTLPFEM KRGDVAKSIQ IYMKEQNATR EEAEEHVRFM
IREAWKEMNT TMAANSDLRG DVVMAAANLG RDAQFMYLDG DGNHSQLQHR IANLLFKPYV
```

FIG. 7

*Thymus vulgaris* linalool synthase

GenBank AGS42396

```
  1 msatisvlhh atilpkpand vvlcknkras ninpwtpsls isskldtknp gtvkdrrrsg
 61 nyrpalwdfs yiqslnthdh ynkevrrgel ivevkkllge eigavkqlel iddlknlgls
121 yffqeeirnv lgsiyaehkf frnnqvegsk dlyftalgfr llreagfnis qevfdrfkne
181 egsgfeerlg edtkgmlqly easfllrege dtlelarqis teflkekldg teisdgnlss
241 sirhsleipl hwriqrlear wfldayaark dmnplifela kldfnniqat qqqelkdlsr
301 wwknlslpvk lpfvrdrlve syfwavglfe phkfgyqrki aakiitlits lddvydiygt
361 ldelqlftda irrwdtksan qlpyylqlfy falytfvsev aydilkeeeg fftiphlqra
421 wvdlvegylq eakwyhanyt psmeeylnta tvtigapavi sqvhfvlaks nekaeslhey
481 eeiirlsqkl vrlpddlgtl pfemkrgdva ksiqiymkeh gasreeaeeh vryeireawk
541 emntlmaaks alrdddlamv vanlgrdaqf myldgdgnhs hlqhqiqnll fhpyp
```

FIG. 8

*Perilla frutescens* linalool synthase

GenBank AAL38029

```
  1 myslriyvai mkkpsakhvd nvdkkaskps wrvslsssag lrassslqld vkkpaddeil
 61 tarrsgnyqp slwdfnylqs lnttqykevr hlkreaelie qvkmlleeem eavqqlelvd
121 dlknlglsyf fedqikqilt fiynehkcfh snsiieaeei rdlyftalgf rllrqhgfqv
181 sqevfdcfkn eegsdfkarl gddtkglIql yeasfllreg edtlelarqy atkflqkkvd
241 heliddnnll swilhsleip lhwriqrlea rwfldryatr rdmnqiilel akldfniiqa
301 tqqeelkdls rwwkstclae klpfvrdrlv esyfwaialf ephqygyhrk vaakiitlit
361 slddvydiyg tldelqlftd aiqrwdtesi srlpyymqlf ymvlynfvse laydglkekg
421 fitipylqrs wadlveaylk eakwfyngyv psmeeylnna yisigatpvi sqvfftlats
481 idkpvidsly eyhrilrlsg mlvrlpddlg tspfemkrgd vpkaiqlymk ernateieaq
541 ehvrflirea wkemntvtta adcpftddlv aatrnlgraa qfmyldgdgn hsqlhqriac
601 llfepya
```

FIG. 9

*Solanum lysopersicum* linalool synthase

GenBank NP_001233805

```
  1 mvsilsnigm mvvtfkrpsl ftslrrrsan niiitkhshp isttrrsgny kptmwdfqfi
 61 qslhnpyegd kymkrlnklk kevkkmmmtv egshdeelek lelidnlerl qvsyhfkdei
121 mqimrsinin iniappdsly ttalkfrllr qhgfhisqdi lndfkdengn lkqsickdtk
181 dilnsskdeh dnlkqstcnn tkgllklyea sflsienesf lrnttkstla hlmryvdqnr
241 cgeednmive lvvhalelpr hwmvprletr wyisiyerms nanplllela kldfnivqat
301 hqqdlrilsr wwkntglaek lpfsrdilve nmfwavgalf epqhsyfrrl itkvivfisi
361 iddiydvygt ldelelftla iqrwdtkame qlpdymkvcy laliniinev ayevlknhdi
421 nvlpyltksw adlcksylqe akwyhngykp nleeymdnar isigvpmvlv hslflvtnqi
481 tkealdsltn ypdiirwsat ifrlnddlgt ssdelkrgdv sksiqcymne kgaseeeaie
541 hiefliqetw eamntaqskn splsetfiev aknitkashf mylhsdvkss iskilfepii
601 isnvafalk
```

FIG. 10

*Perilla citriodora* linalool synthase

GenBank AHY39266

```
  1 mssiriyval mkkpsvkhvd nvdkkasksss wrvsssaglr assssqldvk kpadeiltar
 61 rsgnyqpslw dfnylrslnt thykeerhlk reaelieqvk mlldeemeav qqlelvddlk
121 nlqlsyffed qikqiltfiy nehecfrsnv eaeerdlyft algfrllrqh slqvsqevfd
181 cfkneegsdf kaslgddtkg lvqlyeasfl lregedtlel arqyatkflq kkvdhelidd
241 dnnllswirh sleiplhwri qrlearwfld ayamrhdvnp iilelakldf niiqatqqee
301 lkdlsrwwns tclaeklpfv rdrlvesyfw aialfephqf gyhrkiaaki itlitslddv
361 ydiygtldel qlftdaiqrw dtesisrlpy ymqlfymvly nfiselaydg lkekgfitip
421 ylqrswadlv eaylkeakwf yngytpsmee ylnnayisig atpvisqvff tlatsidkpv
481 ieslyeyhri lrlsgmlvrl pddlgtssfe mrrgdvpkai elymkernat eieaqehvrf
541 lireawkemn tattvadcpf tddlvaaaan lgraaqfmyl dgdgnhsqlh qriasllfeq
601 ya
```

FIG. 11

Truncated HMGR coding sequence

ATGGTTTTAACCAATAAAACAGTCATTTCTGGATCGAAAGTCAAAAGTTTATCA
TCTGCGCAATCGAGCTCATCAGGACCTTCATCATCTAGTGAGGAAGATGATTC
CCGCGATATTGAAAGCTTGGATAAGAAAATACGTCCTTTAGAAGAATTAGAAGC
ATTATTAAGTAGTGGAAATACAAAACAATTGAAGAACAAAGAGGTCGCTGCCT
TGGTTATTCACGGTAAGTTACCTTTGTACGCTTTGGAGAAAAAATTAGGTGATA
CTACGAGAGCGGTTGCGGTACGTAGGAAGGCTCTTTCAATTTTGGCAGAAGCT
CCTGTATTAGCATCTGATCGTTTACCATATAAAAATTATGACTACGACCGCGTA
TTTGGCGCTTGTTGTGAAAATGTTATAGGTTACATGCCTTTGCCCGTTGGTGT
TATAGGCCCCTTGGTTATCGATGGTACATCTTATCATATACCAATGGCAACTAC
AGAGGGTTGTTTGGTAGCTTCTGCCATGCGTGGCTGTAAGGCAATCAATGCTG
GCGGTGGTGCAACAACTGTTTTAACTAAGGATGGTATGACAAGAGGCCCAGTAG
TCCGTTTCCCAACTTTGAAAAGATCTGGTGCCTGTAAGATATGGTTAGACTCA
GAAGAGGGACAAAACGCAATTAAAAAAGCTTTTAACTCTACATCAAGATTTGCA
CGTCTGCAACATATTCAAACTTGTCTAGCAGGAGATTTACTCTTCATGAGATT
TAGAACAACTACTGGTGACGCAATGGGTATGAATATGATTTCTAAAGGTGTCGA
ATACTCATTAAAGCAAATGGTAGAAGAGTATGGCTGGGAAGATATGGAGGTTG
TCTCCGTTTCTGGTAACTACTGTACCGACAAAAAACCAGCTGCCATCAACTGGA
TCGAAGGTCGTGGTAAGAGTGTCGTCGCAGAAGCTACTATTCCTGGTGATGTT
GTCAGAAAAGTGTTAAAAAGTGATGTTTCCGCATTGGTTGAGTTGAACATTGCT
AAGAATTTGGTTGGATCTGCAATGGCTGGGTCTGTTGGTGGATTTAACGCACA
TGCAGCTAATTTAGTGACAGCTGTTTCTTGGCATTAGGACAAGATCCTGCACA
AAATGTTGAAAGTTCCAACTGTATAACATTGATGAAAGAAGTGGACGGTGATT
TGAGAATTTCCGTATCCATGCCATCCATCGAAGTAGGTACCATCGGTGGTGGTA
CTGTTCTAGAACCACAAGGTGCCATGTTGGACTTATTAGGTGTAAGAGGCCCG
CATGCTACCGCTCCTGGTACCAACGCACGTCAATTAGCAAGAATAGTTGCCTGT
GCCGTCTTGGCAGGTGAATTATCCTTATGTGCTGCCCTAGCAGCCGGCCATTT
GGTTCAAAGTCATATGACCCACAACAGGAAACCTGCTGAACCAACAAAACCTAA
CAATTTGGACGCCACTGATATAAATCGTTTGAAAGATGGGTCCGTCACCTGCA
TTAAATCCTAA

FIG. 12

Truncated 3-hydroxy-3-methylglutaryl-coenzyme A reductase (HMGR)

```
Met Val Leu Thr Asn Lys Thr Val Ile Ser Gly Ser Lys Val Lys Ser
Leu Ser Ser Ala Gln Ser Ser Ser Ser Gly Pro Ser Ser Ser Ser Glu
Glu Asp Asp Ser Arg Asp Ile Glu Ser Leu Asp Lys Lys Ile Arg Pro
Leu Glu Glu Leu Glu Ala Leu Leu Ser Ser Gly Asn Thr Lys Gln Leu
Lys Asn Lys Glu Val Ala Ala Leu Val Ile His Gly Lys Leu Pro Leu
Tyr Ala Leu Glu Lys Lys Leu Gly Asp Thr Thr Arg Ala Val Ala Val
Arg Arg Lys Ala Leu Ser Ile Leu Ala Glu Ala Pro Val Leu Ala Ser
Asp Arg Leu Pro Tyr Lys Asn Tyr Asp Tyr Asp Arg Val Phe Gly Ala
Cys Cys Glu Asn Val Ile Gly Tyr Met Pro Leu Pro Val Gly Val Ile
Gly Pro Leu Val Ile Asp Gly Thr Ser Tyr His Ile Pro Met Ala Thr
Thr Glu Gly Cys Leu Val Ala Ser Ala Met Arg Gly Cys Lys Ala Ile
Asn Ala Gly Gly Gly Ala Thr Thr Val Leu Thr Lys Asp Gly Met Thr
Arg Gly Pro Val Val Arg Phe Pro Thr Leu Lys Arg Ser Gly Ala Cys
Lys Ile Trp Leu Asp Ser Glu Glu Gly Gln Asn Ala Ile Lys Lys Ala
Phe Asn Ser Thr Ser Arg Phe Ala Arg Leu Gln His Ile Gln Thr Cys
Leu Ala Gly Asp Leu Leu Phe Met Arg Phe Arg Thr Thr Thr Gly Asp
Ala Met Gly Met Asn Met Ile Ser Lys Gly Val Glu Tyr Ser Leu Lys
Gln Met Val Glu Glu Tyr Gly Trp Glu Asp Met Glu Val Val Ser Val
Ser Gly Asn Tyr Cys Thr Asp Lys Lys Pro Ala Ala Ile Asn Trp Ile
Glu Gly Arg Gly Lys Ser Val Val Ala Glu Ala Thr Ile Pro Gly Asp
Val Val Arg Lys Val Leu Lys Ser Asp Val Ser Ala Leu Val Glu Leu
Asn Ile Ala Lys Asn Leu Val Gly Ser Ala Met Ala Gly Ser Val Gly
Gly Phe Asn Ala His Ala Ala Asn Leu Val Thr Ala Val Phe Leu Ala
Leu Gly Gln Asp Pro Ala Gln Asn Val Glu Ser Ser Asn Cys Ile Thr
Leu Met Lys Glu Val Asp Gly Asp Leu Arg Ile Ser Val Ser Met Pro
Ser Ile Glu Val Gly Thr Ile Gly Gly Gly Thr Val Leu Glu Pro Gln
Gly Ala Met Leu Asp Leu Leu Gly Val Arg Gly Pro His Ala Thr Ala
Pro Gly Thr Asn Ala Arg Gln Leu Ala Arg Ile Val Ala Cys Ala Val
Leu Ala Gly Glu Leu Ser Leu Cys Ala Ala Leu Ala Ala Gly His Leu
Val Gln Ser His Met Thr His Asn Arg Lys Pro Ala Glu Pro Thr Lys
Pro Asn Asn Leu Asp Ala Thr Asp Ile Asn Arg Leu Lys Asp Gly Ser
Val Thr Cys Ile Lys Ser
```

FIG. 13A

FPP synthase (ERG20)
*Saccharomyces cerevisiae*

```
  1 masekeirre rflnvfpklv eelnasllay gmpkeacdwy ahslnyntpg klnrglsvv
 61 dtyailsnkt veqlgqeeye kvailgwcie llqayflvad dmmdksitrr gqpcwykvpe
121 vgeiaindaf mleaaiykll kshfrnekyy iditelfhev tfqtelgqlm dlitapedkv
181 dlskfslkkh sfivtfktay ysfylpvala myvagitdek dlkqardvli plgeyfqiqd
241 dyldcfgtpe qigkigtdiq dnkcswvink alelasaeqr ktldenygkk dsvaeakckk
301 ifndlkieql yheyeesiak dlkakisqvd esrgfkadvl taflnkvykr sk
```

FIG. 13B

FPP synthase (ERG20) F96W/N127W

```
  1 masekeirre rflnvfpklv eelnasllay gmpkeacdwy ahslnyntpg klnrglsvv
 61 dtyailsnkt veqlgqeeye kvailgwcie llqaywlvad dmmdksitrr gqpcwykvpe
121 vgeiawdaf mleaaiykll kshfrnekyy iditelfhev tfqtelgqlm dlitapedkv
181 dlskfslkkh sfivtfktay ysfylpvala myvagitdek dlkqardvli plgeyfqiqd
241 dyldcfgtpe qigkigtdiq dnkcswvink alelasaeqr ktldenygkk dsvaeakckk
301 ifndlkieql yheyeesiak dlkakisqvd esrgfkadvl taflnkvykr sk
```

FIG. 13C

FPP synthase (ERG20) K197

```
  1 masekeirre rflnvfpklv eelnasllay gmpkeacdwy ahslnyntpg klnrglsvv
 61 dtyailsnkt veqlgqeeye kvailgwcie llqayflvad dmmdksitrr gqpcwykvpe
121 vgeiaindaf mleaaiykll kshfrnekyy iditelfhev tfqtelgqlm dlitapedkv
181 dlskfslkkh sfivtfatay ysfylpvala myvagitdek dlkqardvli plgeyfqiqd
241 dyldcfgtpe qigkigtdiq dnkcswvink alelasaeqr ktldenygkk dsvaeakckk
301 ifndlkieql yheyeesiak dlkakisqvd esrgfkadvl taflnkvykr sk
```

FIG. 14

*Perilla citriodora* geraniol synthase

GenBank ABB30217

```
  1 mssisqkvvi glnkaaannn lqnldrrgfk trcvssskaa sclrascslq ldvkpvqegr
 61 rsgnyqpsiw dfnyvqslnt pykeeryltr haelivqvkp llekkmepaq qleliddlnn
121 lglsyffqdr ikqilsfiyd enqcfhsnin dqaekrdlyf talgfrllrq hgfdvsqevf
181 dcfkndngsd fkaslsdntk gllqlyeasf lvregedtle qarqfatkfl rrkldeiddn
241 hllscihhsl eiplhwriqr learwflday atrhdmnpvi lelakldfni iqathqeelk
301 dvsrwwqntr laeklpfvrd rlvesyfwai alfephqygy qrrvaakiit latsiddvyd
361 iygtldelql ftdnfrrwdt eslgrlpysm qlfymvihnf vselayeilk ekgfivipyl
421 qrswvdlaes flkeanwyys gytpsleeyi dngsisigav avlsqvyftl ansiekpkie
481 smykyhhilr lsgllvrlhd dlgtslfekk rgdvpkavei cmkernvtee eaeehvkyli
541 reawkemnta ttaagcpfmd elnvaaanlg raaqfvyldg dghgvqhski hqqmgglmfe
601 pyv
```

FIG. 15

*Perilla frutescens* geraniol synthase

GenBank ABB30218

```
  1 mssisqkvvi glnkaaannn lqnldrrgfk trcvssskaa sclrascslq ldvkpvqegr
 61 rsgnyqpsiw dfnyvqslnt pykeeryltr haelivqvkp llekkmeaaq qleliddlnn
121 lglsyffqdr ikqilsfiyd enqcfhsnin dqaekrdlyf talgfrilrq hgfdvsqevf
181 dcfkndsgsd fkaslsdntk gllqlyeasf lvregedtle qarqfatkfl rrkldeiddn
241 hllscihhsl eiplhwriqr learwflday atrhdmnpvi lelakldfni iqathqeelk
301 dvsrwwqntr laeklpfvrd rlvesyfwai alfephqygy qrrvaakiit latsiddvyd
361 iygtldelql ftdnfrrwdt eslgrlpysm qlfymvihnf vselayeilk ekgfivipyl
421 qrswvdlaes flkeanwyys gytpsleeyi dngsisigav avlsqvyftl ansiekpkie
481 smykyhhilr lsgllvrlhd dlgtslfekk rgdvpkavei cmkernvtee eaeehvkyli
541 reawkemnta ttaagcpfmd elnvaaanlg raaqfvyldg dghgvqhski hqqmgglmfe
601 pyv
```

FIG. 16

*Camptotheca acuminate* geraniol synthase
GenBank ALL56347

```
  1 macmsvssls qstristhcn iigrfgvpsr glsqwiktss sssssslrsss whcmcttlps
 61 patstatigd tdsllksqrq ftvylpahea dkdrkieeim ektqgelekt sdptsvmkfi
121 dtlerlgiay hfeeeinsll qgflangysh ypqdlfttal rfrllrhngy hisadvfqkf
181 vdkngkfkes lredtqgmls lyeasylgan gedilsqame ftethfkqsi plmaavpqle
241 qalelprhlr marlearrfi eeyiresdhs sallelakld ynkvqllhqs elneisrwwk
301 qlglvenlgf grdrplecfl wtvgilpepk ysgcrieltk tiavllvldd ifdsfgtlde
361 lvrfthairr wdlsameqlp eymkvcymal ynttneigyk ilkehqwnvv pylkrtwidm
421 iegfqaeanw cssgyvpsle eyiengvtta gsymalvhlf flmgqgvtde tigmlepypk
481 ffsssqrilr lwddlgtase eqergdiass ielfmrekdl ssqgearkyv kqviyslwke
541 lngelmaska mplplikaaf nmartsqviy qhgddnsfps vdqcvqslff tpil
```

FIG. 17

*Citrus jambhiri* geraniol synthase
GenBank BAM29049

```
  1 msssinpstl vtsvngfkcl plttnkaair imaknkplqc lvsakydnlt vdrrsanyqp
 61 siwdhdflqs lnskytdeay krraeglkgk vkiaikdvie pldqlelidn lqrlglahrf
121 eteirmilnn iynnnkdynw rkenlyatsl efrllrqhgy pvsqevfngl kdgqgqficd
181 dfkgilslhe asyysleges imeeawqfts khlkevmisk skeehvfvae qakralelpl
241 hwkvpmlear wfihvyekre dknhlllela klefntlqai yqeelkdisg wwketglgek
301 lsfardslva sflwsmgigs epqfaycrri vtiaialitv iddiydvygt ldelelftaa
361 varwdihyal nhlpdymklc ffalynfvne fayyvlkkqd fdmlrsikns wlgllqaclv
421 eakwyhtkyt ptlgefleng lvsiggpmgi mtaylsgtnp iiekelefle snqdiihwsc
481 kifrlqddlg tssdeiqrgd vpksiecymh etgaseevar ehikdmmrqm wkkvnayrad
541 kdsplsqntv dfmlnlvrms hfmylrgdgh gaqnqetmdv astwlfqplp ledkhmafta
601 pkadefpeys fs
```

FIG. 18

*Saccharomyces cerevisiae*
GenBank NP_014771
Phosphoribosylaminoimidazole carboxylase (ADE2)

MDSRTVGILGGGQLGRMIVEAANRLNIKTVILDAENSPAKQ
ISNSNDHVNGSFSNPLDIEKLAEKCDVLTIEIEHVDVPTLKNL
QVKHPKLKIYPSPETIRLIQDKYIQKEHLIKNGIAVTQSVPVE
QASETSLLNVGRDLGFPFVLKSRTLAYDGRGNFVVKNKEMI
PEALEVLKDRPLYAEKWAPFTKELAVMIVRSVNGLVFSYPI
VETIHKDNICDLCYAPARVPDSVQLKAKLLAENAIKSFPGCG
IFGVEMFYLETGELLINEIAPRPHNSGHYTIDACVTSQFEAHL
RSILDLPMPKNFTSFSTITTNAIMLNVLGDKHTKDKELETCE
RALATPGSSVYLYGKESRPNRKVGHINIIASSMAECEQRLNY
ITGRTDIPIKISVAQKLDLEAMVKPLVGIIMGSDSDLPVMSA
ACAVLKDFGVPFEVTIVSAHRTPHRMSAYAISASKRGIKTII
AGAGGAAHLPGMVAAMTPLPVIGVPVKGSCLDGVDSLHSIV
QMPRGVPVATVAINNSTNAALLAVRLLGAYDSSYTTKMEQ
FLLKQEEEVLVKAQKLETVGYEAYLENK

FIG. 19

*Streptococcus pyogenes* Cas9

MDKKYSIGLDIGTNSVGWAVITDDYKVPSKKLKVLGNTDRHGIKKNLIGALLFDSGETAEATRLKRTARR
RYTRRKNRICYLQEIFSNEMAKVDDSFFHRLEESFLVEEDKKHERHPIFGNIVDEVAYHEKYPTIYHLRK
KLADSTDKVDLRLIYLALAHMIKFRGHFLIEGDLNPDNSDVDKLFIQLVQTYNQLFEENPINASRVDAKA
ILSARLSKSRRLENLIAQLPGEKKNGLFGNLIALSLGLTPNFKSNFDLAEDAKLQLSKDTYDDDLDNLLA
QIGDQYADLFLAAKNLSDAILLSDILRVNSEITKAPLSASMIKRYDEHHQDLTLLKALVRQQLPEKYKEI
FFDQSKNGYAGYIDGGASQEEFYKFIKPILEKMDGTEELLAKLNREDLLRKQRTFDNGSIPYQIHLGELH
AILRRQEDFYPFLKDNREKIEKILTFRIPYYVGPLARGNSRFAWMTRKSEETITPWNFEEVVDKGASAQS
FIERMTNFDKNLPNEKVLPKHSLLYEYFTVYNELTKVKYVTEGMRKPAFLSGEQKKAIVDLLFKTNRKVT
VKQLKEDYFKKIECFDSVEISGVEDRFNTSLGTYHDLLKIIKDKDFLDNEENEDILEDIVLTLTLFEDKE
MIEERLKKYANLFDDKVMKQLKRRHYTGWGRLSRKLINGIRDKQSGKTILDFLKSDGFANRNFMQLINDD
SLTFKEAIQKAQVSGQGHSLHEQIANLAGSPAIKKGILQTVKIVDELVKVMGHKPENIVIEMARENQTTQ
KGQKNSRERMKRIEEGIKELGSQILKEHPVENTQLQNEKLYLYYLQNGRDMYVDQELDINRLSDYDVDHI
VPQSFLKDDSIDNKVLTRSDKNRGKSDNVPSEEVVKKMKNYWRQLLNAKLITQRKFDNLTKAERGGLSEL
DKAGFIKRQLVETRQITKHVAQILDSRMNTKYDENDKLIREVKVITLKSKLVSDFRKDFQFYKVREINNY
HHAHDAYLNAVVGTALIKKYPKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQTGGFSKESILPKRNSDKLIA
RKKDWDPKKYGGFDSPTVAYSVLVVAKVEKGKSKKLKSVKELLGITIMERSSFEKNPIDFLEAKGYKEVR
KDLIIKLPKYSLFELENGRKRMLASAGELQKGNELALPSKYVNFLYLASHYEKLKGSPEDNEQKQLFVEQ
HKHYLDEIIEQISEFSKRVILADANLDKVLSAYNKHRDKPIREQAKNIIHLFTLTNLGAPAAFKYFDTTI
ERNRYKSIKEVLDATLIHQSITGLYEIRIDLSQLGGD

FIG. 20

*Staphylococcus aureus* Cas9

MKRNYILGLDIGITSVGYGIIDYETRDVIDAGVRLFKEANVE
NNEGRRSKRGARRLKRRRRHRIQRVKKLLFDYNLLTDHSEL
SGINPYEARVKGLSQKLSEEEFSAALLHLAKRRGVHNVNEV
EEDTGNELSTKEQISRNSKALEEKYVAELQLERLKKDGEVR
GSINRFKTSDYVKEAKQLLKVQKAYHQLDQSFIDTYIDLLET
RRTYYEGPGEGSPFGWKDIKEWYEMLMGHCTYFPEELRSV
KYAYNADLYNALNDLNNLVITRDENEKLEYYEKFQIIENVF
KQKKKPTLKQIAKEILVNEEDIKGYRVTSTGKPEFTNLKVY
HDIKDITARKEIIENAELLDQIAKILTIYQSSEDIQEELTNLNSE
LTQEEIEQISNLKGYTGTHNLSLKAINLILDELWHTNDNQIA
IFNRLKLVPKKVDLSQQKEIPTTLVDDFILSPVVKRSFIQSIKV
INAIIKKYGLPNDIIIELAREKNSKDAQKMINEMQKRNRQTN
ERIEEIIRTTGKENAKYLIEKIKLHDMQEGKCLYSLEAIPLEDL
LNNPFNYEVDHIIPRSVSFDNSFNNKVLVKQEENSKKGNRT
PFQYLSSSDSKISYETFKKHILNLAKGKGRISKTKKEYLLEER
DINRFSVQKDFINRNLVDTRYATRGLMNLLRSYFRVNNLD
VKVKSINGGFTSFLRRKWKFKKERNKGYKHHAEDALIIAN
ADFIFKEWKKLDKAKKVMENQMFEEKQAESMPEIETEQEYK
EIFITPHQIKHIKDFKDYKYSHRVDKKPNRELINDTLYSTRKDD
KGNTLIVNNLNGLYDKDNDKLKKLINKSPEKLLMYHHDP
QTYQKLKLIMEQYGDEKNPLYKYYEETGNYLTKYSKKDNG
PVIKKIKYYGNKLNAHLDITDDYPNSRNKVVKLSLKPYRFD
VYLDNGVYKFVTVKNLDVIKKENYYEVNSKCYEEAKKLKK
ISNQAEFIASFYNNDLIKINGELYRVIGVNNDLLNRIEVNMI
DITYREYLENMNDKRPPRIIKTIASKTQSIKKYSTDILGNLYE
VKSKKHPQIIKKG

FIG. 21

*Francisella tularensis* Cpf1

MNVKILPIAIDLDVKNTGVFSAFYQKGTSLEKLDNKNGKVYELSKDSYTLLM
NNRTARRHKRRGIDRKQLVKRLFKLVWTEQLNLEWDKDTQQAISFLFNR
RGFSFITDGYSTEYLNIVPEQVKAILMDIFDDYNGEDDLDSYLKLATEQES
KISEIYNKLMQKILEFKLRKLCTDIKDDKVSTKTLKEITSYEFELLADYLANYSES
LKTQKFSYTDKQGNLKELSYYHHDKYNIQEFLKRHATINDEILGTLLTDDFD
IWNFNFEKFDFDKNEEKLQNQEDKDHTQAHLHHFVFVVNKIKSEMASGG
RHRSQYFQEITNVLDENNHQEGYLKNFCENLHNKKYSNLSVKNLVNLVGNL
SNLELKPLRKYFNDKIHAKADHWDEQKFTETYCHWILGEWRVGVKDQ
DKKDGAKYSYKDLCNELKQKVTKAGLIDFLLELDPCRTIPPYLDNNNRKP
PKCQSLILNPKFLDNQYPNWQQYLQELKKLQSIQDYLDSFETDLKDLKSSKD
QPYFVEYKSSNQQMASGQRDYKDLDARILQFIFDRVKASDELLLNEIYFQA
KKLKQKASSELEKLESSKKLDEVIANSQLSQILKSQHTNGIFEQGTFLHLVCK
YYKQRQRARDSRLYIMPEYRYDKKLDKYNNTGRFDDNNQLLTYCNHKPRQ
KRYQLLNDLAGVLQVSRNQLLSSVEEWFQQAQRVGEISKSQDEQIFEW
LKSFKIASYCKAAVEMQKQYRGTLKNAIQTAIFRQSENINKNKNTGNQQQ
ALSENSKDVKSLTADEKKLLKLIENIAKASQKIGESLGLNDKQIKKFNSIYSFA
QIQQIAFAKRKGNANTCAVCSADNAHRMQQIKITELVEDNKDNIILSAKAQ
RLPAIPTRIVDGAVKKMATILAKNIVDDNWQNIKQVLSAKHQLHIPIITES
NAFEFEPALADVKGKSLKDRRKKALERISPENIFKDKNNRIKEFAKGISAYSGA
NLTDGDFDGAKEELDHIIPRSHKKYGTLNDEANLICVTRDDNKNIFAIDT
SKWFEIETPSDLRDIGVATIQYKIDNNSRPKVRVKLDYVIDDDSKINYFMNH
SLLKSRYPDKVLEILKQSTIIEFESSGFNKTIKEMLGMTLAGIYNETSNN

FIG. 27

*Olea europaea* geraniol synthase
GenBank: AFI47926.1

```
  1 mdctmtsisl fsqssngisg tarspfqwpi nhrfssgqrd fickslpvss psatplipae
 61 ngamynyirq pvivtpevdd gtkhselver trrelqrstk pvetlklidn lqrlgiayyf
121 eddinaildq fsdglpdedl fttalcfrll rdqrlqtgsd vflkfmeknm kfkehlaqdt
181 iglvslyeas smgangeeil seakeftemh lrqsmpqlap qlrrqvssal elprhlrmar
241 learryieey gnesdhdpal lelarldynk vqlqhqmela eitrwwkqlg lveklsfard
301 rplecflwtv gllpepkyss crielaktia illviddifd tygkmeelvl fteaiqrwdl
361 deletlppym ricymalynt tneicykilk eygfcvlpyl kstwidmieg fmveanwfng
421 ghgpnleeyi engvstagay malvhlffli gegvtnenia kllrkpypkl fsaagrilrl
481 wddlgtakee eergdlascm qilmreknid cenegrnyil kainglwkdl ndelispnam
541 plaitkvaln marafevvyk heedsyfssv dnyvqalfft pin
```

FIG. 28

*Phyla dulcis* geraniol synthase
GenBank: ADK62524.1

```
  1 masarstisl ssqsshhgfs knsfpwqlrh srfvmgsrar tcacmsssvs lptattsssv
 61 itgndallky irqpmviplk ekegtkrrey llektarelq gtteaaeklk fidtiqrlgi
121 scyfedeing ilqaelsdtd qledglftta lrfrllrhyg yqiapdvflk ftdqngkfke
181 sladdtqglv slyeasymga ngenileeam kftkthlqgr qhamrevaea lelprhlrma
241 rlearryieq ygtmighdkd llelvildyn nvqaqhqael aeiarwwkel glvdkltfar
301 drplecflwt vgllpepkys acrielakti aillviddif dtygkmeela lfteairrwd
361 leametlpey mkicymalyn ttneicykvl kkngwsvlpy lrytwmdmie gfmveakwfn
421 ggsapnleey iengvstaga ymalvhlffl igegvsaqna qillkkpypk lfsaagrilr
481 lwddlgtake eegrgdlass irlfmkeknl tteeegrngi qeeiyslwkd lngeliskgr
541 mplaiikval nmarasqvvy khdedsyfsc vdnyvealff tpll
```

FIG. 29

*Vilis vinifera* geraniol synthase
GenBank: NP_001267920.1

```
  1 mafnmsrfvt mpshvlpssf vapslqvsss pcswrtrpsp ctschlspss sskpllgshd
 61 ysllksltls phavnseads strrmkevke rtweafyraw dsraamemvd tverlglsyh
121 fedeinallq rfcdwnased lfttalrfrl lrqngfpths dvfgkfmdkn gkfkeslted
181 irgmlslhea shlgakneev laeakeftri hliqsmphme phfsshvgra lelprhlrmv
241 rlearnyige ysresnpnla flelakldfd mvqslhqkel aeilrwwkql glvdkldfar
301 drpmecflwt vgifpdprhs scrieltkai aillviddiy dsygsldela lftdavkrwd
361 lgamdqlpey mkicymalyn ttndiayril kehgwsvieh lkrtwmdifg aflaeaycfk
421 gghvpsleey ltnavttggt ymalvhaffl mgqgvtrenm amlkpypnif scsgkilrlw
481 ddlgtareeq ergdnassie cykreremdt vledeacrkh irqmiqslwv elngelvass
541 alplsiikaa fnlsrtaqvi yqhgddnkts svedhvqall frpvssngha qitmh
```

FIG. 30

*Ocimum basilicum* geraniol synthase
UniProtKB/Swiss-Prot: Q6USK1.1

```
  1 mscaritvtl pyrsaktsiq rgithypali rprfsactpl asamplsstp lingdnsqrk
 61 ntrqhmeess skrreyllee ttrklqrndt esveklklid niqqlgigyy fedainavlr
121 spfstgeedl ftaalrfrll rhngieispe iflkfkderg kfdesdtlgl lslyeasnlg
181 vageeileea mefaearlrr slsepaaplh gevaqaldvp rhlrmarlea rrfieqygkq
241 sdhdgdllel aildynqvqa qhqselteii rwwkelglvd klsfgrdrpl ecflwtvgll
301 pepkyssvri elakaisill viddifdtyg emddlilftd airrwdleam eglpeymkic
361 ymalynttne vcykvlrdtg rivllnlkst widmiegfme eakwfnggsa pkleeyieng
421 vstagaymaf ahiffligeg vthqnsqlft qkpypkvfsa agrilrlwdd lgtakeeqer
481 gdlascvqlf mkekslteee arsrileeik glwrdlngel vynknlplsi ikvalnmara
541 sqvvykhdqd tyfssvdnyv dalfftq
```

FIG. 36

OYE2 Saccharomyces cerevisiae
Genbank: KZV10919.1

```
  1 mpfvkdfkpq algdtnlfkp ikignnellh ravippltrm raqhpgnipn rdwaveyyaq
 61 raqrpgtlii tegtfpspqs ggydnapgiw seeqikewtk ifkaihekks fawvqlwvlg
121 waafpdtlar dglrydsasd nvymnaeqee kakkannpqh sitkdeikqy vkeyvqaakn
181 siaagadgve ihsangylln qfldphsnnr tdeyggsien rarftlevvd avvdaigpek
241 vglrlspygv fnsmsggaet givaqyayvl gelerrakag krlafvhlve prvtnpflte
301 gegeynggsn efaysiwkgp iiragnfalh pevvreevkd prtligygrf fisnpdlvdr
361 lekglplnky drdtfykmsa egyidyptye ealklgwdkn
```

FIG. 37A

TDH3
cagttcgagtttatcattatcaatactgccatttcaaagaatacgtaaataattaatagtagtgattttcctaactttatttagt
caaaaaattagccttttaattctgctgtaacccgtacatgcccaaaatagggggcgggttacacagaatatataacatcgt
aggtgtctgggtgaacagtttattcctggcatccactaaatataatggagcccgcttttaagctggcatccagaaaaaaa
aagaatcccagcaccaaaatattgttttcttcaccaaccatcagttcataggtccattctcttagcgcaactacagagaaca
ggggcacaaacaggcaaaaaacgggcacaacctcaatggagtgatgcaacctgcctggagtaaatgatgacacaagg
caattgacccacgcatgtatctatctcattttcttacaccttctattaccttctgctctctctgatttggaaaaagctgaaaaa
aaaggttgaaaccagttccctgaaattattcccctacttgactaataagtatataaagacggtaggtattgattgtaattctg
taaatctatttcttaaacttcttaaattctactttatagttagtctttttttagttttaaaacaccaagaacttagtttcgaata
aacacacataaacaaacaaa ALD6
taagggcatgatagaattggattatgtaaaaggtgaagataccattgtagaagcaaccagcacgtcgccgtggctgatga
agtctcctcttgcccgggccgcagaaaagaggggcagtggcctgttttcgacataaatgagggcatggccagcaccaa
gacgtcattgttgcatatggcgtatccaagccgaaacggcgctcgcctcatccccacgggaataaggcagccgacaaaa
gaaaaacgaccgaaaaggaaccagaaagaaaaaagagggtgggcgcgccgcggacgtgtaaaaagatatgcatcca
gcttctatatcgctttaactttaccgttttgggcatcgggaacgtatgtaacattgatctcctcttgggaacggtgagtgcaa
cgaatgcgatatagcaccgaccatgtgggcaaattcgtaataaattcggggtgaggggggattcaagacaagcaaccttgt
tagtcagctcaaacagcgatttaacggttgagtaacacatcaaaacaccgttcgaggtcaagcctggcgtgtttaacaagt
tcttgatatcatatataaatgtaataagaagtttggtaatattcaattcgaagtgttcagtcttttacttctcttgttttatagaa
gaaaaaacatcaagaaacatctttaacatacacaaacacatactatcagaataca PGK1
gtgagtaaggaaagagtgaggaactatcgcatacctgcatttaaagatgccgatttgggcgcgaatcctttattttggcttc
accctcatactattatcagggccagaaaaaggaagtgtttcctccttcttgaattgatgttaccctcataaagcacgtggc
ctcttatcgagaaagaaattaccgtcgctcgtgatttgtttgcaaaaagaacaaaactgaaaaaacccagacacgctcga
cttcctgtcatcctattgattgcagcttccaatttcgtcacacaacaaggtcctagcgacggctcacaggttttgtaacaagc
aatcgaaggttctggaatggcgggaaagggttagtaccacatgctatgatgcccactgtgatctccagagcaaagttcgt
tcgatcgtactgttactctctctctttcaaacagaattgtccgaatcgtgtgacaacaacagcctgttctcacacactcttttc
ttctaaccaaggggggtggtttagtttagtagaacctcgtgaaacttacatttacatatatataaacttgcataaaattggtcaa
tgcaagaaatacatatttggtcttttctaattcgtagttttcaagttcttagatgctttcttttctctttttacagatcatcaa
ggaagtaattatctactttttacaacaaatataaaaca TEF1
ccttgccaacagggagttcttcagagacatggaggctcaaaacgaaattattgacagcctagacatcaatagtcatacaa
cagaaagcgaccaccaactttggctgataatagcgtataaacaatgcatactttgtacgttcaaaatacaatgcagtaga
tatatttatgcatattacatataatacatatcacataggaagcaacaggcgcgttggactttaattttcgaggaccgcgaa
tccttacatcacacccaatccccacaagtgatcccccacacaccatagcttcaaaatgtttctactcctttttactcttcca
gattttctcggactccgcgcatcgccgtaccacttcaaaacacccaagcacagcatactaaatttcccctctttcttcctcta
gggtgtcgttaattacccgtactaaaggtttggaaaagaaaaaagacaccgcctcgtttcttttttcttcgtcgaaaaaggca
ataaaaattttttatcacgtttcttttttcttgaaaatttttttttttgattttttttctctttcgatgacctcccattgatatttaagtta
ataaacggtcatcaatttctcaagtttcagtttcattttttcttgttctattacaactttttttacttcttgctcattagaaagaaag
catagcaatctaatctaagttttaattacaaa

FIG. 37B

TEF2
ttgataggtcaagatcaatgtaaacaattactttgttatgtagagttttttagctacctatattccaccataacatcaatcat
gcggttgctggtgtatttaccaataatgtttaatgtatatatatatatatatatgggccgtatacttacatatagtagatg
tcaagcgtaggcgcttcccctgccggctgtgagggcgccataaccaaggtatctatagaccgccaatcagcaaactacct
ccgtacattcatgttgcacccacacatttatacacccagaccgcgacaaattacccataaggttgtttgtgacggcgtcgta
caagagaacgtgggaacttttaggctcaccaaaaaagaaagaaaaaatacgagttgctgacagaagcctcaagaaaa
aaaaaattcttcttcgactatgctggaggcagagatgatcgagccggtagtaactatatatagctaaattggttccatcac
cttcttttctggtgtcgctccttctagtgctatttctggcttttcctattttttttttttccattttctttctctctttctaatatataaa
ttctcttgcatttctattttctctctatctattctacttgttattcccttcaaggtttttttttaaggagtacttgttttagaata
tacggtcaacgaactataattaactaaac CCW12
cacccatgaaccacacggttagtccaaaaggggcagttcagattccagatgcgggaattagcttgctgccacccteacct
cactaacgctgcggtgtgcggatacttcatgctatttatagacgcgcgtgtcggaatcagcacgcgcaagaaccaaatgg
gaaaatcggaatgggtccagaactgctttgagtgctggctattggcgtctgatttccgttttgggaatcctttgccgcgcgc
ccctctcaaaactccgcacaagtcccagaaagcgggaaagaaataaaacgccaccaaaaaaaaaaaaataaaagcca
atcctcgaagcgtgggtggtaggccctggattatcccgtacaagtatttctcaggagtaaaaaaaccgtttgttttggaatt
tcccatttcgcggccacctacgccgctatctttgcaacaactatctgcgataactcagcaaattttgcatattcgtgttgcag
tattgcgataatgggagtcttacttccaacataacggcagaaagaaatgtgagaaaattttgcatcctttgcctccgttcaa
gtatataaagtcggcatgcttgataatctttctttccatcctacattgttctaattattcttattctcctttattctttcctaacata
ccaagaaattaatcttctgtcattcgcttaaacactatatcaataa HHF1
tcttggggccttaccaccagtggactttcttgctgtttgctttgttctggccattgtttgcgtttatatatttatgttagatgttttt
cttattaactagaaagaaagaatataaaaggttgaggaaagagatgtatcccgaagaatacacagtctttatatatgtat
ttcaacaaggagccgtggagggtactaaaaagaaaaatcgcccgggcatttcgttatcttccacgctaaaagtcaaggag
agatattacggccaggatcgcaaaggtgcagagcaaggaaatgtgagaaattgtgagaacgataatgtatgggacaat
gcgaaaatgtgagaacgagagcaaaaatctttttttgtatctccccgccgaatttggaaaccgcgttctgaaaacttcgcat
cttcacatagtaaaactgttccgagcgcttctccccataatggttagtggtaaaaaccgaagttgtttactttagcaaatgcc
cgcgaatacggtggtaaattgccaccccccccttccccattcattgggtaaagaccaatttgatggataaattggttgtggaa
aaggtctaattctttttcctataaataccgagatatttttctatatgatggtttccgtcgcattattgtactctatagtactaaa
gcaacaaacaaaaacaagcaacaaatataatatagtaaaat HHF2
tgtggagtgtttgcttggattctttagtaaaaggggaagaacagttggaagggccaaagtggaagtcacaaaacagtggt
cctatataaaagaacaagaaaaagattatttatatacaactgcggtcacaagaagcaacgcgagagagcacaacacgct
gttatcacgcaaactatgttttgacaccgagccatagccgtgattgtgcgtcacattgggcgataatgaacgctaaatgac
caactcccatccgtaggagcccttagggcgtgccaatagtttcacgcgcttaatgcgaagtgctcggaacggacaactgt
ggtcgtttggcaccgggaaagtggtactagaccgagagtttcgcatttgtatggcaggacgttctgggagcttcgcgtcta
aagcttttcgggcgcgaaatgcagaccagaccagaacaaaacaactgacaagaaggcgtttaatttaatatgttgttca
ctcgcgcctgggctgttgttattcggctagatacatacgtgtttgtgcgtatgtagttatatcatatataagtatattaggatg
aggcggtgaaagagatttttttttttttcgcttaatttattctttttctctatcttttttcctacatcttgttcaaaagagtagcaaaa
acaacaatcaatacaataaaata

FIG. 37C

PAB1
aaggcaagcccagaaaaatatcgcaagcacctttggtcttacagtgccaacttttggcctgccgacgttaagagtacaaa
gctgatggcaatgtacgacaagataacagagtctcaaaagaagtgaaacaattttcttcaccacattttccattgttcctt
cccccataactataaacgtatttatgtatatatatttgcgtgtaagtgtgtgtactataagggcaccgtaaagtaataatgct
taattagttactactatgaccatataagaggtcatactgtatgaagccacaaagcagatagatcaatcatgtttaacgaaa
actgttaatcgaagattatttctttttttttttctctttcctttttacaaagaaaatttttttgcgcttttttgccatcaccatcgca
agttctgggacaattgttctcttcgctccagttccaaggaaagaggtttctgttttacttaatagaaagtgtcatcttgtattt
tatatctcttctttcttgtgtaaaattctttagttttgattttgtattttaggacagtgagctacgaagtaacattttacttaat
aaccgtttgaagcatagagcaggccctggtatcaccacctaatatctggcttttattcaataaaaactcaaaaaaaaaa
tccaaaaaaaactaaaaaaccaataaaaataaa RPL18b
aagaggatgtccaatatttttttttaaggaataaggatacttcaagactagattccccctgcattcccatcagaaccgtaaa
ccttggcgctttccttgggaagtattcaagaagtgccttgtccggtttctgtggctcacaaaccagcgcgcccgatatggctt
tcttttcacttatgaatgtaccagtacgggacaattagaacgctcctgtaacaatctctttgcaaatgtggggttacattcta
accatgtcacactgctgacgaaattcaaagtaaaaaaaaatgggaccacgtcttgagaacgatagattttctttattttaca
ttgaacagtcgttgtctcagcgcgctttatgttttcattcatacttcatattataaaataacaaaagaagaatttcatattcac
gcccaagaaatcaggctgctttccaaatgcaattgacacttcattagccatcacacaaaactctttcttgctggagcttcttt
taaaaaagacctcagtacaccaaacacgttacccgacctcgttattttacgacaactatgataaaattctgaagaaaaat
aaaaaaattttcatacttcttgcttttatttaaaccattgaatgatttcttttgaacaaaactacctgtttcaccaaaggaaat
agaaagaaaaatcaattagaagaaaacaaaaaacaaa RNR1
ggatatcgtaaacaaaggcgttaccatagaaatgtactgattggcagaattactcttcaggagaatctttcatacaaaggt
attccattggggaaaatctcgttaccaagtcaatgctgaactttctatggcctttgtttactatcgttaattattttacgaccac
ttctgggtagaaatatttcgtagccctggaacgagcttgtttacgcgttttatcccattatatggcacccaaatcaaatttaa
aaagaaaaaacgcgtaaacagtgtcgggtaagttcatcctctgttactttaattgcttctttttttgaaattctaagtaaacg
cgtcattttgatcctcaggacacagaaatccttgcagaatcttattgggtgttgaatagaggacgcgtaaaaacgatatgg
aaatttttttcatatagtgtagaaagaataggttggcgtaggtagtttcgtgtttgatagaaacctccaacaaagtctgcaa
ctcacgttttagaataacaagtttagagtttatcttgttgcctttgttaagtcagtaccattgaataaaaattatataaaggag
ctaatatttcattgttggaaaattactctaccataattgaagcatatctcatccttttcatccttttcaacgcaagagagacac
caacgaacaacactttatttgttgatatattaacatc RNR2
agtcgaacaagaagcaggcaaagtttagagcactgcccctccgcactcaaaaaagaaaaaactaggaggaaaataaa
attctcaaccacacaaacacataaacacatacaaatacaaatacaagcttatttacttgacatcgcgcgatcttccactatt
cagcgccgtccgccctctctcgtgttttttgtttacgcgacaactatgcgaaatccggagcaacgggcaaccgtttgggga
aagaccacacccacgcgcgatcgccatggcaacgaggtcgcacacgccccacacccagacctccctgcgagcgggcat
gggtacaatgtccccgttgccacagacaccacttcgtagcacagcgcagagcgtagcgtgttgttgctgctgacaaaaga
aaattttctagcaaagcaaaggaggggaagcacgggcagatagcaccgtaccataccccttggaaactcgaaatgaac
gaagcaggaaatgagagaatgagagttttgtaggtatatatagcggtagtgtttgcgcgttaccatcatcttctggatctat
ctattgttcttttcctcatcacttttccccttttcgctcttcttcttgtcttttatttctttctttttttaattgttccctcgattggcta
tctaccaaagaatccaaacttaatacacgtatttatttgtccaattacc

FIG. 37D

HTB2
tatatattaaatttgctcttgttctgtactttcctaattcttatgtaaaaagacaagaatttatgatactatttaataacaaaaa
actacctaagaaaagcatcatgcagtcgaaattgaaatcgaaaagtaaaactttaacggaacatgtttgaaattctaaga
aagcatacatcttcatcccttatatatagagttatgtttgatattagtagtcatgttgtaatctctggcctaagtatacgtaac
gaaaatggtagcacgtcgcgtttatggcccccaggttaatgtgttctctgaaattcgcatcactttgagaaataatgggaac
accttacgcgtgagctgtgcccaccgcttcgcctaataaagcggtgttctcaaaatttctccccgttttcaggatcacgagc
gccatctagttctggtaaaatcgcgcttacaagaacaaagaaaagaaacatcgcgtaatgcaacagtgagacacttgcc
gtcatatataaggttttggatcagtaaccgttatttgagcataacacaggttttaaatatattattatatatcatggtatatgt
gtaaaattttttttgctgactggttttgtttatttatttagcttttaaaaattttactttcttcttgttaattttttctgattgctctat
actcaaaccaacaacaacttactctacaacta

FIG. 38

| Strain (group 1) | tHMG1 Promoter | ERG20-F96W-N127W Promoter | trnc67-McliS Promoter | ObGES Promoter | Linalool production (mg/L) | Geraniol production (mg/L) |
|---|---|---|---|---|---|---|
| A1 | TDH3 | PGK1 | HHF2 | CCW12 | 0.1154562 | 0.2481113 |
| A2 | TDH3 | PGK1 | HHF2 | HTB2 | 3.842836 | 0.5025367 |
| A4 | TDH3 | PGK1 | RPL18b | CCW12 | 0.161585 | 0.5431883 |
| A10 | TDH3 | HHF1 | HHF2 | CCW12 | 0.1636209 | 0.2238032 |
| A11 | TDH3 | HHF1 | HHF2 | HTB2 | 0.08885234 | 0.08268246 |
| B2 | TDH3 | HHF1 | RPL18b | HTB2 | 0.06506885 | 0.09386021 |
| B3 | TDH3 | HHF1 | RPL18b | RNR1 | 0.05380055 | 0.07289692 |
| B11 | TDH3 | PAB1 | RPL18b | HTB2 | 0.05402032 | 0.08328772 |
| C2 | TDH3 | PAB1 | RNR2 | HTB2 | 0.02060714 | 0.04752985 |
| C4 | TEF2 | PGK1 | HHF2 | CCW12 | 0.3376448 | 0.4047944 |
| C6 | TEF2 | PGK1 | HHF2 | RNR1 | 0.2938103 | 0.1012746 |
| C8 | TEF2 | PGK1 | RPL18B | HTB2 | 0.1671474 | 0.1154367 |
| D7 | TEF2 | HHF1 | RNR2 | CCW12 | 0.06695002 | 0.3803404 |
| D8 | TEF2 | HHF1 | RNR2 | HTB2 | 0 | 0.05162033 |
| D9 | TEF2 | HHF1 | RNR2 | RNR1 | 0 | 0.01115426 |
| E2 | TEF2 | PAB1 | RPL18B | HTB2 | 0.07608699 | 0 |
| E7 | ALD6 | PGK1 | HHF2 | CCW12 | 0.3544389 | 0 |
| F7 | ALD6 | HHF1 | RPL18B | CCW12 | 0.003546173 | 0.008335548 |

FIG. 38 (Cont.)

| Strain (group 2) | tHMG1 Promoter | ERG20-F96W-N127W Promoter | trnc67-McLIS Promoter | ObGES Promoter | Linalool production (mg/L) | Geraniol production (mg/L) |
|---|---|---|---|---|---|---|
| RL7-249 | PGK1 | HHF2 | HTB2 | CCW12 | 0.1172282 | 0.4441253 |
| RL7-250 | PGK1 | CCW12 | TEF2 | HHF2 | 3.583744 | 1.4278 |
| RL7-252 | PGK1 | TDH3 | RPL18b | HHF2 | 0.2455035 | 0.2138566 |
| RL7-253 | PGK1 | TEF1 | CCW12 | HHF2 | 1.41759 | 0.0340515 |
| RL7-254 | PGK1 | HHF1 | TEF1 | TEF2 | 0.4634725 | 0.1488524 |
| RL7-255 | TEF2 | HHF2 | TEF1 | CCW12 | 0.6141579 | 0.3881068 |
| RL7-256 | TEF2 | CCW12 | RPL18b | TDH3 | 1.010786 | 1.452613 |
| RL7-257 | TEF2 | CCW12 | TEF1 | TDH3 | 0.7739413 | 0.04171281 |
| RL7-258 | TEF2 | PGK1 | TEF1 | HHF2 | 0.8824493 | 0.1727375 |
| RL7-260 | TEF2 | TEF1 | HTB2 | TDH3 | 0.2613384 | 0.4334726 |
| RL7-261 | TEF2 | TEF1 | HTB2 | HHF2 | 0.5062652 | 0.8559799 |
| RL7-262 | TEF2 | HHF2 | RPL18b | TDH3 | 0.0217348 | 0 |
| RL7-263 | CCW12 | PGK1 | TEF1 | TDH3 | 0.6262123 | 0.4931399 |
| RL7-264 | CCW12 | HHF1 | RPL18b | HHF2 | 0.04814882 | 0.004675604 |
| RL7-265 | CCW12 | TEF1 | HTB2 | HHF2 | 0.1035025 | 0.4801061 |
| RL7-267 | CCW12 | HHF1 | TEF1 | TDH3 | 0.2665285 | 0.03578643 |
| RL7-269 | HHF2 | CCW12 | RPL18b | TEF2 | 0.2949616 | 0.7038168 |
| RL7-272 | HHF2 | TDH3 | TEF2 | CCW12 | 0.468601 | 0.4612896 |
| RL7-273 | HHF2 | CCW12 | TEF2 | TDH3 | 0.558342 | 0.2090521 |
| RL7-274 | HHF2 | TDH3 | RPL18b | CCW12 | 0.1931705 | 0.5730203 |
| RL7-275 | HHF2 | TEF1 | HTB2 | TDH3 | 0.2478932 | 0.5710828 |
| RL7-276 | TDH3 | HHF1 | TEF2 | HHF2 | 0.1904259 | 0 |
| RL7-277 | TDH3 | CCW12 | TEF1 | TEF2 | 0.4783487 | 0.3692523 |
| RL7-278 | TDH3 | HHF1 | TEF1 | HHF2 | 0.1121655 | 0 |
| RL7-281 | TDH3 | HHF2 | HTB2 | TEF2 | 0.028715 | 0.06940514 |
| RL7-282 | TDH3 | HHF1 | RPL18b | CCW12 | 0.03990794 | 0.03006077 |
| RL7-285 | CCW12 | PGK1 | TEF2 | HHF2 | 0.2744388 | 0.08955693 |
| A3 | TDH3 | PGK1 | HHF2 | RNR1 | 0.595182 | 0 |
| B7 | TDH3 | PAB1 | HHF2 | CCW12 | 0.1617582 | 0 |
| D1 | TEF2 | HHF1 | HHF2 | CCW12 | 0.6334372 | 0.5280031 |

MONOTERPENE-PRODUCING GENETICALLY MODIFIED HOST CELLS AND METHODS OF USE OF SAME

CROSS-REFERENCE

This application is a national stage application under 35 U.S.C. § 371 of PCT/US2016/065944, filed Dec. 9, 2016, which claims the benefit of U.S. Provisional Patent Application No. 62/265,943, filed Dec. 10, 2015 and U.S. Provisional Patent Application No. 62/312,368, filed Mar. 23, 2016, which applications are incorporated herein by reference in their entirety.

STATEMENT OF GOVERNMENTAL SUPPORT

This invention was made with government support under Contract No. DE-AC02-05CH11231 awarded by the U.S. Department of Energy, and Grant No. MCB 1330914 awarded by the National Science Foundation. The government has certain rights in the invention.

SUMMARY

The present disclosure provides a genetically modified host cell capable of producing a monoterpene. The present disclosure provides a genetically modified host cell capable of producing linalool. The present disclosure provides a genetically modified host cell capable of producing jet fuel, or a precursor of jet fuel. The present disclosure provides a genetically modified host cell capable of producing one or more of linalool, geraniol, and citronellol; such a genetically modified host cell is useful for producing a beverage, e.g., beer.

The present disclosure provides a genetically modified host cell capable of producing a monoterpene, such as linalool (or 3,7-dimethylocta-1,6-dien-3-ol), geraniol, and citronellol.

Linalool has the following chemical structure:

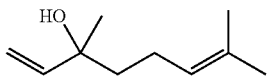

Linalool can be further converted into tetrahydromethylcyclopentadiene dimer (also known as TH-dimer or RJ-4), which can be used as a high density fuel suitable for ramjet or missile propulsion, and has the following chemical structure:

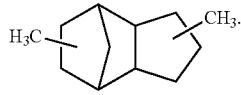

U.S. 2015/0011807 discloses a method for the conversion of renewable, linear terpene alcohol, linalool into a drop-in, high density fuel suitable for ramjet or missile propulsion.

The present invention provides for a genetically modified host cell capable of producing linalool comprising one or more of the proteins and/or modules described in FIG. 3A.

The present invention provides for a recombinant nucleic acid that encodes one or more of the proteins and/or modules described in FIG. 3A. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acid and/or one or more of the proteins and/or modules described in FIG. 3A of the present invention. In some embodiments, the host cell, when cultured under a suitable condition, is capable of producing the linalool.

For each of the enzymes described in FIG. 3A, a functional variant of the enzyme can be used instead of the enzyme described.

The present invention provides a method of producing a linalool, comprising: providing a host cell of the present invention, and culturing said host cell in a suitable culture medium such that the linalool is produced.

In some embodiments, the method further comprises separating the linalool from the host cell and the culture medium. In some embodiments, the method further comprises reacting the linalool, with at least one Ru-metathesis catalysts with a solvent or under solvent-free conditions to produce 1-methylcyclopent-2-enol; dehydrating said 1-methylcyclopent-2-enol with at least one heterogeneous dehydration catalyst to produce methylcyclopentadienes; thermal dimerizing of said methylcyclopentadienes to produce methylcyclopentadiene dimers; hydrogenating said methylcyclopentadienes dimers with at least one hydrogenation catalyst to produce hydrogenated methylcyclopentadienes dimers; and isomerizing said hydrogenated methylcyclopentadienes dimers with at least one Lewis acid catalyst to produce high density fuels.

In some embodiments, the method further comprises introducing linalool to a beverage, or precursor to a beverage. In some embodiments, the beverage is a fermented beverage comprising ethanol, such as beer.

In some embodiments, the host cell is a brewer's yeast. The present invention provides a method of producing a fermented beverage, comprising: providing a host cell of the present invention, wherein the host cell is a brewer's yeast, and culturing said host cell in a suitable culture medium to produce a fermented beverage, such that the linalool is produced and provides flavor to the fermented beverage. In some embodiments, the method does not require the addition of hops to flavor the fermented beverage. In some embodiments, the fermented beverage is a beer.

These and other objects, advantages, and features of the invention will become apparent to those persons skilled in the art upon reading the details of the invention as more fully described below.

The present disclosure provides a genetically modified host cell, wherein the host cell is genetically modified with a heterologous nucleic acid comprising a nucleotide sequence encoding linalool synthase. In some cases, the linalool synthase comprises an amino acid sequence having at least 75%, at least 80%, at least 85%, at least 90%, at least 95%, at least 98%, at least 99%, or 100%, amino acid sequence identity to the amino acid sequence depicted in one of FIGS. 4, 5, 6B, and 7-10. In some cases, the genetically modified host cell is a yeast cell. In some cases, the yeast cell is diploid. In some cases, the yeast cell is tetraploid. In some cases, the genetically modified host cell produces linalool in an amount of at least 0.5 mg per liter of medium. In some cases, the genetically modified host cell produces linalool in an amount of at least 1 mg per dry cell weight. In some cases, the genetically modified host cell is genetically modified with a nucleic acid comprising a nucleotide sequence encoding a truncated 3'-hydroxy-3-methylglutaryl-coenzyme A reductase (tHMGR). In some cases, the tHMGR comprises an amino acid sequence having at least 75%, at least 80%, at least 85%, at least 90%, at least 95%, at least 98%, at least 99%, or 100%, amino acid sequence identity to the tHMGR amino acid sequence depicted in FIG. 12, and has a length of about 502 amino acids. In some cases, the genetically modified host cell is genetically modified such that the endogenous farnesyl diphosphate synthase (FPPS) is modified to comprise one or more amino acid substitutions at positions selected from F96, N127, and K197, relative to the amino acid sequence depicted in FIG. 13A. In some cases, the modified FPPS comprises an amino acid sequence having at least 75%, at least 80%, at least 85%, at least 90%, at least 95%, at least 98%, at least 99%, or 100%, amino acid sequence identity to the FPPS amino acid sequence depicted in FIG. 13B, and comprises an F96W substitution and an N127W substitution. In some cases, the modified FPPS comprises an amino acid sequence having at least 75%, at least 80%, at least 85%, at least 90%, at least 95%, at least 98%, at least 99%, or 100%, amino acid sequence identity to the FPPS amino acid sequence depicted in FIG. 13C, and comprises a K197E substitution. In some cases, the genetically modified host cell is genetically modified with a heterologous nucleic acid comprising a nucleotide sequence encoding a geraniol synthase. In some cases, the geraniol synthase comprises an amino acid sequence having at least 75%, at least 80%, at least 85%, at least 90%, at least 95%, at least 98%, at least 99%, or 100%, amino acid sequence identity to the geraniol synthase depicted in any one of FIG. 14-17 or any one of FIG. 27-30. In some cases, the genetically modified host cell produces linalool and geraniol. In some cases, the linalool synthase has a length of from 530 amino acids to 550 amino acids. In some cases, the linalool synthase has a length of 540 amino acids. In some cases, the linalool synthase does not comprise a plastid targeting sequence.

The present disclosure provides a composition comprising: a) a genetically modified host cell as described above or elsewhere herein; and b) a culture medium. The present disclosure provides a method of producing a fermented beverage, the method comprising culturing a composition as described above or elsewhere herein for a time period and under conditions suitable for fermentation. In some cases the composition comprises barley malt. In some cases the composition comprises a barley syrup. In some cases, the composition comprises unmalted barley. In some cases the composition comprises wort. In some cases the composition comprises fruit juice with a high sugar content, e.g., apple juice or pear juice. In some cases, the composition comprises an extract of a cereal. In some cases, the cereal is selected from the group consisting of barley, wheat, rye, oat, maize, rice, sorghum, millet, triticale, buckwheat, fonio and *quinoa*. In some cases, the cereal is selected from the groups consisting of barley, wheat, rye, oat, maize and rice. In some cases, the cereal is barley.

The present disclosure provides a fermented beverage generated by a method as described above or elsewhere herein. In some cases, the fermented beverage is beer.

The present disclosure provides a nucleic acid comprising a nucleotide sequence encoding a linalool synthase comprising an amino acid sequence having at least 75%, at least 80%, at least 85%, at least 90%, at least 95%, at least 98%, at least 99%, or 100%, amino acid sequence identity to the amino acid sequence depicted in FIG. 6B, and having a length of from 530 amino acids to 550 amino acids. In some cases the linalool synthase has a length of 540 amino acids.

In some cases the nucleotide sequence is operably linked to a promoter that is functional in a yeast cell. In some cases the promoter is a GAL1 promoter or a GAL10 promoter.

BRIEF DESCRIPTION OF THE DRAWINGS

The foregoing aspects and others will be readily appreciated by the skilled artisan from the following description of illustrative embodiments when read in conjunction with the accompanying drawings.

FIG. 2A-2D depict amino acid sequences of various enzymes, and production of geraniol or linalool by the enzymes. Sequences in FIG. 2A from top to bottom are set forth in SEQ ID NOs:1-6. Sequences in FIG. 2B from top to bottom are set forth in SEQ ID NOs:46-51.

FIG. 4 provides an amino acid sequence of *Actinidia polygama* linalool synthase (SEQ ID NO:7).

FIG. 5 provides an amino acid sequence of *Mentha citrata* linalool synthase (SEQ ID NO:8).

FIG. 6A provides a nucleotide sequence encoding a modified *Mentha citrata* linalool synthase lacking the plastid targeting sequence (PTS) present in wild-type *Mentha citrata* linalool synthase (SEQ ID NO:9).

FIG. 6B provides an amino acid sequence of modified *Mentha citrata* linalool synthase lacking the PTS present in wild-type *Mentha citrata* linalool synthase (SEQ ID NO: 10).

FIG. 7 provides an amino acid sequence of *Thymus vulgaris* linalool synthase (SEQ ID NO:11).

FIG. 8 provides an amino acid sequence of *Perilla frutescens* linalool synthase (SEQ ID NO:12).

FIG. 9 provides an amino acid sequence of *Solanum lysopersicum* linalool synthase (SEQ ID NO:13).

FIG. 10 provides an amino acid sequence of *Perilla citriodora* linalool synthase (SEQ ID NO:14).

FIG. 11 provides a nucleotide sequence encoding a truncated 3-hydroxy-3-methylglutaryl-coenzyme A reductase (HMGR) (SEQ ID NO: 15).

FIG. 12 provides an amino acid sequence of a truncated HMGR polypeptide (SEQ ID NO:16).

FIG. 13A-13C provide amino acid sequences of wild-type farnesyl diphosphate synthase (FPPS) (FIG. 13A; SEQ ID NO: 17); and two variant FPPS (FIGS. 13B and 13C; SEQ ID NO:18 and SEQ ID NO: 19 respectively).

FIG. 14-17 provide amino acid sequences of geraniol synthase of various species (FIG. 14—SEQ ID NO:20;

FIG. 15—SEQ ID NO:21;

FIG. 16—SEQ ID NO: 22; and

FIG. 17—SEQ ID NO:23).

FIG. 18 provides an amino acid sequence of phosphoribosylaminoimidazole carboxylase (ADE2), a key enzyme in de novo purine synthesis (SEQ ID NO:24).

FIG. 19-21 provide amino acid sequences of various RNA-guided endonucleases, including Cas9 and Cpf1 (FIG. 19—SEQ ID NO:25;

FIG. 20—SEQ ID NO:26; and

FIG. 21—SEQ ID NO:27).

FIG. 27 provides an amino acid sequence of geraniol synthase of Olea europaea (SEQ ID NO:28).

FIG. 28 provides an amino acid sequence of geraniol synthase of Phyla dulcis (SEQ ID NO:29).

FIG. 29 provides an amino acid sequence of geraniol synthase of Vitis vinifera (SEQ ID NO: 30).

FIG. 30 provides an amino acid sequence of geraniol synthase of Ocimum basilicum (SEQ ID NO: 31).

FIG. 36 provides an amino acid sequence of a geraniol reductase (SEQ ID NO:32).

FIG. 37A-37D provide nucleotide sequences of various promoters. FIG. 37A: TDH3—SEQ ID NO:33; ALD6—SEQ ID NO:34; PGK1—SEQ ID NO:35; and TEF1—SEQ ID NO:36, FIG. 37B: TEF2—SEQ ID NO:37; CCW12—SEQ ID NO:38; HHF1—SEQ ID NO:39; and HHF2—SEQ ID NO:40, FIG. 37C: PAB1—SEQ ID NO:41; RPL18b—SEQ ID NO:42; RNR1—SEQ ID NO:43; and RNR2—SEQ ID NO:44, and FIG. 37D: HTB2—SEQ ID NO:45.

FIG. 38 provides a table showing various yeast strains, the promoters driving transcription of nucleic acids encoding tHMGR, ERG20 (F96W/N127W), linalool synthase (LIS), and geraniol synthase (GES), and the amounts of linalool and geraniol produced.

DEFINITIONS

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

Figure 22:
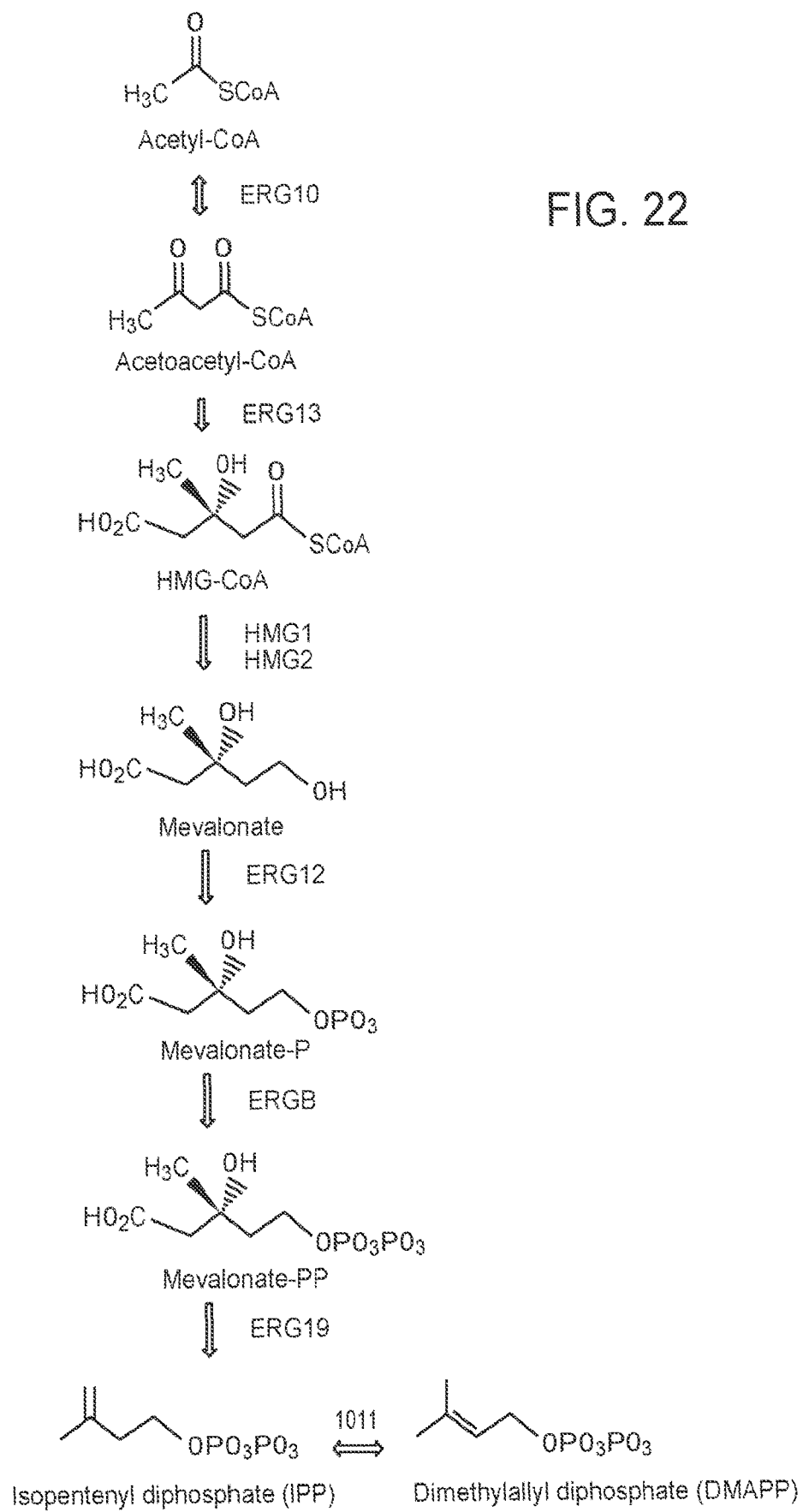
FIG. 22 provides a schematic depiction of a mevalonate pathway.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway is illustrated schematically in FIG. 22.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

The terms "expression vector" or "vector" refer to a nucleic acid that transduces, transforms, or infects a host cell, thereby causing the cell to produce nucleic acids and/or proteins other than those that are native to the cell, or to express nucleic acids and/or proteins in a manner that is not native to the cell.

The term "endogenous" refers to a molecule (e.g., a nucleic acid or a polypeptide) or process that occurs naturally, e.g., in a non-recombinant host cell.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The term "heterologous nucleic acid" as used herein refers to a nucleic acid wherein at least one of the following is true: (a) the nucleic acid is foreign ("exogenous") to (that is, not naturally found in) a given host cell; (b) the nucleic acid comprises a nucleotide sequence that is naturally found in (that is, is "endogenous to") a given host cell, but the nucleotide sequence is produced in an unnatural (for example, greater than expected or greater than naturally found) amount in the cell; (c) the nucleic acid comprises a nucleotide sequence that differs in sequence from an endogenous nucleotide sequence, but the nucleotide sequence encodes the same protein (having the same or substantially the same amino acid sequence) and is produced in an unnatural (for example, greater than expected or greater than naturally found) amount in the cell; or (d) the nucleic acid comprises two or more nucleotide sequences that are not found in the same relationship to each other in nature (for example, the nucleic acid is recombinant).

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

The term "transformation" or "genetic modification" refers to a permanent or transient genetic change induced in a cell following introduction of new nucleic acid. Thus, a "genetically modified host cell" is a host cell into which a new (e.g., exogenous; heterologous) nucleic acid has been introduced. Genetic change ("modification") can be accomplished either by incorporation of the new DNA into the genome of the host cell, or by transient or stable maintenance of the new DNA as an episomal element. In eukaryotic cells, a permanent genetic change is generally achieved by introduction of the DNA into the genome of the cell. In prokaryotic cells, a permanent genetic change can be introduced into the chromosome or via extrachromosomal elements such as plasmids and expression vectors, which may contain one or more selectable markers to aid in their maintenance in the recombinant host cell.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "operably linked" refers to a juxtaposition wherein the components so described are in a relationship permitting them to function in their intended manner. For instance, a promoter is operably linked to a nucleotide sequence if the promoter affects the transcription or expression of the nucleotide sequence.

A "host cell," as used herein, denotes an in vitro eukaryotic cell (e.g., a yeast cell), which eukaryotic cell can be, or has been, used as a recipient for a nucleic acid, and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, sesquiterpenes, triterpenes, polyterpenes, and diterpenes.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/B LAST. See, e.g., Altschul et al. (1990), J. Mol. Biol. 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed.

Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a protein" includes a plurality of such proteins, and so forth.

The term "functional variant" of an enzyme describes an enzyme that has a polypeptide sequence that is at least 70%, 75%, 80%, 85%, 90%, 95% or 99% identical to any one of the enzymes described herein. The "functional variant" enzyme may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity as compared to the enzyme described herein. The "functional variant" enzyme has an enzymatic activity that is identical or essentially identical to the enzymatic activity of the enzyme described herein. The "functional variant" enzyme may be found in nature or be an engineered mutant thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a genetically modified host cell capable of producing a monoterpene. The present disclosure provides a genetically modified host cell capable of producing linalool. The present disclosure provides a genetically modified host cell capable of producing jet fuel, or a precursor of jet fuel. The present disclosure provides a genetically modified host cell capable of producing one or more of linalool, geraniol, and citronellol; such a genetically modified host cell is useful for producing a beverage, e.g., beer.

Production of a Beverage

In the first step of brewing beer, water, grains and hops are used to create a sugar-rich solution called wort. In the second step, the sugars in the wort are fermented by brewers' yeast, *S. cerevisiae*, to produce finished beer. While the grains provide the fermentable sugars in wort, the hops provide the finished beer with desirable flavor and aroma. Monoterpenes are a class of molecules that are present at high concentrations in hop flowers, and are largely responsible for imparting "hoppy" flavor and aroma to beer. In this disclosure, strains of *S. cerevisiae* are described, which produce the monoterpene linalool at levels that are detectable both by taste and smell in finished beer. Ultimately this disclosure could be used to produce a variety of monoterpenes at levels similar to those found in naturally hopped beers, thereby eliminating the need to add hops.

The major technical challenge that was surmounted to reduce this technology to practice was the identification of a gene sequence that, when integrated into a brewing yeast, encodes a linalool synthase capable of producing linalool at concentrations above the flavor detection threshold in finished beer. All linalool synthases reported to date are of plant origin and are expressed in the chloroplast. Plant genes that are targeted to the chloroplast often contain a poorly defined N-terminal amino acid sequence called a plastid targeting sequence (PTS) that directs the newly synthesized protein to the chloroplast. Once the protein is imported into the chloroplast, the PTS is cleaved. Without cleavage, the PTS can destabilize the enzyme and prevent functional heterologous expression. In order to obtain a gene sequence encoding a functional linalool synthase in brewing yeast, various N-terminally truncated gene sequences from six previously reported plant linalool synthases and six previously reported plant geraniol synthases were tested. Introducing an N-terminal truncation was crucial for achieving linalool concentrations above the flavor detection threshold.

There are several major advantages of using yeast fermentation to produce flavor/aroma molecules that are ordinarily derived from hops. 1) Hops make up a substantial portion of the material cost of beer production. Fermentation-based flavor molecule production would therefore reduce the cost of beer production. 2) Because hops are an agricultural product, their flavor molecule composition varies substantially between climates and seasons. Fermentation-based flavor molecule production could therefore reduce variation of flavor and aroma in beer production. 3) Hops are a land and water-intensive crop. Reducing the reliance of beer production on hops would therefore provide key sustainability advantages.

Recombinant methods for manipulations to make the host cell or recombinant nucleic acid of the present invention are described in U.S. Pat. Nos. 5,672,491; 5,843,718; 5,830,750; 5,712,146; and 6,303,342; and in PCT publication nos. WO 98/49315 and WO 97/02358; hereby incorporated by reference.

Figure 3A:
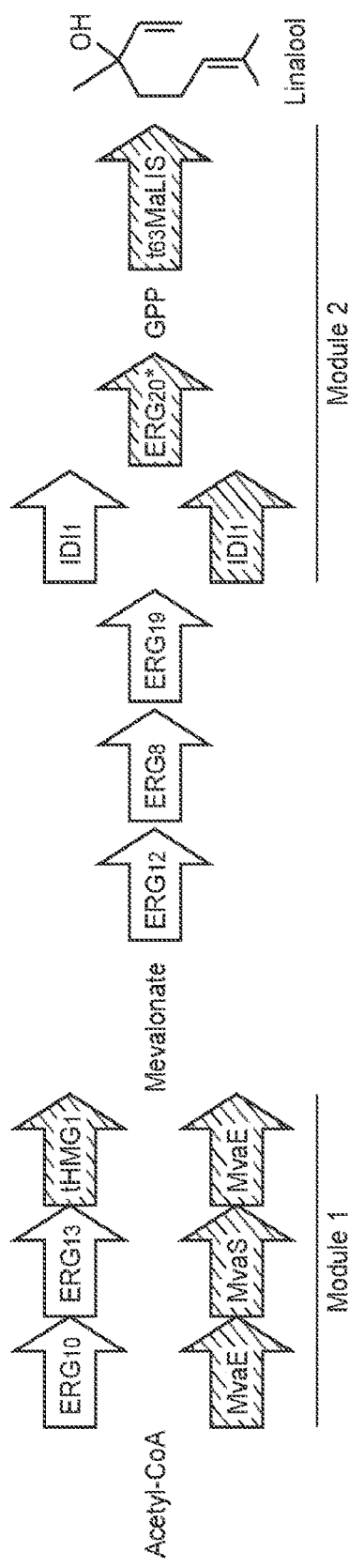
FIG. 3A-3C depicts incorporation of the linalool biosynthesis pathway into Brewer's yeast and testing its effect on linalool production in a brewing yeast during a brewing fermentation.

The present disclosure provides a recombinant nucleic acid that encodes one or more proteins described in FIG. 3A. The recombinant nucleic acid can be a double-stranded or single-stranded DNA, or RNA. The recombinant nucleic acid can encode an open reading frame (ORF) of one or more proteins described in FIG. 3A. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present disclosure. The present invention provides for a host cell comprising any of the recombinant nucleic acid and/or one or more proteins described in FIG. 3A of the present disclosure. In some embodiments, the host cell, when cultured under a suitable condition, is capable of producing the linalool.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The present invention provides a host cell comprising any of the recombinant nucleic acids of the present invention. In some embodiments, the host cell, when cultured, is capable of producing a linalool. The host cell can be a eukaryotic or a prokaryotic cell. Suitable eukaryotic cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable prokaryotic cells include *Escherichia coli* or *Streptomyces* species.

In some embodiments the host cell is a bacterium. Bacterial host cells suitable for practice of the methods of the invention include, but are not limited to, *Escherichia*, *Bacillus*, *Salmonella*, *Klebsiella*, *Enterobacter*, *Pseudomonas*, *Streptomyces*, *Cynechocystis*, *Cynechococcus*, *Sinorhizobium*, and *Caulobacter*, including engineered strains provided by the invention.

Genetically Modified Host Cells

The present disclosure provides a genetically modified host cell that is genetically modified with a heterologous nucleic acid comprising a nucleotide sequence encoding a linalool synthase. A genetically modified host cell of the present disclosure produces linalool. In some cases, the linalool produced by the genetically modified host cell is secreted into the culture medium in which the genetically modified host cell is cultured. In some cases, the genetically modified host cell is a genetically modified yeast cell.

In some cases, a genetically modified host cell of the present disclosure is genetically modified with: a) a heterologous nucleic acid comprising a nucleotide sequence encoding a linalool synthase; and b) a heterologous nucleic acid comprising a nucleotide sequence encoding a geraniol synthase. Such a genetically modified host cell (e.g., a genetically modified yeast cell) produces linalool and geraniol. In some cases, the linalool and the geraniol produced by the genetically modified host cell is secreted into the culture medium in which the genetically modified host cell is cultured. In some cases, the genetically modified host cell is a genetically modified yeast cell.

In some cases, a genetically modified host cell of the present disclosure is genetically modified with: a) a heterologous nucleic acid comprising a nucleotide sequence encoding a linalool synthase; b) a heterologous nucleic acid comprising a nucleotide sequence encoding a geraniol synthase; and c) a heterologous nucleic acid comprising a nucleotide sequence encoding a geraniol reductase, where the nucleotide sequence encoding the geraniol reductase is operably linked to a heterologous promoter. Such a genetically modified host cell (e.g., a genetically modified yeast cell) produces linalool, geraniol, and citronellol. In some cases, the linalool, geraniol, and citronellol produced by the genetically modified host cell is secreted into the culture medium in which the genetically modified host cell is cultured. In some cases, the genetically modified host cell is a genetically modified yeast cell.

By modifying one or both of: a) the copy number of the nucleic acid encoding linalool synthase, geraniol synthase, and geraniol reductase; and b) the promoter strength to which the nucleotide sequences encoding linalool synthase, geraniol synthase, and geraniol reductase are operably linked, the amounts (e.g., the relative amounts) of linalool, geraniol, and citronellol in a beverage can be modified.

Linalool Synthase

In some cases, linalool is produced by a genetically modified host cell of the present disclosure in an amount of from about 0.5 mg per liter (mg/L) of culture medium to about 1.5 mg/L culture medium. For example, in some cases, linalool is produced in an amount of from about 0.5 mg/L to about 0.75 mg/L, from about 0.75 mg/L to about 1.0 mg/L, from about 1.0 mg/L to about 1.25 mg/L, or from about 1.25 mg/L to about 1.5 mg/L culture medium. In some cases, linalool is produced by a genetically modified host cell of the present disclosure in an amount of from about 0.005 mg/L of culture medium to about 5 mg/L culture medium; e.g., from about 0.005 mg/L to about 0.01 mg/L, from about 0.01 mg/L to about 0.05 mg/L, from about 0.05 mg/L to about 0.1 mg/L, from about 0.1 mg/L to about 0.5 mg/L, from about 0.5 mg/L to about 1 mg/L, from about 1 mg/L to about 1.5 mg/L, from about 1.5 mg/L to about 2 mg/L, from about 2.5 mg/L to about 3 mg/L, from about 3 mg/L to about 4 mg/L, or from about 4 mg/L to about 5 mg/L culture medium.

In some cases, linalool is produced by a genetically modified host cell of the present disclosure in an amount of from about 0.5 mg to 10 grams per dry cell weight. In some cases, linalool is produced in an amount of from about 0.5 mg to about 1.0 mg, from 1 mg to 10 mg, from 10 mg to 50 mg, from 50 mg to 100 mg, from 100 mg to 500 mg, from 500 mg to 1 gram, from 1 gram to 5 grams, or from 5 grams to 10 grams, per dry cell weight. In some cases, linalool is produced in an amount of more than 10 grams per dry cell weight.

The linalool synthase can comprise an amino acid sequence having at least 75%, at least 80%, at least 85%, at least 90%, at least 95%, at least 98%, at least 99%, or 100%, amino acid sequence identity to the amino acid sequence depicted in one of FIGS. 4, 5, 6B, and 7-10. The linalool synthase can comprise an amino acid sequence having at least 75%, at least 80%, at least 85%, at least 90%, at least 95%, at least 98%, at least 99%, or 100%, amino acid sequence identity to the amino acid sequence depicted in FIG. 4. The linalool synthase can comprise an amino acid sequence having at least 75%, at least 80%, at least 85%, at least 90%, at least 95%, at least 98%, at least 99%, or 100%, amino acid sequence identity to the amino acid sequence depicted in FIG. 5. The linalool synthase can comprise an amino acid sequence having at least 75%, at least 80%, at least 85%, at least 90%, at least 95%, at least 98%, at least 99%, or 100%, amino acid sequence identity to the amino acid sequence depicted in FIG. 6B. The linalool synthase can comprise an amino acid sequence having at least 75%, at least 80%, at least 85%, at least 90%, at least 95%, at least 98%, at least 99%, or 100%, amino acid sequence identity to the amino acid sequence depicted in FIG. 7. The linalool synthase can comprise an amino acid sequence having at least 75%, at least 80%, at least 85%, at least 90%, at least 95%, at least 98%, at least 99%, or 100%, amino acid sequence identity to the amino acid sequence depicted in FIG. 8. The linalool synthase can comprise an amino acid sequence having at least 75%, at least 80%, at least 85%, at least 90%, at least 95%, at least 98%, at least 99%, or 100%, amino acid sequence identity to the amino acid sequence depicted in FIG. 9. The linalool synthase can comprise an amino acid sequence having at least 75%, at least 80%, at least 85%, at least 90%, at least 95%, at least 98%, at least 99%, or 100%, amino acid sequence identity to the amino acid sequence depicted in FIG. 10.

The linalool synthase can have a length of from 500 amino acids to 600 amino acids. The linalool synthase can have a length of from 530 amino acids to 550 amino acids. The linalool synthase can have a length of 540 amino acids.

The linalool synthase lacks a plastid targeting sequence (PTS). In plants, the PTS directs a newly synthesized protein to the chloroplast. For example, in the linalool synthase amino acid sequences depicted in FIG. 5, the PTS is from amino acid 1 to amino acid 67. Thus, a linalool synthase produced by a genetically modified host cell of the present disclosure can comprise an amino acid sequence having at least 75%, at least 80%, at least 85%, at least 90%, at least 95%, at least 98%, at least 99%, or 100%, amino acid sequence identity to amino acids 68-606 of the amino acid sequence depicted in FIG. 5. An N-terminal methionine can be added to the amino acid sequence. As another example, a linalool synthase produced by a genetically modified host cell of the present disclosure can comprise an amino acid sequence having at least 75%, at least 80%, at least 85%, at least 90%, at least 95%, at least 98%, at least 99%, or 100%, amino acid sequence identity to amino acids 56-595 of the amino acid sequence depicted in FIG. 7. An N-terminal methionine can be added to the amino acid sequence. As another example, a linalool synthase produced by a genetically modified host cell of the present disclosure can comprise an amino acid sequence having at least 75%, at least 80%, at least 85%, at least 90%, at least 95%, at least 98%, at least 99%, or 100%, amino acid sequence identity to amino acids 62-607 of the amino acid sequence depicted in FIG. 8. An N-terminal methionine can be added to the amino acid sequence. As another example, a linalool synthase produced by a genetically modified host cell of the present disclosure can comprise an amino acid sequence having at least 75%, at least 80%, at least 85%, at least 90%, at least 95%, at least 98%, at least 99%, or 100%, amino acid sequence identity to amino acids 44-609 of the amino acid sequence depicted in FIG. 9. An N-terminal methionine can be added to the amino acid sequence. As another example, a linalool synthase produced by a genetically modified host cell of the present disclosure can comprise an amino acid sequence having at least 75%, at least 80%, at least 85%, at least 90%, at least 95%, at least 98%, at least 99%, or 100%, amino acid sequence identity to amino acids 69-602 of the amino acid sequence depicted in FIG. 10. An N-terminal methionine can be added to the amino acid sequence.

The amino acid sequence depicted in FIG. 6B lacks a PTS. Thus, a linalool synthase produced by a genetically modified host cell of the present disclosure can comprise an amino acid sequence having at least 75%, at least 80%, at least 85%, at least 90%, at least 95%, at least 98%, at least 99%, or 100%, amino acid sequence identity to the amino acid sequence depicted in FIG. 6B.

In some cases, the nucleotide sequence encoding the linalool synthase is operably linked to a transcriptional control element that is functional in the host cell. For example, in some cases, the nucleotide sequence encoding the linalool synthase is operably linked to a transcriptional control element that is functional a yeast cell. In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein in: DNA Cloning Vol. 11, A Practical Approach, Ed. DM Glover, 1986, IRL Press, Wash., D.C.). Alternatively, vectors may be used which promote integration of foreign DNA sequences into the yeast chromosome. Another suitable promoter is a GAL10 promoter. Other suitable promoters include, e.g., a THD3 promoter, an ALD6 promoter, a PGK1 promoter, a TEF1 promoter, a TEF2 promoter, a CCW12 promoter, an HHF1 promoter, an HHF2 promoter, a PAB2 promoter, an RPL18b promoter, an RNR1 promoter, an RNR2 promoter, or an HTB2 promoter. Nucleotide sequences of various suitable promoters are provided in FIG. 37A-37D.

The present disclosure provides a recombinant expression vector comprising a nucleic acid comprising a nucleotide sequence encoding a linalool synthase. Suitable expression vectors that can be used to generate a recombinant expression vector comprising a nucleic acid comprising a nucleotide sequence encoding a linalool synthase are known in the art. In some cases, the expression vector is a high copy number vector (e.g., more than 10 copies per cell, more than 25 copies per cell, more than 50 copies per cell, more than 100 copies per cell). In some cases, the expression vector is a medium copy number vector (e.g., from 5 to 50, from 5 to 25, or from 5 to 10 copies per cell). In some cases, the expression vector is a low copy number vector (e.g., from 2 to 20, from 2 to 15, from 2 to 10, or from 2 to 5, copies per cell). In some cases, the expression vector is a single copy vector. The 2-micron plasmid is an example of a high copy number plasmid; others are known in the art. In some cases, the expression vector integrates into the genome of a host cell. In some cases, the expression vector is maintained episomally. Suitable yeast vectors include yeast integrating plasmids, yeast replicating plasmids, yeast centromere plasmids, and yeast episomal plasmids.

Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like.

In some cases, the genetically modified host cell is a yeast cell. Suitable host cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable host cells include, *Saccharomyces aceti*, *Saccharomyces capensis*, *Saccharomyces chevalieri*, *Saccharomyces coreanus*, *Saccharomyces globosus*, *Saccharomyces norbensis*, *Saccharomyces servazzii*, *Saccharomyces telluris*, *Saccharomyces unisporus*, and the like.

Where a genetically modified host cell of the present disclosure is a yeast cell, in some cases, the yeast cell is haploid.

Where a genetically modified host cell of the present disclosure is a yeast cell, in some cases, the yeast cell is diploid. In some of these embodiments, the nucleotide sequence encoding linalool synthase is integrated into both copies of the genome.

Where a genetically modified host cell of the present disclosure is a yeast cell, in some cases, the yeast cell is tetraploid. In some of these embodiments, the nucleotide sequence encoding linalool synthase is integrated into all four copies of the genome.

A subject genetically modified host cell is generated using standard methods well known to those skilled in the art. In some cases, a nucleic acid comprising a nucleotide sequence encoding a linalool synthase is introduced into the genome of a host cell using a CRISPR/Cas9 system comprising: i) an RNA-guided endonuclease; ii) a guide RNA (e.g., a single molecule guide RNA; or a double-molecule guide RNA); and iii) a donor DNA template. Suitable RNA-guided endonucleases include an RNA-guided endonuclease comprising an amino acid sequence having at least 85%, at least 90%, at least 95%, at least 98%, at least 99%, or 100%, amino acid sequence identity to the amino acid sequence depicted in one of FIGS. 19, 20, and 21. The guide RNA comprises a targeting sequence. A suitable targeting sequence can be determined by those skilled in the art. The donor template comprises a nucleotide sequence complementary to a linalool synthase-encoding nucleotide sequence.

Figure 25:
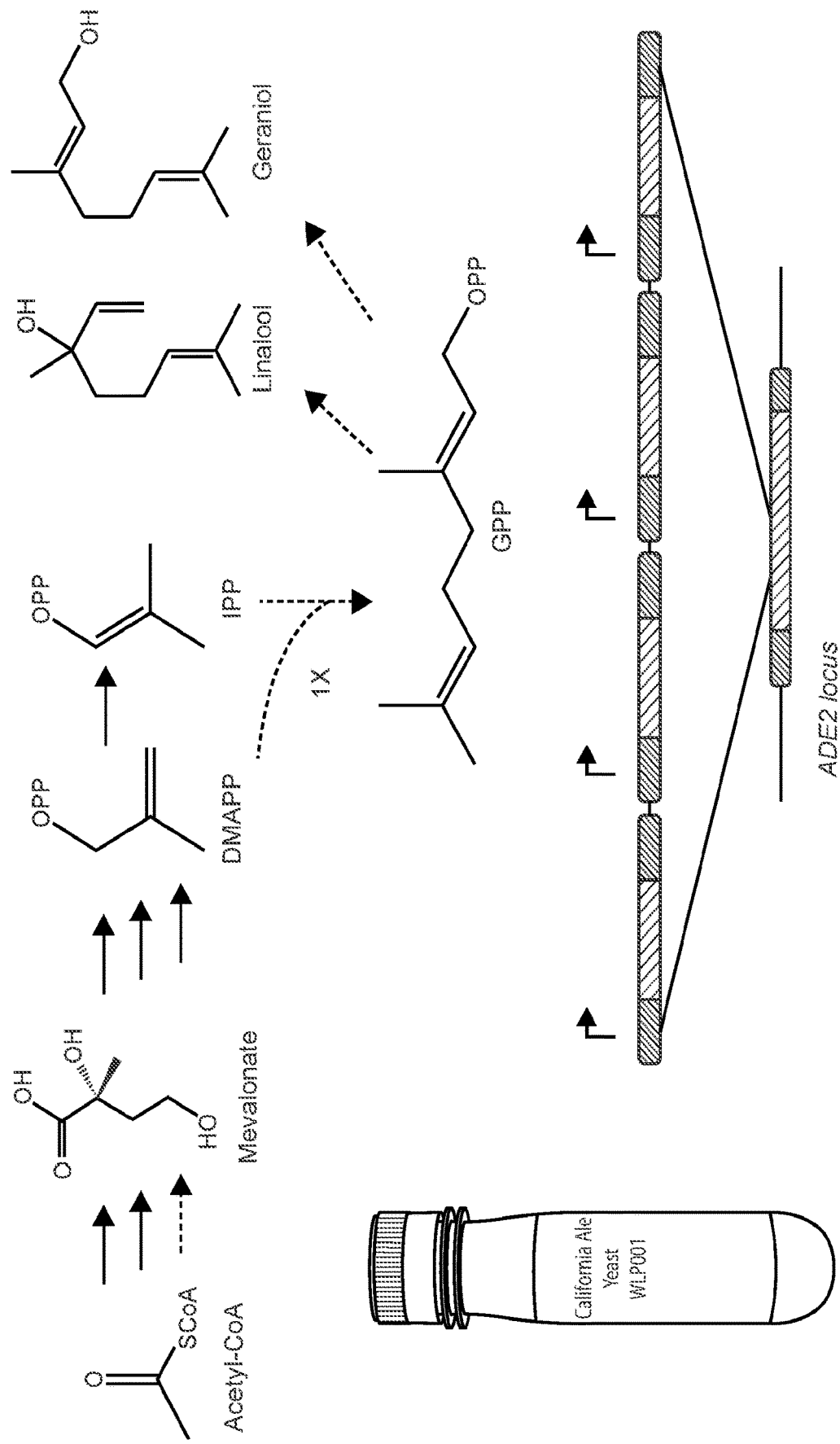
FIG. 25 schematically depicts genetically modifying a yeast strain for beer fermentation.

FIG. 25 schematically depicts a method for modifying the genome of a host yeast cell to include nucleic acids encoding linalool and geraniol. In some cases, a CRISPR/Cas9 system comprising: i) an RNA-guided endonuclease; and ii) guide RNAs that provide for deletion of an endogenous phosphoribosylaminoimidazole carboxylase (ADE2) gene are used to delete the ADE2 gene in a host yeast cell. Deletion of the ADE2 gene in a host yeast cell (e.g., *S. cerevisiae*) results in ADE2$^-$ cells that are readily identified by their red color. In some cases, all copies of the ADE2 gene are deleted, generating an ADE2$^-$ host cell. A CRISPR/Cas9 system comprising: i) an RNA-guided endonuclease; ii) a guide RNA (e.g., a single molecule guide RNA; or a double-molecule guide RNA); and iii) a donor DNA template comprising nucleotide sequences encoding ADE2 and linalool synthase is used to generate a genetically modified host cell that is genetically modified with a nucleic acid comprising a nucleotide sequence encoding linalool synthase. The CRISPR/Cas9 system comprising: i) an RNA-guided endonuclease; ii) a guide RNA (e.g., a single molecule guide RNA; or a double-molecule guide RNA); and iii) a donor DNA template comprising nucleotide sequences encoding ADE2 and linalool synthase is introduced into the ADE2$^-$ host cell, to generate genetically modified host cells that are ADE2$^+$ and that are genetically modified with a nucleic acid comprising a nucleotide sequence encoding linalool synthase. Genetically modified host cells that are ADE2$^+$ and that are genetically modified with a nucleic acid comprising a nucleotide sequence encoding linalool synthase are identified by lack of red color (e.g., they form normal colored colonies).

Mevalonate Pathway Enzymes

The mevalonate pathway comprises enzymes that catalyze the following steps: (a) condensing two molecules of acetyl-CoA to acetoacetyl-CoA, typically by action of acetoacetyl-CoA thiolase (e.g., ERG10 in yeast); (b) condensing acetoacetyl-CoA with acetyl-CoA to form HMG-CoA, typically by action of HMG synthase (HMGS) (e.g., ERG13 in yeast); (c) converting HMG-CoA to mevalonate, typically by action of HMG-CoA reductase (HMGR); (d) phosphorylating mevalonate to mevalonate 5-phosphate, typically by action of mevalonate kinase (MK) (e.g., ERG12 in yeast); (e) converting mevalonate 5-phosphate to mevalonate 5-pyrophosphate, typically by action of phosphomevalonate kinase (PMK) (e.g., ERG8 in yeast); and (f) converting mevalonate 5-pyrophosphate to isopentenyl pyrophosphate (IPP), typically by action of mevalonate pyrophosphate decarboxylase (MPD) (e.g., ERG19 in yeast). IPP is isomerized to dimethylallyl-pyrophosphate (DMAPP) by the action of isopentenyl diphosphate:dimethylallyl diphosphate isomerase (IDI1). These reactions are depicted schematically in FIG. 22. IPP and DMAPP are condensed to form geranyl diphosphate (GPP) and subsequently farnesyl diphosphate (FPP) by the action of farnesyl diphosphate synthase (FPPS) (e.g., ERG20 in yeast). GPP can then be catalytically modified to produce monoterpenes, such as linalool, by action of linalool synthase. GPP can also be modified to produce geraniol, by action of geraniol synthase. These reactions are depicted schematically in FIG. 24.

The enzyme HMG-CoA reductase (HMGR) catalyzes an irreversible reaction that reduces 3-hydroxy-3-methylglutaryl Coenzyme A (HMG-CoA) to mevalonate. In some cases, a genetically modified host cell of the present disclosure is genetically modified such that the HMGR is truncated. For example, in some cases, a genetically modified host cell of the present disclosure is genetically modified with a nucleic acid comprising a nucleotide sequence encoding a truncated HMGR (tHMGR). In some cases, the tHMGR comprises an amino acid sequence having at least 85%, at least 90%, at least 95%, at least 98%, at least 99%, or 100%, amino acid sequence identity to the tHMGR amino acid sequence depicted in FIG. 12. The tHMGR can have a length of about 502 amino acids.

In some cases, a genetically modified host cell of the present disclosure comprises a first "module" (operon or single transcription unit) that comprises nucleotide sequences encoding ERG10, ERG13, and tHMGR; a second "module" (operon or single transcription unit) that comprises nucleotide sequences encoding ERG12, ERG8, and ERG19; and a third "module" (operon or single transcription unit) that comprises nucleotide sequences encoding IDI1 and ERG20; and a nucleic acid comprising a nucleotide sequence encoding linalool synthase. In some cases, the ERG10, ERG13, ERG12, ERG8, ERG19, and IDI1 are all endogenous nucleotide sequences. In some cases, the FPPS is modified, as described below, to increase the GPP:FPP ratio.

The enzyme farnesyl diphosphate synthase (FPPS) catalyzes a reaction that converts geranyl diphosphate (GPP) into farnesyl diphosphate (FPP). In some cases, a genetically modified host cell of the present disclosure is genetically modified such that the FPPS comprises one or more amino acid substitutions that provide for an increased ratio of GPP:FPP produced by the genetically modified host cell. Thus, for example, in some cases, a genetically modified host cell of the present disclosure is genetically modified such that the FPPS comprises one or more amino acid substitutions that provide for a GPP:FPP ratio of from 65:55 to 90:10, e.g., from 65:55 to 60:40, from 60:40 to 70:30, from 70:30 to 80:20, or from 90:10. In some cases, a genetically modified host cell of the present disclosure is genetically modified with an exogenous nucleic acid comprising a nucleotide sequence encoding an FPPS comprising one or more amino acid substitutions at positions selected from F96, N127, and K197, relative to the amino acid sequence depicted in FIG. 13A. In some cases, a genetically modified host cell of the present disclosure is genetically modified such that the endogenous FPPS is modified to comprise one or more amino acid substitutions at positions selected from F96, N127, and K197, relative to the amino acid sequence depicted in FIG. 13A. In some cases, the modified FPPS comprises an amino acid sequence having at least 85%, at least 90%, at least 95%, at least 98%, at least 99%, amino acid sequence identity to the FPPS amino acid sequence depicted in FIG. 13B, and comprises an F96W substitution and an N127W substitution. In some cases, the modified FPPS comprises the amino acid sequence depicted in FIG. 13B. In some cases, the modified FPPS comprises an amino acid sequence having at least 85%, at least 90%, at least 95%, at least 98%, or at least 99%, amino acid sequence identity to the FPPS amino acid sequence depicted in FIG. 13C, and comprises a K197E substitution. In some cases, the modified FPPS comprises the amino acid sequence depicted in FIG. 13C.

Geraniol Synthase

In some cases, a genetically modified host cell of the present disclosure is genetically modified with a heterologous nucleic acid comprising a nucleotide sequence encoding a geraniol synthase. Thus, in some cases, a genetically modified host cell of the present disclosure is genetically modified with one or more heterologous nucleic acids comprising nucleotide sequences encoding linalool synthase and geraniol synthase. In some cases, the geraniol synthase comprises an amino acid sequence having at least 75%, at least 85%, at least 90%, at least 95%, at least 98%, at least 99%, or 100%, amino acid sequence identity to the geraniol synthase depicted in any one of FIG. 14-17 and FIG. 27-30.

In some cases, a genetically modified host cell of the present disclosure is genetically modified with: a) a heterologous nucleic acid comprising a nucleotide sequence encoding a linalool synthase; and b) a heterologous nucleic acid comprising a nucleotide sequence encoding a geraniol synthase. Such a genetically modified host cell (e.g., a genetically modified yeast cell) produces linalool and geraniol. In some cases, the linalool and the geraniol produced by the genetically modified host cell is secreted into the culture medium in which the genetically modified host cell is cultured. In some cases, the genetically modified host cell is a genetically modified yeast cell.

In some cases, geraniol is produced by a genetically modified host cell of the present disclosure in an amount of from about 0.5 mg per liter (mg/L) of culture medium to about 1.5 mg/L culture medium. For example, in some cases, geraniol is produced in an amount of from about 0.5 mg/L to about 0.75 mg/L, from about 0.75 mg/L to about 1.0 mg/L, from about 1.0 mg/L to about 1.25 mg/L, or from about 1.25 mg/L to about 1.5 mg/L culture medium. In some cases, geraniol is produced by a genetically modified host cell of the present disclosure in an amount of from about 0.005 mg/L of culture medium to about 5 mg/L culture medium; e.g., from about 0.005 mg/L to about 0.01 mg/L, from about 0.01 mg/L to about 0.05 mg/L, from about 0.05 mg/L to about 0.1 mg/L, from about 0.1 mg/L to about 0.5 mg/L, from about 0.5 mg/L to about 1 mg/L, from about 1 mg/L to about 1.5 mg/L, from about 1.5 mg/L to about 2 mg/L, from about 2.5 mg/L to about 3 mg/L, from about 3 mg/L to about 4 mg/L, or from about 4 mg/L to about 5 mg/L culture medium.

In some cases, geraniol is produced by a genetically modified host cell of the present disclosure in an amount of from about 0.5 mg to 10 grams per dry cell weight. In some cases, geraniol is produced in an amount of from about 0.5 mg to about 1.0 mg, from 1 mg to 10 mg, from 10 mg to 50 mg, from 50 mg to 100 mg, from 100 mg to 500 mg, from 500 mg to 1 gram, from 1 gram to 5 grams, or from 5 grams to 10 grams, per dry cell weight. In some cases, geraniol is produced in an amount of more than 10 grams per dry cell weight.

Where a genetically modified host cell of the present disclosure is a yeast cell, in some cases, the yeast cell is haploid.

Where a genetically modified host cell of the present disclosure is a yeast cell, in some cases, the yeast cell is diploid. In some of these embodiments, the nucleotide sequence encoding geraniol synthase is integrated into both copies of the genome.

Where a genetically modified host cell of the present disclosure is a yeast cell, in some cases, the yeast cell is tetraploid. In some of these embodiments, the nucleotide sequence encoding geraniol synthase is integrated into all four copies of the genome.

In some cases, the encoded geraniol synthase lacks a PTS. For example, in some cases, a suitable geraniol synthase comprises an amino acid sequence having at least 75%, at least 85%, at least 90%, at least 95%, at least 98%, at least 99%, or 100%, amino acid sequence identity to amino acids 26-603 of the amino acid sequence depicted in FIG. 14; and has a length of about 578 amino acids; where the geraniol synthase does not include the PTS of amino acids 1-25 of the amino acid sequence depicted in FIG. 14.

As another example, a suitable geraniol synthase comprises an amino acid sequence having at least 75%, at least 85%, at least 90%, at least 95%, at least 98%, at least 99%, or 100%, amino acid sequence identity to amino acids 26-603 of the amino acid sequence depicted in FIG. 15; and has a length of about 578 amino acids; where the geraniol synthase does not include the PTS of amino acids 1-25 of the amino acid sequence depicted in FIG. 15.

As another example, a suitable geraniol synthase comprises an amino acid sequence having at least 75%, at least 85%, at least 90%, at least 95%, at least 98%, at least 99%, or 100%, amino acid sequence identity to amino acids 53-612 of the amino acid sequence depicted in FIG. 17; and has a length of about 560 amino acids; where the geraniol synthase does not include the PTS of amino acids 1-52 of the amino acid sequence depicted in FIG. 17.

As another example, a suitable geraniol synthase comprises an amino acid sequence having at least 75%, at least 85%, at least 90%, at least 95%, at least 98%, at least 99%, or 100%, amino acid sequence identity to amino acids 92-583 of the amino acid sequence depicted in FIG. 27; and has a length of about 492 amino acids; where the geraniol synthase does not include the PTS of amino acids 1-91 of the amino acid sequence depicted in FIG. 27.

As another example, a suitable geraniol synthase comprises an amino acid sequence having at least 75%, at least 85%, at least 90%, at least 95%, at least 98%, at least 99%, or 100%, amino acid sequence identity to amino acids 87-584 of the amino acid sequence depicted in FIG. 28; and has a length of about 498 amino acids; where the geraniol synthase does not include the PTS of amino acids 1-86 of the amino acid sequence depicted in FIG. 28.

As another example, a suitable geraniol synthase comprises an amino acid sequence having at least 75%, at least 85%, at least 90%, at least 95%, at least 98%, at least 99%, or 100%, amino acid sequence identity to amino acids 83-595 of the amino acid sequence depicted in FIG. 29; and has a length of about 513 amino acids; where the geraniol synthase does not include the PTS of amino acids 1-82 of the amino acid sequence depicted in FIG. 29.

As another example, a suitable geraniol synthase comprises an amino acid sequence having at least 75%, at least 85%, at least 90%, at least 95%, at least 98%, at least 99%, or 100%, amino acid sequence identity to amino acids 73-567 of the amino acid sequence depicted in FIG. 30; and has a length of about 495 amino acids; where the geraniol synthase does not include the PTS of amino acids 1-72 of the amino acid sequence depicted in FIG. 30.

In some cases, the nucleotide sequence encoding a geraniol synthase is operably linked to a promoter that is functional in a yeast cell. In some cases the promoter is a Galactose-inducible promoter. In some cases, the promoter is a GAL1 promoter, a GAL10 promoter, or a ERG20 promoter. Other suitable promoters include, e.g., a THD3 promoter, an ALD6 promoter, a PGK1 promoter, a TEF1 promoter, a TEF2 promoter, a CCW12 promoter, an HHF1 promoter, an HHF2 promoter, a PAB2 promoter, an RPL18b promoter, an RNR1 promoter, an RNR2 promoter, or an HTB2 promoter. Nucleotide sequences of various suitable promoters are provided in FIG. 37A-37D.

In some cases, a genetically modified host cell of the present disclosure is genetically modified with: a) a heterologous nucleic acid comprising a nucleotide sequence encoding a linalool synthase; and b) a heterologous nucleic acid comprising a nucleotide sequence encoding a geraniol synthase. In some cases, the nucleotide sequence encoding the linalool synthase and the nucleotide sequence encoding the geraniol synthase are operably linked to the same promoter. In some cases, the nucleotide sequence encoding the linalool synthase and the nucleotide sequence encoding the geraniol synthase are operably linked to two different promoters. In some cases, the nucleotide sequence encoding the linalool synthase is operably linked to a first promoter; and the nucleotide sequence encoding the geraniol synthase is operably linked to a second promoter, where the first promoter is a stronger promoter than the second promoter. In some cases, the nucleotide sequence encoding the linalool synthase is operably linked to a first promoter; and the nucleotide sequence encoding the geraniol synthase is operably linked to a second promoter, where the second promoter is a stronger promoter than the first promoter. In some cases, the nucleotide sequence encoding the linalool synthase is operably linked to a first promoter; and the nucleotide sequence encoding the geraniol synthase is operably linked to a second promoter, where the first promoter and the second promoter are of substantially equal strength.

The following are non-limiting examples. In some cases, the nucleotide sequence encoding the linalool synthase is operably linked to an HHF2 promoter; and the nucleotide sequence encoding the geraniol synthase is operably linked to an HTB2 promoter. The following are non-limiting examples. In some cases, the nucleotide sequence encoding the linalool synthase is operably linked to a TEF2 promoter; and the nucleotide sequence encoding the geraniol synthase is operably linked to an HHF2 promoter. In some cases, the nucleotide sequence encoding the linalool synthase is operably linked to an RPL18b promoter; and the nucleotide sequence encoding the geraniol synthase is operably linked to a TDH3 promoter. In some cases, the nucleotide sequence encoding the linalool synthase is operably linked to an RPL18b promoter; and the nucleotide sequence encoding the geraniol synthase is operably linked to a CCW12 promoter. In some cases, the nucleotide sequence encoding the linalool synthase is operably linked to a TEF1 promoter; and the nucleotide sequence encoding the geraniol synthase is operably linked to a TEF2 promoter. Other combinations of promoters are possible. Examples of promoter combinations driving expression of linalool synthase-encoding (trnc67-McLIS) and geraniol synthase-encoding (ObGES) nucleic acids are depicted in FIG. 38.

In some cases, a genetically modified host cell of the present disclosure is genetically modified with a single recombinant expression vector comprising: a) a heterologous nucleic acid comprising a nucleotide sequence encoding a linalool synthase; and b) a heterologous nucleic acid comprising a nucleotide sequence encoding a geraniol synthase. In some cases, the recombinant expression vector is a high copy number vector. In some cases, the recombinant expression vector is a medium copy number vector. In some cases, the recombinant expression vector is a low copy number vector. In some cases, the recombinant expression vector is a single copy vector.

In some cases, a genetically modified host cell of the present disclosure is genetically modified with: a) a first recombinant expression vector comprising a heterologous nucleic acid comprising a nucleotide sequence encoding a linalool synthase; and b) a second recombinant expression vector comprising a heterologous nucleic acid comprising a nucleotide sequence encoding a geraniol synthase. In some cases, the first recombinant expression vector is a high copy number vector; and the second recombinant expression vector is a high copy number vector. In some cases, the first recombinant expression vector is a high copy number vector; and the second recombinant expression vector is a low copy number vector. In some cases, the first recombinant expression vector is a high copy number vector; and the second recombinant expression vector is a medium copy number vector. In some cases, the first recombinant expression vector is a high copy number vector; and the second recombinant expression vector is a single copy vector. In some cases, the first recombinant expression vector is a low copy number vector; and the second recombinant expression vector is a high copy number vector. In some cases, the first recombinant expression vector is a medium copy number vector; and the second recombinant expression vector is a high copy number vector. In some cases, the first recombinant expression vector is a single copy vector; and the second recombinant expression vector is a high copy number vector. In some cases, the first recombinant expression vector is a single copy vector; and the second recombinant expression vector is a medium copy number vector. In some cases, the first recombinant expression vector is a single copy vector; and the second recombinant expression vector is a low copy number vector. In some cases, the first recombinant expression vector is a single copy vector; and the second recombinant expression vector is a single copy vector.

In some cases, a genetically modified host cell of the present disclosure comprises a first "module" (operon or single transcription unit) that comprises nucleotide sequences encoding ERG10, ERG13, and tHMGR; a second "module" (operon or single transcription unit) that comprises nucleotide sequences encoding ERG12, ERG8, and ERG19; and a third "module" (operon or single transcription unit) that comprises nucleotide sequences encoding IDI1 and ERG20; and one or more nucleic acids comprising nucleotide sequence encoding linalool synthase and geraniol synthase. In some cases, the ERG10, ERG13, ERG12, ERG8, ERG19, and IDI1 are all endogenous nucleotide sequences. In some cases, the FPPS is modified, as described above, to increase the GPP:FPP ratio.

In some cases, where a genetically modified host cell of the present disclosure is genetically modified with one or more heterologous nucleic acids comprising nucleotide sequences encoding linalool synthase and geraniol synthase, the genetically modified host cell produces linalool and geraniol. In some cases: a) linalool is produced by a genetically modified host cell of the present disclosure in an amount of from about 0.5 mg per liter (mg/L) of culture medium to about 1.5 mg/L culture medium (e.g., in some cases, linalool is produced in an amount of from about 0.5 mg/L to about 0.75 mg/L, from about 0.75 mg/L to about 1.0 mg/L, from about 1.0 mg/L to about 1.25 mg/L, or from about 1.25 mg/L to about 1.5 mg/L culture medium); and b) geraniol is produced by the genetically modified host cell in an amount of from about 0.75 mg/L to about 2.0 mg/L culture medium (e.g., in some cases, linalool is produced in an amount of from about 0.75 mg/L to about 1.0 mg/L, from about 1.0 mg/L to about 1.25 mg/L, from about 1.25 mg/L to about 1.5 mg/L, from about 1.5 mg/L to about 1.75 mg/L, or from about 1.75 mg/L to about 2.0 mg/L culture medium).

In some cases: a) linalool is produced by a genetically modified host cell of the present disclosure in an amount of from about 0.005 mg/L of culture medium to about 5 mg/L culture medium; e.g., from about 0.005 mg/L to about 0.01 mg/L, from about 0.01 mg/L to about 0.05 mg/L, from about 0.05 mg/L to about 0.1 mg/L, from about 0.1 mg/L to about 0.5 mg/L, from about 0.5 mg/L to about 1 mg/L, from about 1 mg/L to about 1.5 mg/L, from about 1.5 mg/L to about 2 mg/L, from about 2.5 mg/L to about 3 mg/L, from about 3 mg/L to about 4 mg/L, or from about 4 mg/L to about 5 mg/L culture medium; and b) geraniol is produced by a genetically modified host cell of the present disclosure in an amount of from about 0.005 mg/L of culture medium to about 5 mg/L culture medium; e.g., from about 0.005 mg/L to about 0.01 mg/L, from about 0.01 mg/L to about 0.05 mg/L, from about 0.05 mg/L to about 0.1 mg/L, from about 0.1 mg/L to about 0.5 mg/L, from about 0.5 mg/L to about 1 mg/L, from about 1 mg/L to about 1.5 mg/L, from about 1.5 mg/L to about 2 mg/L, from about 2.5 mg/L to about 3 mg/L, from about 3 mg/L to about 4 mg/L, or from about 4 mg/L to about 5 mg/L culture medium.

Citronellol Synthase

In some cases, a genetically modified host cell of the present disclosure is genetically modified with a heterologous nucleic acid comprising a nucleotide sequence encoding a citronellol synthase. In some cases, an endogenous old yellow enzyme 2 (OYE2) gene encodes a reductase (OYE2) that converts geraniol to citronellol. Thus, in some cases, a genetically modified host cell of the present disclosure is genetically modified with a heterologous nucleic acid comprising a nucleotide sequence encoding OYE2. A suitable OYE2 polypeptide comprises an amino acid sequence having at least about 75%, at least 85%, at least 90%, at least 95%, at least 98%, at least 99%, or 100%, amino acid sequence identity to the OYE2 amino acid sequence depicted in FIG. 36.

In some cases, the nucleotide sequence encoding the OYE2 polypeptide is operably linked to an endogenous OYE2 promoter. In some cases, the nucleotide sequence encoding the OYE2 polypeptide is operably linked to a heterologous promoter. In some cases, the OYE2 polypeptide is operably linked to a promoter that is functional in a yeast cell. In some cases, the promoter can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. In some cases, the promoter can be a GAL-inducible promoter. Other useful promoters for yeast host cells are described by Romanos et al., 1992, Yeast 8:423-488. Further disclosure related to OYE2 promoters can be found in U.S. Pat. No. 9,121,045; the disclosure of which is incorporated herein by reference in its entirety. Other suitable promoters include, e.g., a THD3 promoter, an ALD6 promoter, a PGK1 promoter, a TEF1 promoter, a TEF2 promoter, a CCW12 promoter, an HHF1 promoter, an HHF2 promoter, a PAB2 promoter, an RPL18b promoter, an RNR1 promoter, an RNR2 promoter, or an HTB2 promoter. Nucleotide sequences of various suitable promoters are provided in FIG. 37A-37D.

Where a genetically modified host cell of the present disclosure is a yeast cell, in some cases, the yeast cell is diploid. In some of these embodiments, the nucleotide sequences encoding linalool synthase and geraniol synthase are integrated into both copies of the genome.

Where a genetically modified host cell of the present disclosure is a yeast cell, in some cases, the yeast cell is tetraploid. In some of these embodiments, the nucleotide sequences encoding linalool synthase and geraniol synthase are integrated into all four copies of the genome.

Compositions

The present disclosure provides a composition comprising: a) a genetically modified host cell of the present disclosure; and b) a culture medium. The culture medium typically comprises a carbon source. In some cases, the composition comprises sugars derived from barley.

Methods of Producing Fermented Beverages

The present disclosure provides a method of producing a fermented beverage or a beverage precursor, the method comprising culturing a composition for a time period and under conditions suitable for fermentation, where the composition comprises: a) a genetically modified host cell of the present disclosure; and b) a culture medium; and separating the genetically modified host cell from the culture medium, to generate a fermented liquid. Separating the genetically modified host cell(s) from the culture medium can be accomplished by methods known in the art, such as centrifugation, filtration, and the like.

The fermented liquid can be used as is, or can be further processed. If the fermented liquid is to be further processed, it can be referred to as a "beverage precursor."

The culture medium comprises a carbon source. In some cases, the culture medium comprises sugars derived from barley. In some cases, the culture medium comprises sugars derived from rye. In some cases, the culture medium comprises malt. In some cases, the culture medium comprises molasses. In some cases, the culture medium comprises caramelized sugar. In some cases, the culture medium comprises sugarcane juice.

Figure 23:
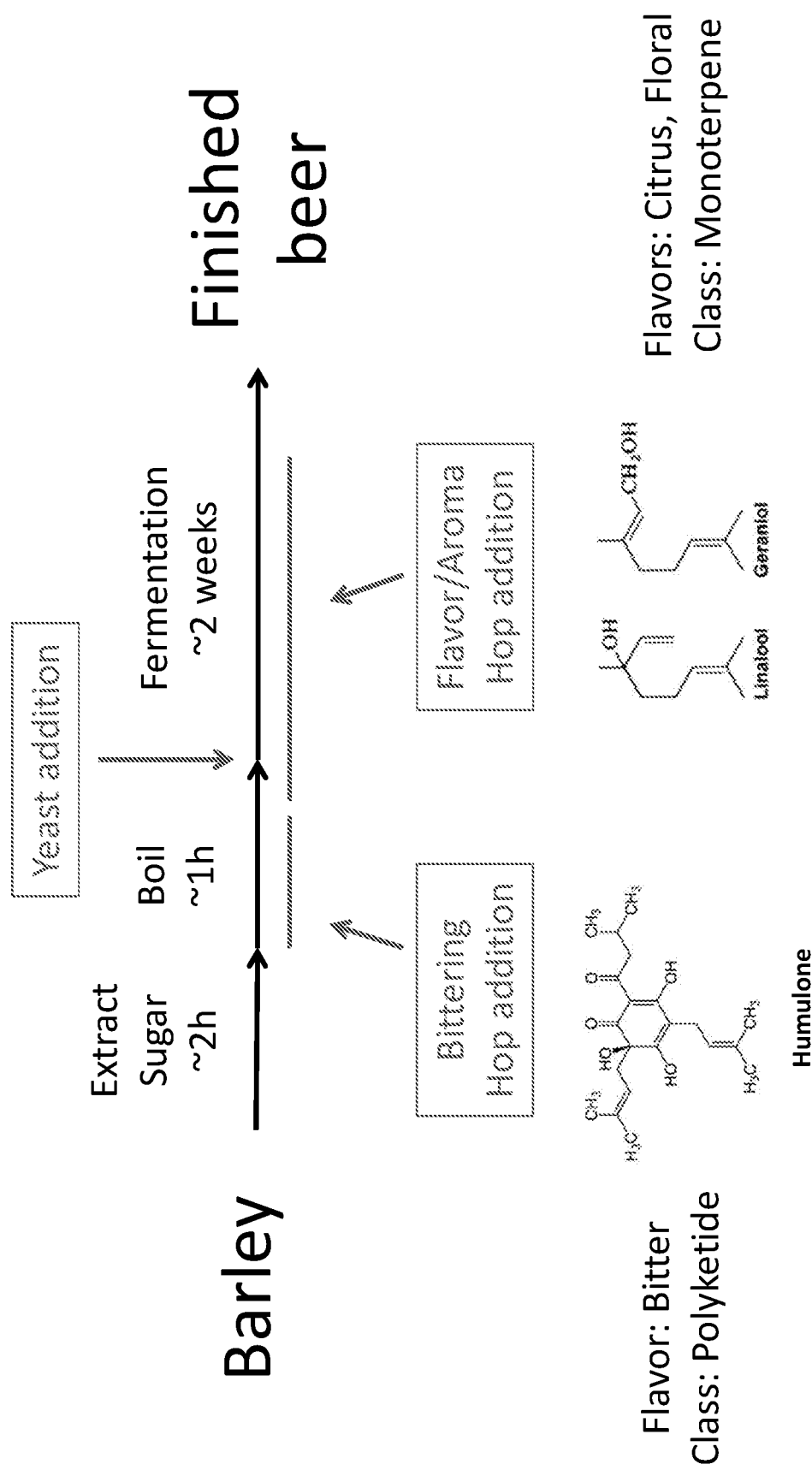
FIG. 23 schematically depicts production of beer.

The present disclosure provides a fermented beverage generated by the method. In some cases, the fermented beverage is beer. In the present disclosure, beer is made by fermenting a malt extract (e.g., a barley malt extract) with a genetically modified yeast cell of the present disclosure; no flavoring or any other involvement with hops is required or used. Thus, unlike traditional beer brewing processes (e.g., as depicted in FIG. 23), no hops are used in a method of the present disclosure for producing a fermented beverage such as beer.

In some cases, a fermented beverage is made by fermenting a liquid comprising a barley syrup with a genetically modified yeast cell of the present disclosure. In some cases, a fermented beverage is made by fermenting a liquid comprising unmalted barley with a genetically modified yeast cell of the present disclosure. In some cases, a fermented beverage is made by fermenting a liquid comprising wort with a genetically modified yeast cell of the present disclosure. In some cases, a fermented beverage is made by fermenting a liquid comprising a fruit juice with a high sugar content, e.g., apple juice or pear juice with a genetically modified yeast cell of the present disclosure. In some cases, a fermented beverage is made by fermenting a liquid comprising an extract of a cereal with a genetically modified yeast cell of the present disclosure. Suitable cereals may for example be selected from the group consisting of barley, wheat, rye, oat, maize, rice, sorghum, millet, triticale, buckwheat, fonio and *quinoa*. In some cases, the cereal is selected from the groups consisting of barley, wheat, rye, oat, maize and rice. In some cases, the cereal is barley.

A fermented beverage of the present disclosure can have an alcohol content from about 0.1% to about 10%, e.g., from about 0.1% to 0.5%, from 0.5% to 1%, from 1% to 5%, from 5% to 7.5%, or from 7.5% to 10%.

In some cases, the fermented beverage is wine. In some cases, the fermented beverage is cider. In some cases, the fermented beverage is champagne (sparkling wine). In some cases, the beverage is fermented, then distilled.

Nucleic Acids

The present disclosure provides a nucleic acid comprising a nucleotide sequence encoding a linalool synthase comprising an amino acid sequence having at least 75%, at least 85%, at least 90%, at least 95%, at least 98%, at least 99%, or 100%, amino acid sequence identity to the amino acid sequence depicted in FIG. 6B. In some cases, the encoded linalool synthase has a length of from 530 amino acids to 550 amino acids. In some cases, the encoded linalool synthase has a length of 540 amino acids. The encoded linalool synthase lacks a PTS.

In some cases, the nucleotide sequence encoding the linalool synthase is operably linked to a transcriptional control element that is functional in the host cell. For example, in some cases, the nucleotide sequence encoding the linalool synthase is operably linked to a transcriptional control element that is functional a yeast cell. In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein in: DNA Cloning Vol. 11, A Practical Approach, Ed. DM Glover, 1986, IRL Press, Wash., D.C.). Alternatively, vectors may be used which promote integration of foreign DNA sequences into the yeast chromosome. Another suitable promoter is a GAL10 promoter.

In some cases, the nucleotide sequence encoding linalool synthase is operably linked to a promoter that is functional in a yeast cell. In some cases, the promoter is a GAL1 promoter or a GAL10 promoter. Other suitable promoters include, e.g., a THD3 promoter, an ALD6 promoter, a PGK1 promoter, a TEF1 promoter, a TEF2 promoter, a CCW12 promoter, an HHF1 promoter, an HHF2 promoter, a PAB2 promoter, an RPL18b promoter, an RNR1 promoter, an RNR2 promoter, or an HTB2 promoter. Nucleotide sequences of various suitable promoters are provided in FIG. 37A-37D.

In some cases, a nucleic acid of the present disclosure is present in an expression vector. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as yeast). Thus, for example, a nucleic acid encoding a gene product(s) is included in any one of a variety of expression vectors for expressing the gene product(s). Such vectors include chromosomal, non-chromosomal and synthetic DNA sequences.

Methods of Making Jet Fuel

Linalool can be further converted into tetrahydromethylcyclopentadiene dimer (also known as TH-dimer or RJ-4), which can be used as a high density fuel suitable for ramjet or missile propulsion, and has the following chemical structure:

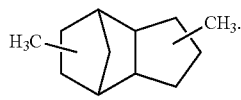

U.S. 2015/0011807 discloses a method for the conversion of renewable, linear terpene alcohol, linalool into a drop-in, high density fuel suitable for ramjet or missile propulsion.

The present disclosure provides a method of making high density fuel, the method comprising: a) culturing a genetically modified host cell of the present disclosure in a suitable culture medium, thereby producing a culture medium comprising linalool; b) isolating the linalool from the culture medium; and c) chemically modifying the linalool to generate high density fuel. The linalool can be isolated, as in step (b), and purified, e.g., generating linalool that is at least 50%, at least 60%, at least 70% at least 75%, at least 80%, at least 85%, at least 90%, at least 95%, at least 98%, at least 99%, or more than 99%, pure, i.e., free of macromolecules and other contaminants that may be present in the culture medium generated in step (a).

For example, the purified linalool can be modified to produce a high density fuel in the following manner: a) reacting the purified linalool with at least one Ru-metathesis catalysts with a solvent or under solvent-free conditions to produce 1-methylcyclopent-2-enol; dehydrating said 1-methylcyclopent-2-enol with at least one heterogeneous dehydration catalyst to produce methylcyclopentadienes; thermal dimerizing of said methylcyclopentadienes to produce methylcyclopentadiene dimers; hydrogenating said methylcyclopentadienes dimers with at least one hydrogenation catalyst to produce hydrogenated methylcyclopentadienes dimers; and isomerizing said hydrogenated methylcyclopentadienes dimers with at least one Lewis acid catalyst to produce high density fuel.

The Ru-metathesis catalysts can be selected from the group consisting of first generation Grubb's catalyst, second generation Grubb's, Grubb's-Hoveyda catalyst, catalysts with electron withdrawing alkoxides and labile pyridine ligands, and any metathesis catalyst tolerant of alcohols, including heterogeneous metal oxides and polymer supported catalysts.

The heterogeneous dehydration catalyst can be selected from the group consisting of $AlPO_4$, $Al_2O_3$, silica, $MgSO_4$, zeolites, and molecular sieves. The thermal dimerizing method can comprise increasing the temperature to accelerate the dimerization of said methylcyclopentadienes to produce methylcyclopentadiene dimers. The at least one hydrogenation catalyst can include at least one of Ni, Pd, Pt, and Cu, either supported or unsupported.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Generation of a Host Strain for Screening Activity of Heterologously Expressed Linalool Synthases S. cerevisiae does not naturally make monoterpenes due to low pathway flux through the mevalonate pathway and the lack of GPP synthase, the enzyme that produces free geranyl diphosphate (GPP)—the immediate precursor of monoterpenes. In order to generate a strain that is competent for monoterpene production, several genetic modifications were integrated into a S. cerevisiae lab strain in 3 separate modules (FIG. 1). The first module encodes middle-pathway genes, ERG8 and ERG19, driven by the galactose inducible GAL10 and GAL1 promoters, respectively. The second module encodes the MvaE and MvaS genes from Enterococcusfaecalis driven by the GAL10 and GAL1 promoters, respectively. This module was targeted to the HMG1 locus, resulting in the overexpression of a truncated form of the HMG-CoA reductase driven by the ADH1 promoter. This enzyme catalyzes the rate-limiting step in the biosynthesis of mevalonate derived compounds, and its truncation was previously shown to increase flux to the mevalonate pathway by removing a membrane-binding region, resulting in cytoplasmic localization (Polakowski, Stahl, and Lang 1998; Ro et al. 2006). The third module encodes the lower-pathway genes, IDI1 and ERG20*(F96W-N127W), driven by the GAL10 and GAL1 promoters, respectively. The ERG20*(F96W-N127W) gene encodes a dominant GPP synthase (Ignea et al. 2014). In order to test whether our engineered strain was competent for monoterpene production, and to test the individual contributions of each module for monoterpene production, an overexpression plasmid encoding a geraniol synthase was introduced that previously exhibited high activity (Liu et al. 2013). Strains were grown in synthetic media with galactose to induce expression of the engineered monoterpene pathway genes. The cultures were supplemented with dodecane, a hydrophobic solvent commonly used as an overlay for trapping volatile nonpolar compounds in microbial fermentations. Results in FIG. 2 demonstrate that incorporation of the upper mevalonate pathway genes MvaE and MvaS (module 2), overexpression of the middle mevalonate pathway genes ERG8 and ERG19 (module 1), overexpression of IDI1 and ERG20*(F96W-N127W) (module 3), and overexpression of geraniol synthase allowed for production of more than 5 mg/L geraniol.

Screening Linalool Synthase Genes for Linalool Synthase Activity

Figure 2C:
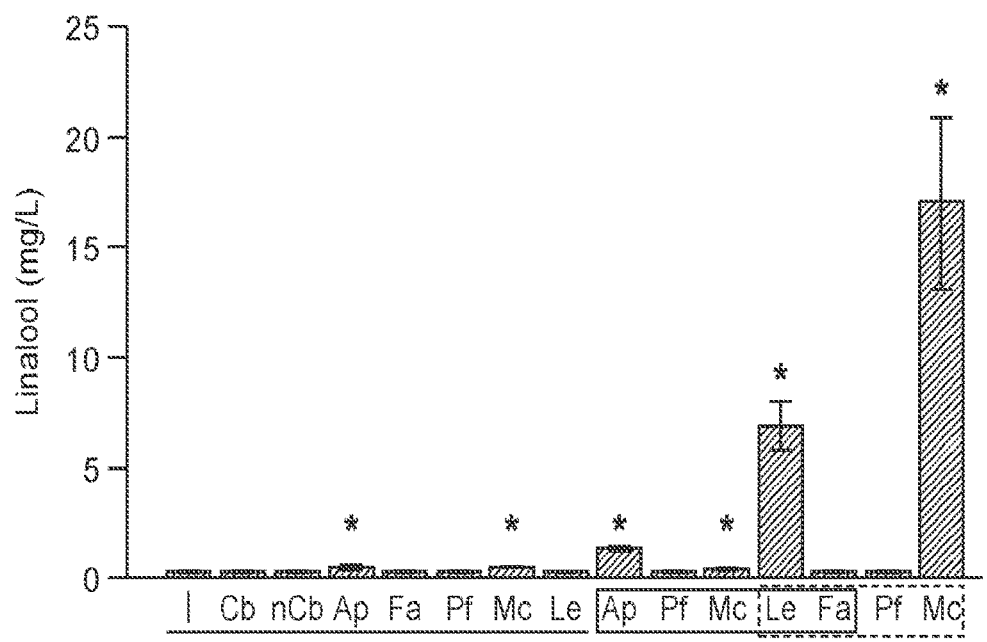

The major technical challenge that was surmounted to reduce this technology to practice was the identification of a gene sequence that, when integrated into a brewing yeast containing ample supply of necessary precursors, encodes a linalool synthase capable of producing linalool at concentrations above the flavor detection threshold in finished beer. Six different yeast-codon optimized genes that were annotated as linalool synthases were expressed from a high copy 2-micron plasmid in the engineered host strain. Only one of the genes exhibited detectable linalool synthase activity, corresponding to the gene from Actinidia polygama (silver vine) (FIG. 2C). WO2008/077986 A1 discloses that the integration of Clarkia breweri linalool synthase in a S. cerevisiae wine strain led to production of linalool above flavor detection threshold. Interestingly, no linalool production was observed when overexpressing this gene. In order to rule out the possibility that the codon optimization disrupted gene expression, the endogenous plant nucleotide sequence was also tested; again, no linalool production was observed.

All linalool synthases reported to date are of plant origin and are expressed in the chloroplast. Plant genes that are targeted to the chloroplast often contain a poorly defined N-terminal amino acid sequence called a plastid targeting sequence (PTS) that directs the newly synthesized protein to the chloroplast. Once the protein is imported into the chloroplast, the PTS is cleaved. Without cleavage, the PTS can destabilize the enzyme and prevent functional heterologous expression. In order to obtain a gene sequence encoding a functional linalool synthase in brewing yeast, various N-terminally truncated gene sequences of the six candidate linalool synthases were tested (FIG. 2A). In order to obtain a gene sequence encoding a functional geraniol synthase in brewing yeast, various N-terminally truncated gene sequences of the six geraniol synthases were tested (FIG. 2B).

The ChloroP algorithm, a neural net-based algorithm designed for PTS prediction (Emanuelsson, Nielsen, and Heijne 1999), was used as a strategy for predicting the ideal site for N-terminal truncation. The output of this algorithm predicted truncation sites for five of the six protein sequences. For 3 of the truncations, no increase in activity was observed. For the linalool synthase from Actinidia polygama, a modest increase in linalool accumulation was observed. For the linalool synthase from Lycopersicon esculentum, a substantial increase in activity was observed (FIG. 2B). Interestingly, the predicted truncation for this polypeptide corresponded to the amino acid immediately N-terminal to a conserved double arginine motif (Bohlmann, Meyer-Gauen, and Croteau 1998). Previous work suggests that this motif serves as an active-site lid to prevent water access to the carbocationic reaction intermediate, and that truncation immediately N-terminal of this site provides a fully active "pseudo-mature" protein when heterologously expressed in a plastid free organism (Williams et al. 1998; Crowell et al. 2002). Therefore, a heuristic, structure based prediction, was used to test whether the activity of the other linalool synthases would be similarly improved. By expressing the pseudo-mature protein corresponding to the Mentha citrata linalool synthase, the highest linalool titer of all tested gene sequences was observed (FIG. 2C). By expressing the pseudo-mature protein corresponding to Ocimum basilicum geraniol synthase, the highest geraniol titer was observed of all tested gene sequences (FIG. 2D)

Incorporation of the linalool biosynthesis pathway into Brewer's yeast and testing its effect on linalool production in a brewing yeast during a brewing fermentation The initial experiments demonstrated that engineered lab yeasts were capable of producing linalool at concentrations significantly higher than the human flavor detection threshold, provided the growth medium was supplemented with a nonpolar solvent capable of retaining the otherwise volatile compound. However, it is difficult to predict whether similar modifications in a brewing strain would result in similar linalool concentrations in a brewing fermentation for the following reasons: i) Production of mevalonate-pathway derived metabolites has not been tested in brewing strains. ii) Brewing fermentation is a micro-aerobic process; the fermentation vessels are equipped with a one-way airlock so that evolved $CO_2$ can escape, but new oxygen cannot enter; on the one hand, limiting oxygen may substantially reduce linalool production, but on the other hand, reducing total gas exchange may increase linalool retention. Therefore, the next step was to test whether an engineered brewing strain grown in a brewing fermentation could accumulate linalool at levels above the human flavor detection threshold. The GPP pathway genes that were shown to improve monoterpene accumulation were integrated into WLP001 California ale yeast (see the website for whitelabs.com/yeast/wlp001-california-ale-yeast) (FIG. 3A). This strain is commonly used by microbreweries for making heavily dry-hopped ales. In order to mimic a brewing fermentation, the strains were grown in a solution of malt extract dissolved in water, in a test tube equipped with a one-way airlock (FIG. 3B). The engineered strain was capable of producing more than 1 mg/L of linalool, which is substantially higher than the limit of human flavor detection.

Figure 1A:
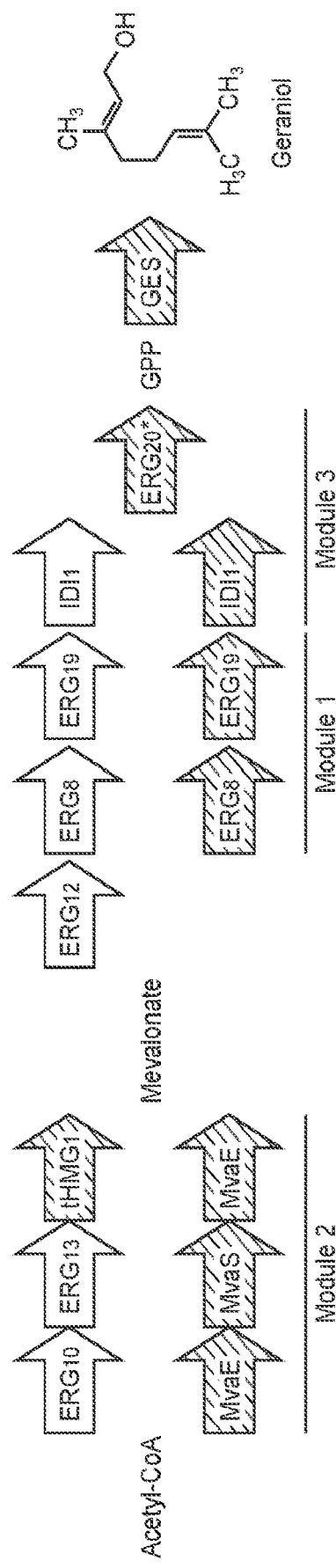
FIG. 1A-1B depict generation of a host strain for screening activity of heterologously expressed geraniol synthases.
Figure 1B:
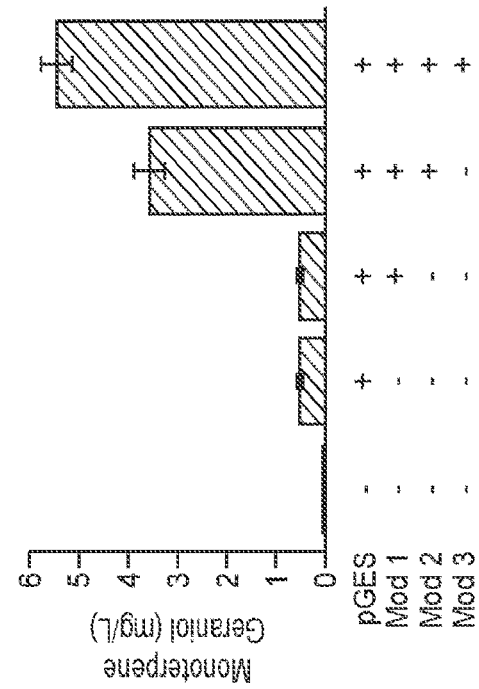

FIG. 1A-1B. Generation of a host strain for screening activity of heterologously expressed geraniol synthases. FIG. 1A shows the pathway modifications were integrated into the lab production strain Cen.PK. The final step of the pathway was mediated by geraniol synthase gene from Ocimum basilicum, which was expressed from a high copy plasmid. FIG. 1B shows the effect of genetic modifications on geraniol production, measured by GC-MS.

Figure 2D:
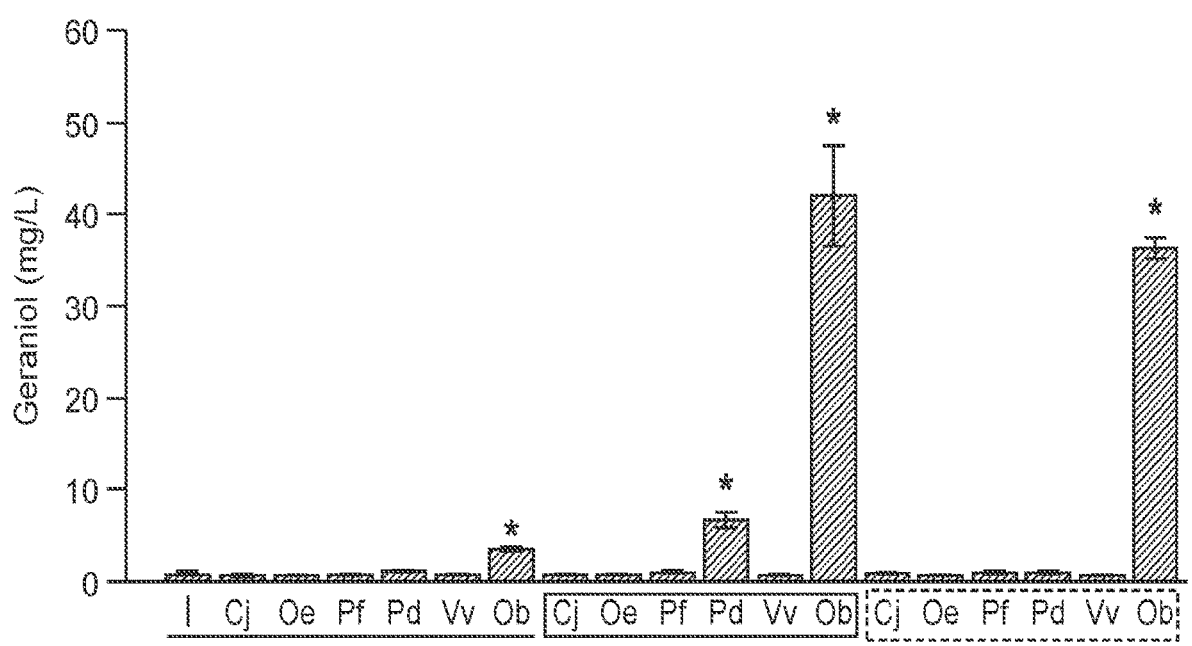

FIG. 2A-2D. Screening activity of full length and PTS-truncated linalool and geraniol synthases. FIG. 2A-B show sequence alignments of N-terminal amino acids for linalool synthase (FIG. 2A) and geraniol synthases (FIG. 2B) from edible plants. The dashed-line box indicates the pseudomature protein sequence as predicted by the RR-heuristic method, the solid-line box indicates additional sequence predicted by ChloroP, and the solid line indicates additional sequence corresponding to the full length peptide. FIG. 2C-D show linalool (FIG. 2C) and geraniol (FIG. 2D) titers produced by cells overexpressing monoterpene synthase genes as measured by GC-MS. Species of origin are indicated by initials, full-length peptides and PTS-truncated peptides predicted by either ChloroP or RR-heuristic method are indicated by underlining, a solid box, and a dashed box, respectively. Error bars correspond to mean±standard deviation of 3 biological replicates. Asterisks indicate statistically significant increases in monoterpene production compared with the control strain as determined by a t-test at p-value<0.025.

Figure 3C:
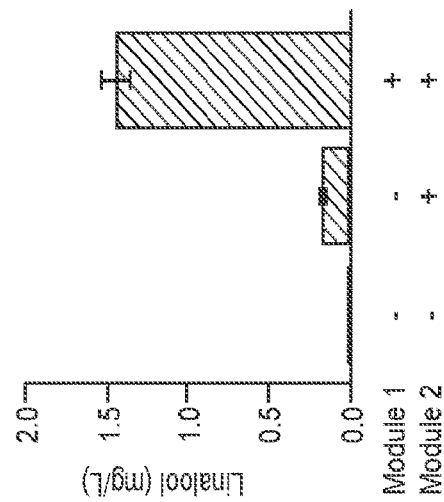
Figure 3B:
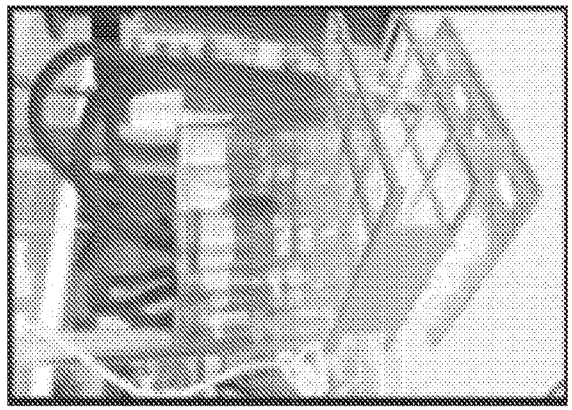

FIG. 3. Incorporation of the linalool biosynthesis pathway into Brewer's yeast and testing its effect on linalool production in a brewing yeast during a brewing fermentation.

Figure 24:
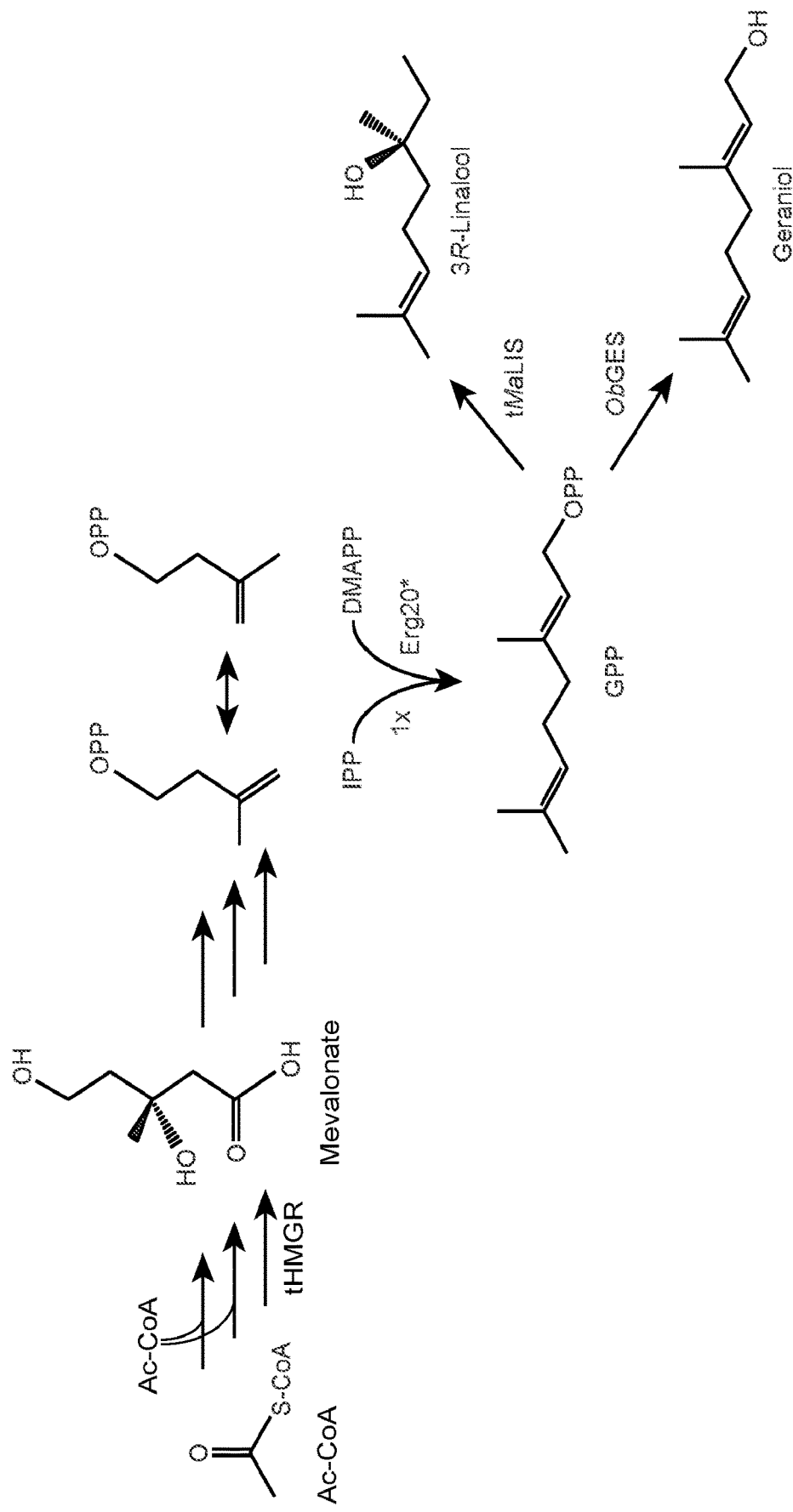
FIG. 24 is a schematic depiction of a monoterpene biosynthesis pathway showing GPP, linalool, and geraniol biosynthesis.

FIG. 24. Terpene biosynthesis pathway schematic illustrating genes to be modulated for generating range of linalool/geraniol production levels. Each chemical reaction between the central carbon metabolite Acetyl-CoA and Linalool/Geraniol is represented by an arrow. Chemical structures of key metabolites are illustrated. Biosynthetic steps where gene expression will be modulated include the step from IPP or DMAPP to GPP, and the step from GPP to linalool or geraniol.

Figure 33A:
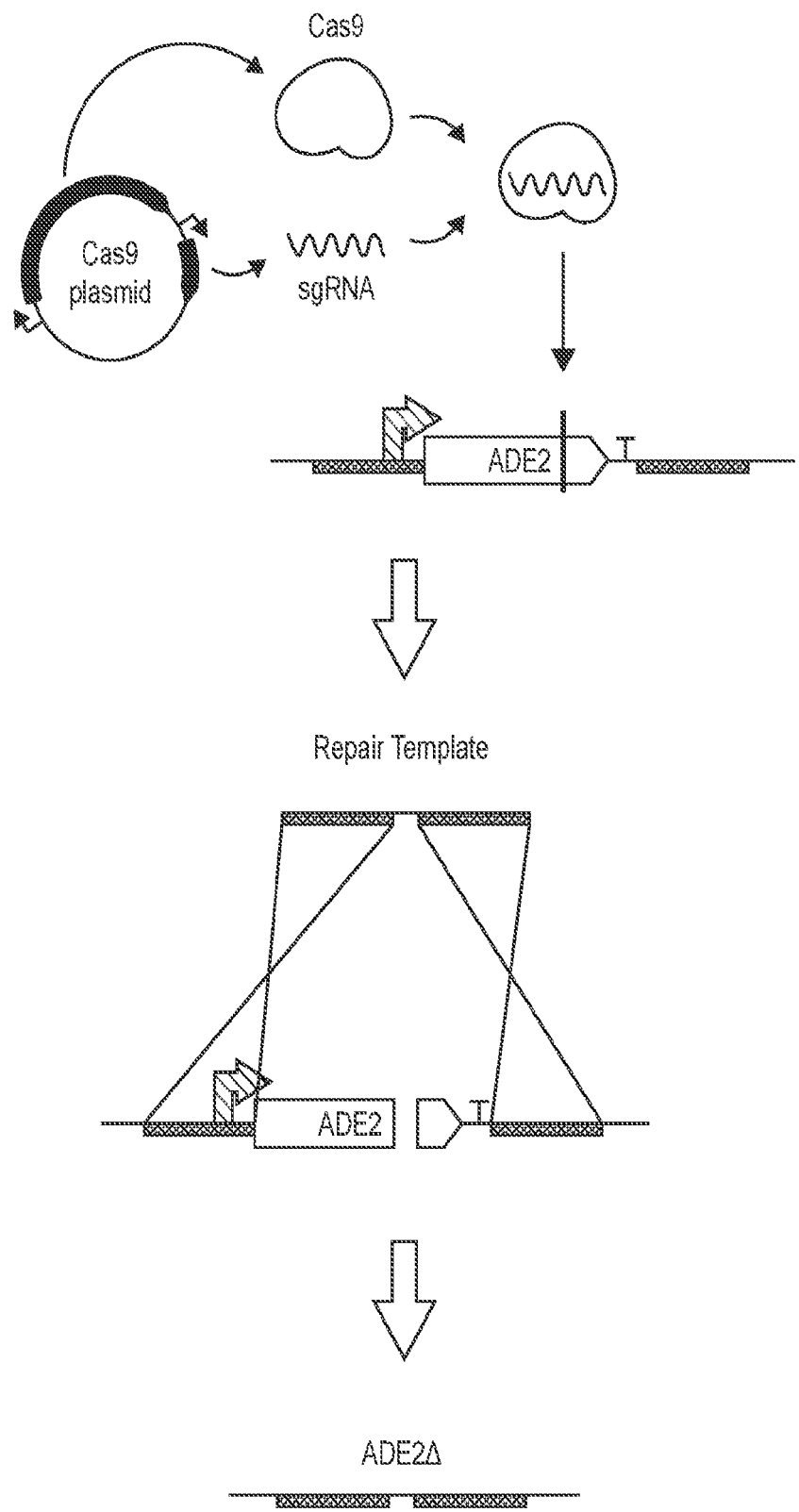
FIG. 33A-33D show methodology for stable and markerless integration of polyploidy brewers yeast.
Figure 33B:
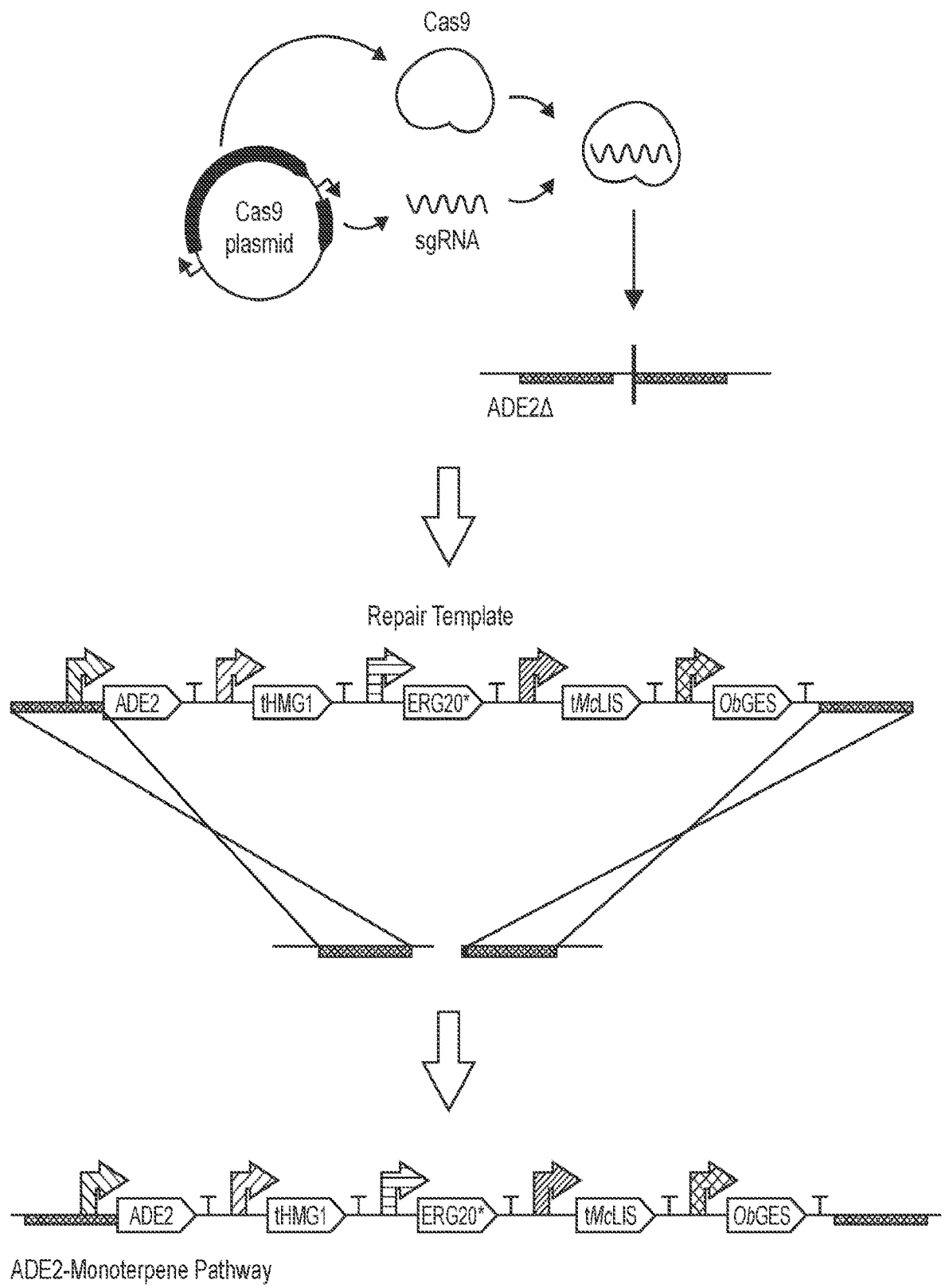
Figure 33C:
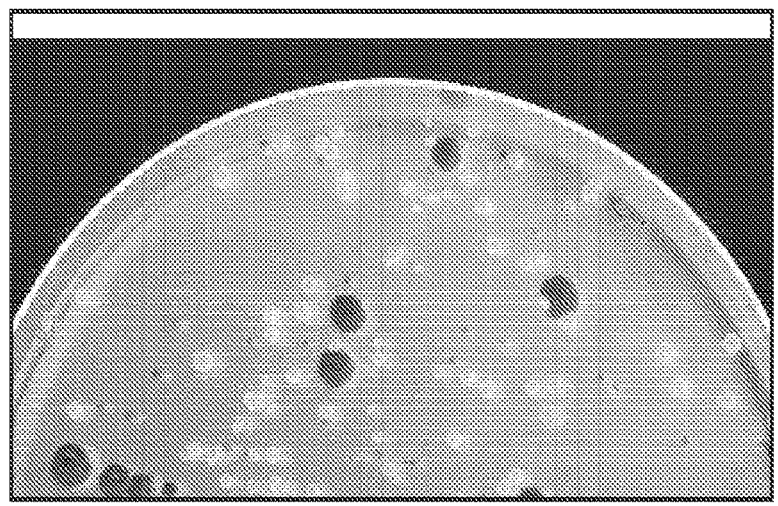
Figure 33D:
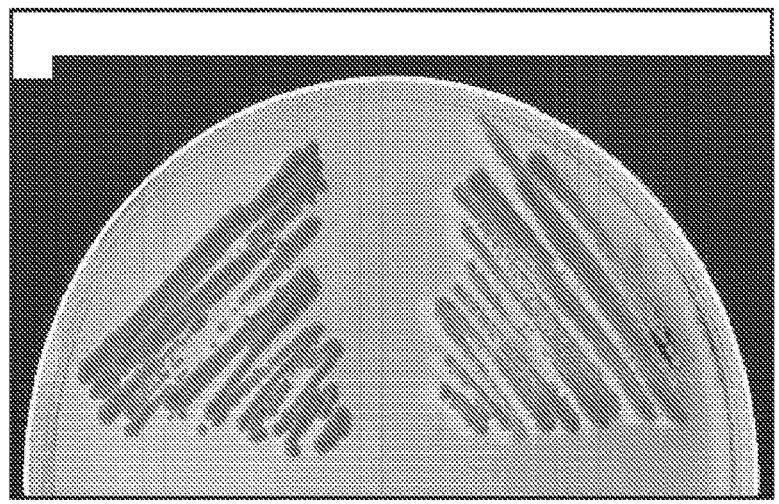
Figure 34:
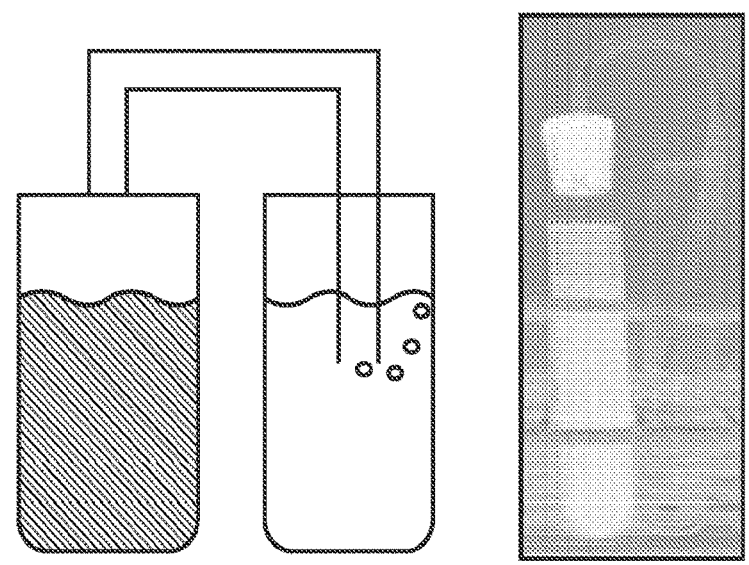
FIG. 34 shows a schematic and photograph representing microaerobic growth conditions used to mimic industrial fermentation conditions. Media used for fermentation is 10% malt extract.

FIG. 33A-D. The methodology for stable and markerless integration in polyploid brewers yeast. FIG. 33A. A schematic illustrating brewer's yeast strain WLP001 co-transformed with a Cas9 plasmid and a repair template to generate ADE2Δ strain. The Cas9 plasmid contains the Cas9 gene and a sequence encoding a sgRNA that targets a double strand break (DSB) to the ADE2 gene. Repair of the DSB with a template containing concatenated 5' and 3' ADE2 sequences results in ADE2 gene deletion. FIG. 33B shows a schematic illustrating ADE2Δ strain co-transformed with a Cas9 plasmid and a repair template to generate ADE2-Monoterpene Pathway strain. The sgRNA targets a DSB to the ADE2 3' sequence. The repair template contains the Monoterpene Pathway genes as well as the ADE2 gene. FIG. 33C shows a representative transformation plate where ADE2Δ strain was co-transformed with Cas9 plasmid and a repair template to generate an ADE2-Monoterpene Pathway strain. ADE2 encodes an enzymatic step in purine biosynthesis, and its deletion results in accumulation of a metabolite with red pigment when grown on media containing intermediate concentrations of adenine. Because the repair template contains the ADE2 gene, templated DSB repair results in a white colony. FIG. 33D shows white colonies streaked from transformation plates result in either white colony color (left), or in mixed and variegated colony color (right). White colonies are stable integrants and variegated colonies are not. Therefore, the colony pattern can be used to select stable integrants. Because WLP001 is a polyploid yeast, stable integration requires templated DSB repair at multiple ADE2Δ loci.

Figure 35:
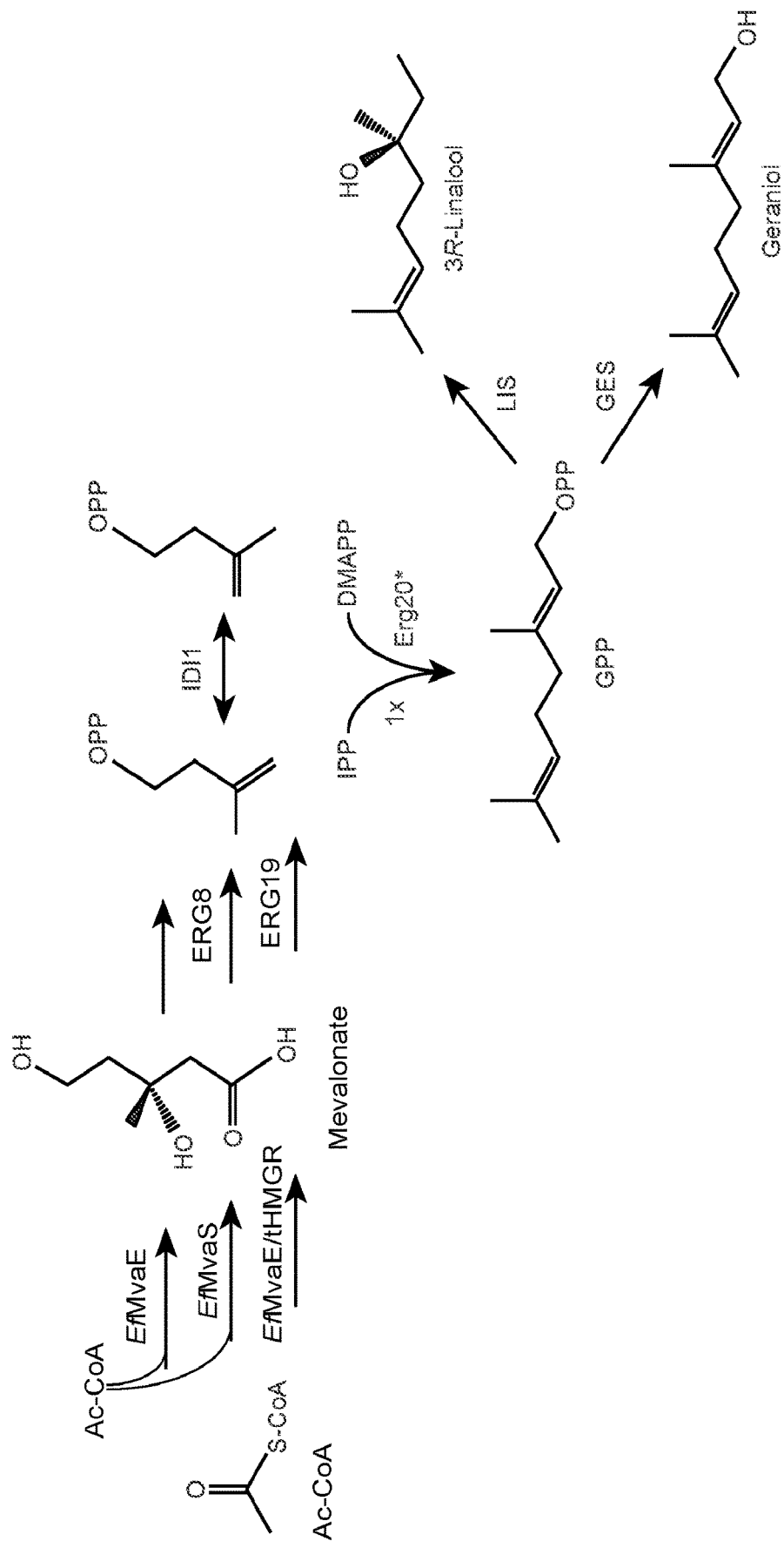
FIG. 35 shows a schematic of genetic modifications incorporated into GPP hyper-producing strain used for screening linalool and geraniol synthases.

FIG. 35. Schematic of genetic modifications incorporated into GPP hyper-producing strain used for screening linalool and geraniol synthases. The MvaE and MvaS genes from Enterococcusfaecalis encode the first three steps in the mevalonate pathway, and their overexpression results in increased levels of mevalonate-derived compounds1. The ADH1 promoter was integrated at the HMG1 locus, resulting in the overexpression of a truncated form of the HMG-CoA reductase. This enzyme catalyzes the rate-limiting step in the biosynthesis of mevalonate derived compounds, and its truncation increases flux to the mevalonate pathway by removing an ER-anchored transmembrane region, resulting in deregulation and cytoplasmic localization2. ERG20F96W-N127W, encodes a synthetic dominant negative GPP synthase.

Additional Strains

Monoterpene synthases are tested using similar methods as described above to identify a myrcene synthase that is highly active in *Saccharomyces cerevisiae*. Sesquiterpene synthases are screened to identify a caryophyllene synthase that is highly active in *Saccharomyces cerevisiae*. Genetic modifications that encode the rate-limiting biosynthetic steps are combined, so that the resulting engineered brewing strains will produce various combinations of monoterpenes and sesquiterpenes in finished beer. In addition, the genes encoding rate-limiting steps are expressed at different levels so as to achieve terpene production over a range of different concentrations. Many different combinations are generated, and production data are used to create a predictive model. This model is used to generate strains with finely tuned compositions of flavor molecules.

Important Note on Methodology

To date, all genetic modifications have been incorporated into Brewer's yeast by traditional methods where homologous recombination transformants are selected based on resistance to antifungal drugs; the genes controlling terpene biosynthesis are coupled with a drug resistance gene, and the incorporation of terpene biosynthesis genes are selected by growing the transformed cells on drug-containing media. This method may be problematic for commercialization because these drug resistance genes are of bacterial origin, and are not derived from Generally Regarded As Safe (GRAS) organisms. Moving forward, a CRISPR-based integration strategy is developed that obviates this complication. Final engineering efforts will include only genes that are either derived from *Saccharomyces cerevisiae*, or derived from plants that already have GRAS status.

Production of Geraniol and Linalool in a Host *Saccharomyces cerevisiae* Strain

Figure 26:
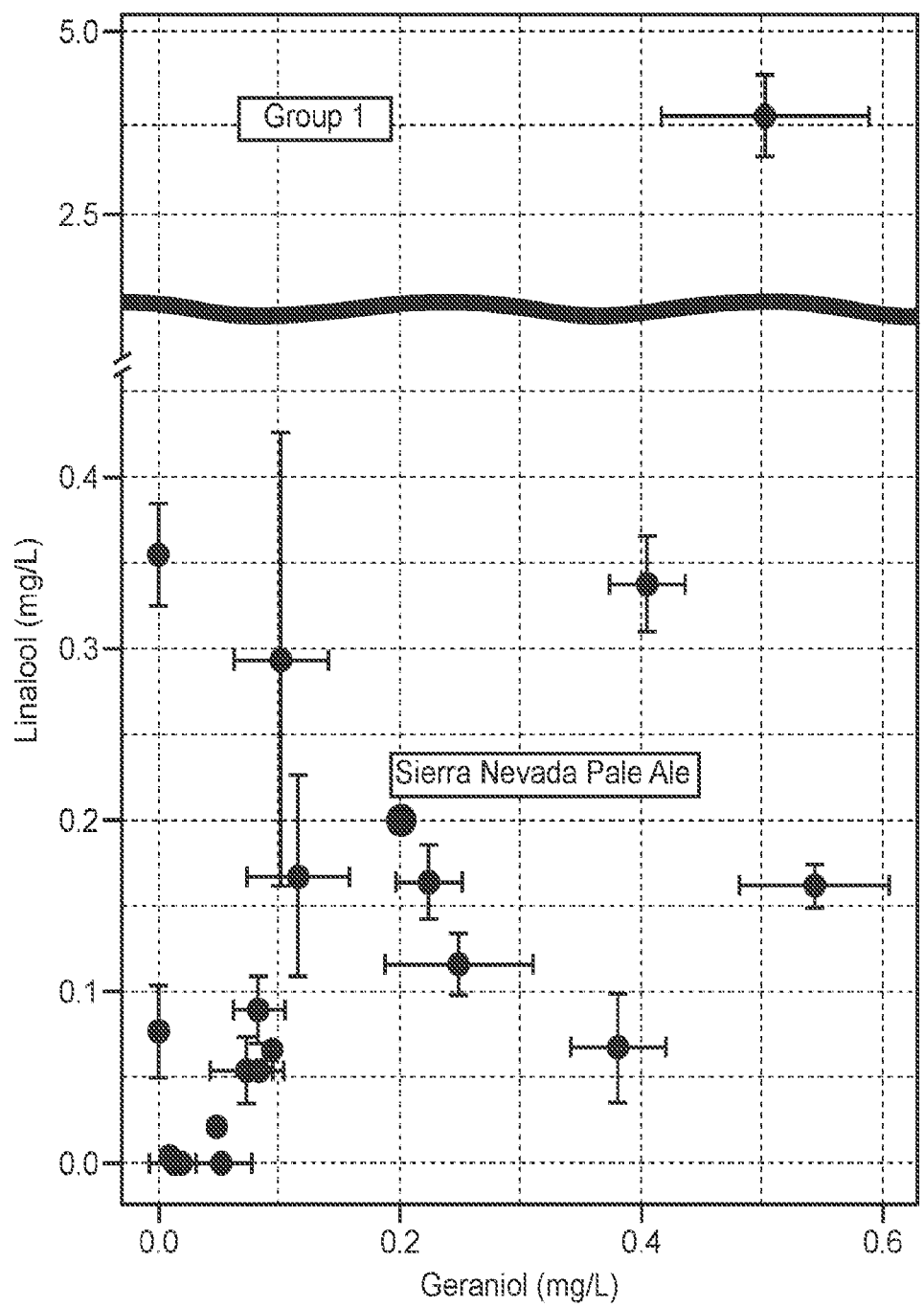
FIG. 26 depicts the amounts of geraniol and linalool produced by genetically modified yeast cells of the present disclosure. The amounts of geraniol and linalool present in a commonly sold beer (Sierra Nevada Pale Ale) are shown for comparison.
Figure 26:
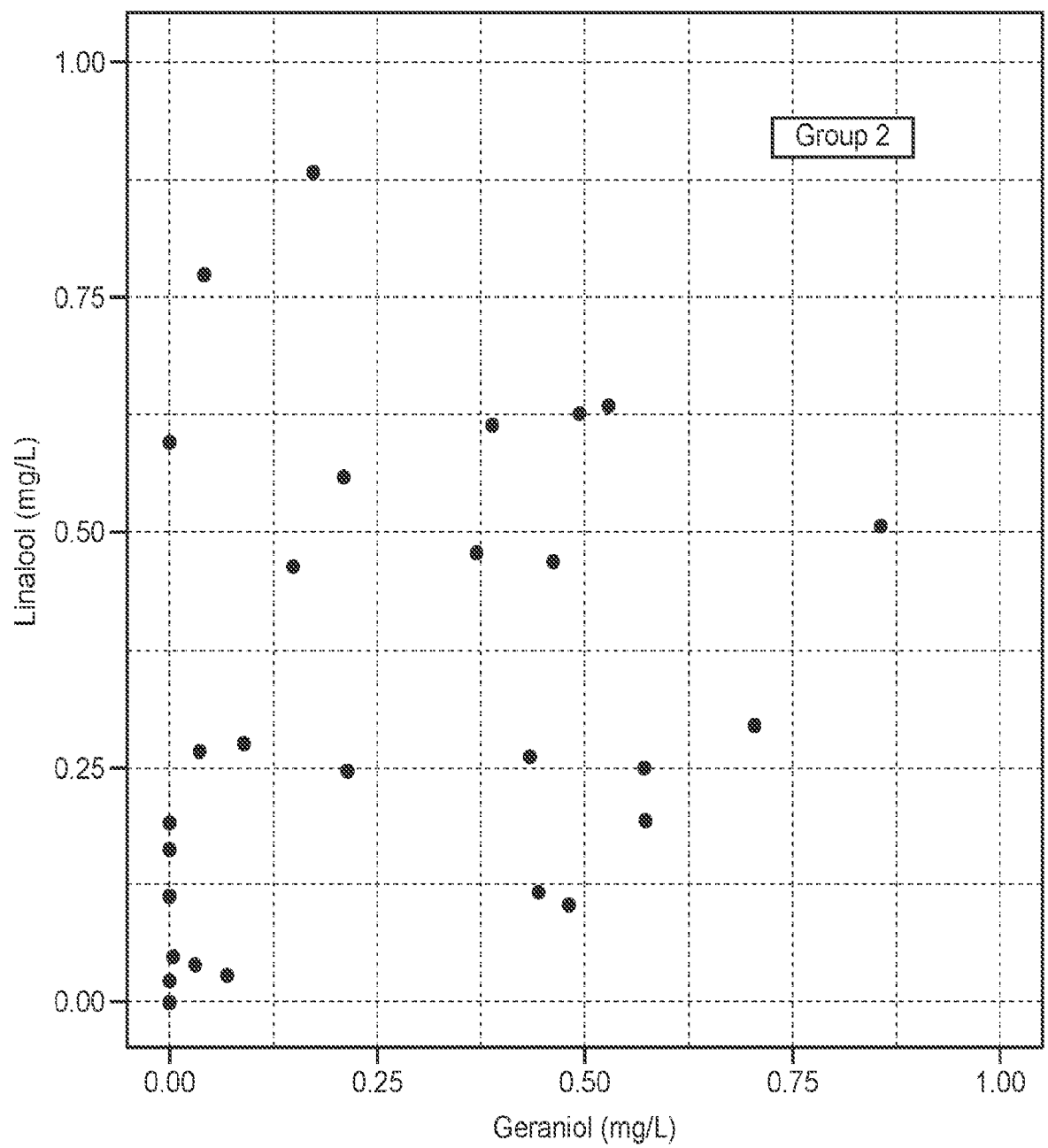
Figure 31A:
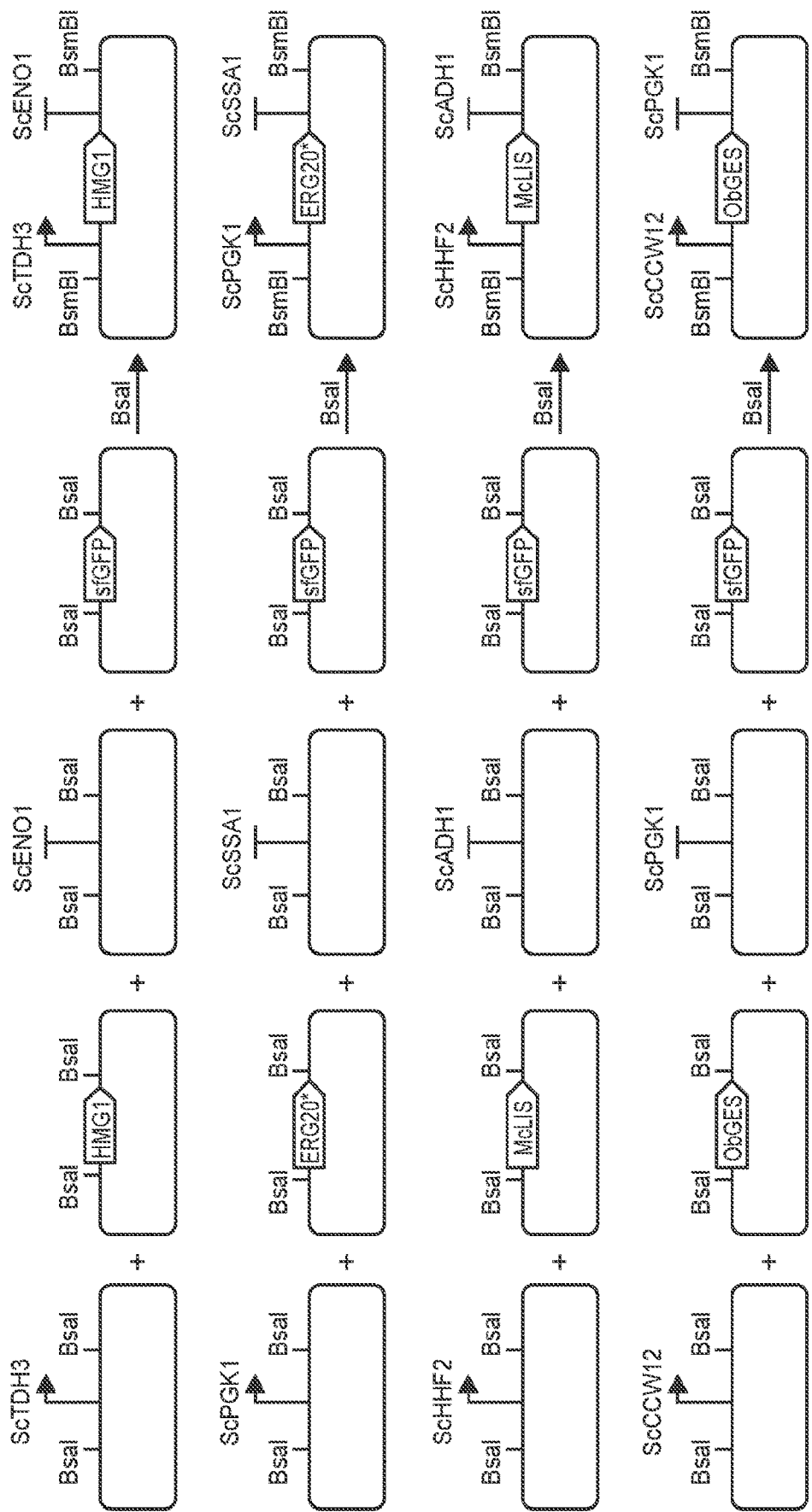
FIG. 31A-31B show the methodology for constructing repair template for Cas9-mediated pathway integration.
Figure 31B:
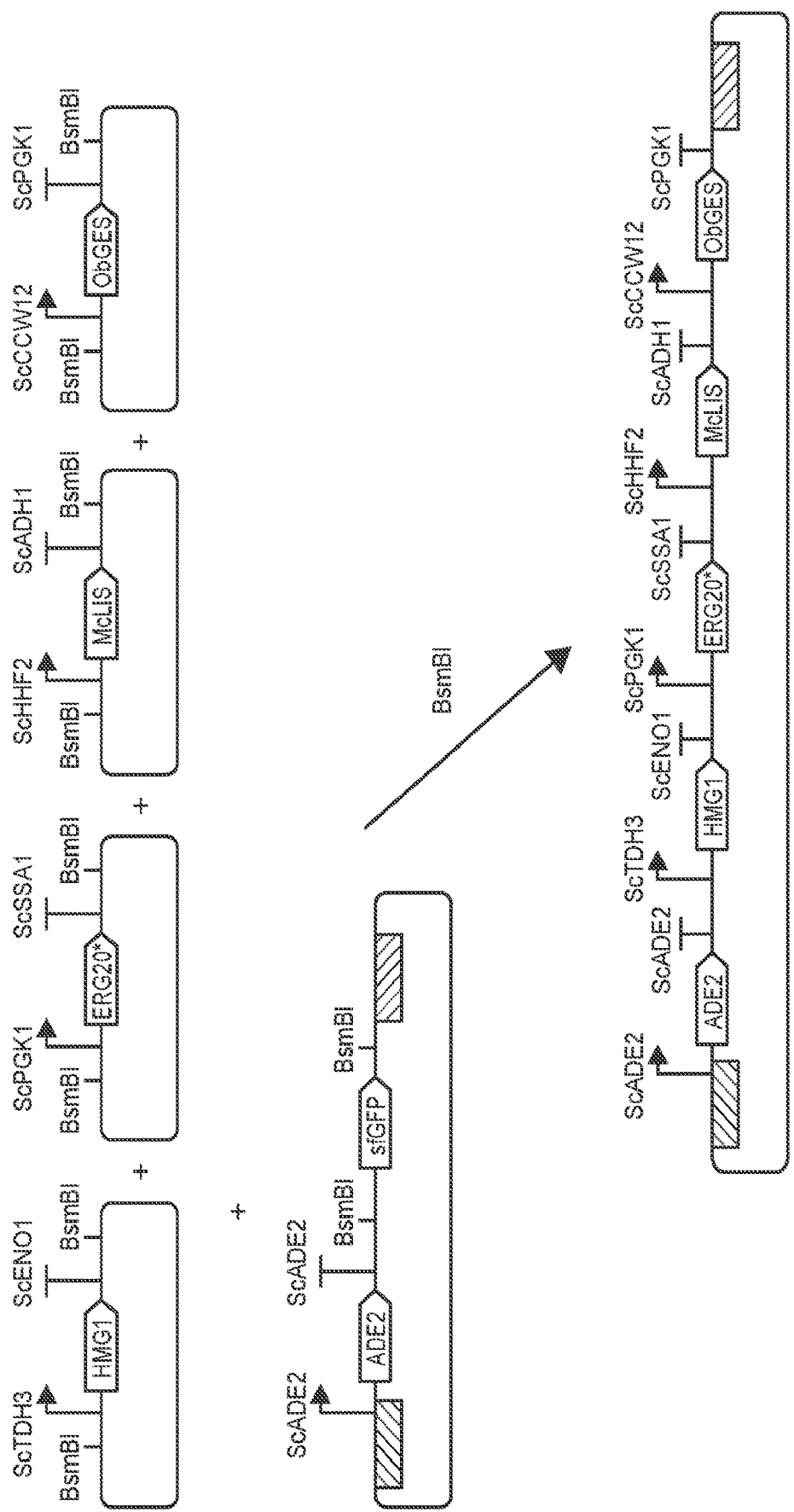
Figure 32:
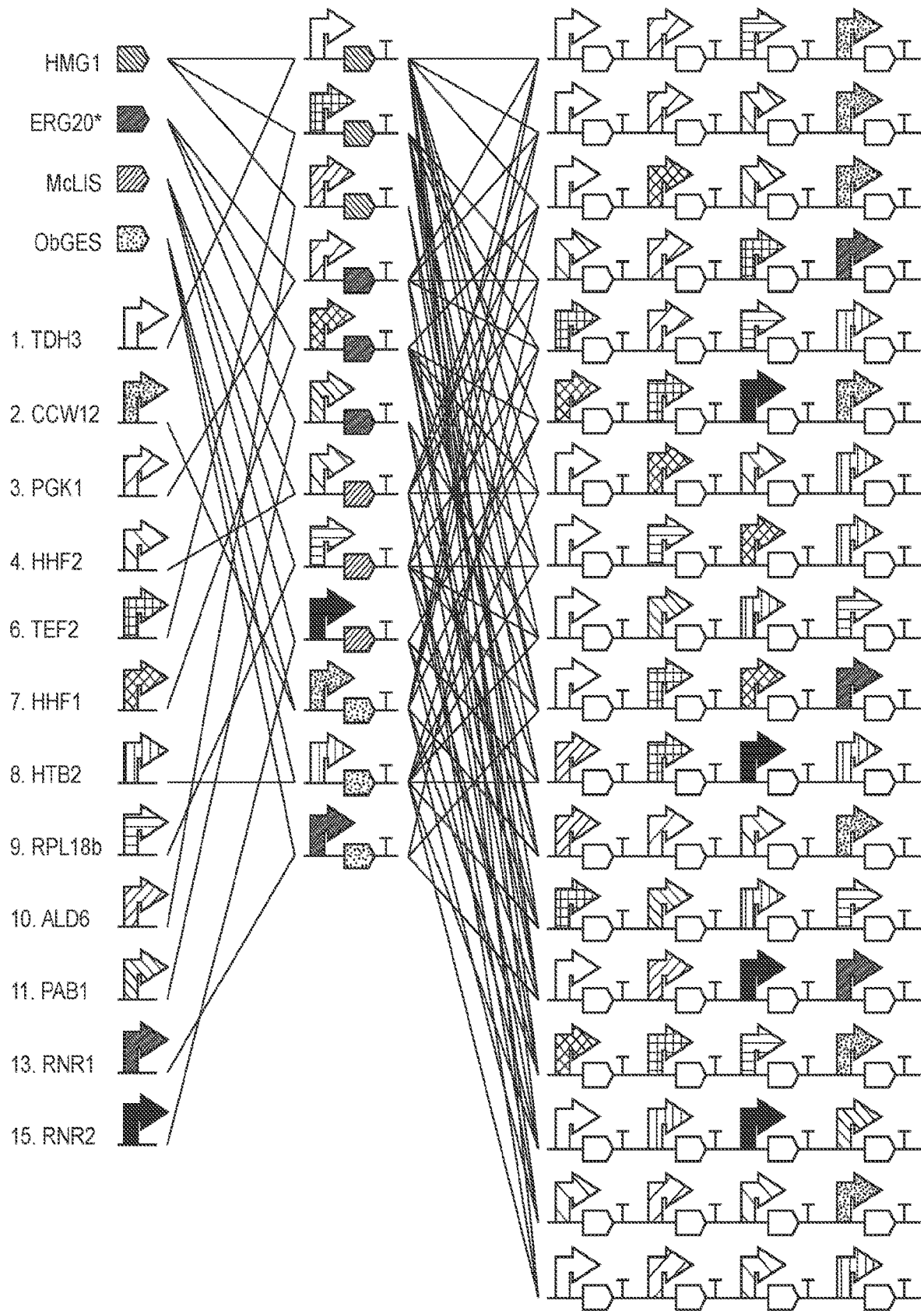
FIG. 32 schematically depicts combinatorial assembly of repair templates for Cas9-mediated pathway integration.

FIG. 26 depicts monoterpene production in brewer's strain WLP001 with various promoter combinations driving expression of 4 modulated pathway genes as shown by production of geraniol and linalool. Expression of tHMGR, ERG20, linalool synthase, and geraniol synthase was under transcriptional control of various promoters, as shown in FIG. 38.

REFERENCES

Bohlmann, J., G. Meyer-Gauen, and R. Croteau. 1998. "Plant Terpenoid Synthases: Molecular Biology and Phylogenetic Analysis." *Proceedings of the National Academy of Sciences of the United States of America* 95 (8): 4126-33.

Crowell, Anastasia L., David C. Williams, Edward M. Davis, Mark R. Wildung, and Rodney Croteau. 2002. "Molecular Cloning and Characterization of a New Linalool Synthase." *Archives of Biochemistry and Biophysics* 405 (1): 112-21.

Emanuelsson, O., H. Nielsen, and G. von Heijne. 1999. "ChloroP, a Neural Network-Based Method for Predicting Chloroplast Transit Peptides and Their Cleavage Sites." *Protein Science: A Publication of the Protein Society* 8 (5): 978-84.

Ignea, Codruta, Marianna Pontini, Massimo E. Maffei, Antonios M. Makris, and Sotirios C. Kampranis. 2014. "Engineering Monoterpene Production in Yeast Using a Synthetic Dominant Negative Geranyl Diphosphate Synthase." *ACS Synthetic Biology* 3 (5): 298-306.

Liu, Jidong, Weiping Zhang, Guocheng Du, Jian Chen, and Jingwen Zhou. 2013. "Overproduction of Geraniol by Enhanced Precursor Supply in *Saccharomyces Cerevisiae*." *Journal of Biotechnology* 168 (4): 446-51.

Polakowski, T., U. Stahl, and C. Lang. 1998. "Overexpression of a Cytosolic Hydroxymethylglutaryl-CoA Reductase Leads to Squalene Accumulation in Yeast." *Applied Microbiology and Biotechnology* 49 (1): 66-71.

Ro, Dae-Kyun, Eric M. Paradise, Mario Ouellet, Karl J. Fisher, Karyn L. Newman, John M. Ndungu, Kimberly A. Ho, et al. 2006. "Production of the Antimalarial Drug Precursor Artemisinic Acid in Engineered Yeast." *Nature* 440 (7086): 940-43.

Williams, D. C., D. J. McGarvey, E. J. Katahira, and R. Croteau. 1998. "Truncation of Limonene Synthase Preprotein Provides a Fully Active 'Pseudomature' Form of This Monoterpene Cyclase and Reveals the Function of the Amino-Terminal Arginine Pair." *Biochemistry* 37 (35): 12213-20.

Rodriguez, S. et al. ATP citrate lyase mediated cytosolic acetyl-CoA biosynthesis increases mevalonate production in *Saccharomyces cerevisiae*. Microb. Cell Fact. 15, 48 (2016).

Polakowski, T., Stahl, U. & Lang, C. Overexpression of a cytosolic hydroxymethylglutaryl-CoA reductase leads to squalene accumulation in yeast. Appl. Microbiol. Biotechnol. 49, 66-71 (1998).

Ignea, C., Pontini, M., Maffei, M. E., Makris, A. M. & Kampranis, S. C. Engineering monoterpene production in yeast using a synthetic dominant negative geranyl diphosphate synthase. ACS Synth. Biol. 3, 298-306 (2014).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell, wherein the host cell is a diploid or tetraploid yeast cell and is genetically modified with a heterologous nucleic acid comprising a nucleotide sequence encoding linalool synthase, wherein the linalool synthase lacks a plastid targeting sequence and wherein the linalool synthase comprises an amino acid sequence having at least 85% amino acid sequence identity to the amino acid sequence set forth in SEQ ID NO:7, SEQ ID NO:8, or SEQ ID NO:13.

2. The genetically modified host cell of claim 1, wherein the linalool synthase comprises an amino acid sequence having at least 95% sequence identity to the amino acid sequence set forth in SEQ ID NO:7, SEQ ID NO:8, or SEQ ID NO:13.

3. The genetically modified host cell of claim 1, wherein the genetically modified host cell produces linalool in an amount of at least 0.05 mg per liter of medium or in an amount of at least 1 mg per dry cell weight.

4. The genetically modified host cell of claim 1, wherein the genetically modified host cell is genetically modified with a nucleic acid comprising a nucleotide sequence encoding a truncated 3'-hydroxy-3-methylglutaryl-coenzyme A reductase (tHMGR).

5. The genetically modified host cell of claim 1, wherein the genetically modified host cell is genetically modified such that the endogenous farnesyl diphosphate synthase (FPPS) is modified to comprise one or more amino acid substitutions at positions selected from F96, N127, and K197, relative to the amino acid sequence set forth in SEQ ID NO:17.

6. The genetically modified host cell of claim 5, wherein the modified FPPS comprises an amino acid sequence having at least 85% amino acid sequence identity to:
   a) the FPPS amino acid sequence set forth in SEQ ID NO:18, and comprises an F96W substitution and an N127W substitution; or
   b) the FPPS amino acid sequence set forth in SEQ ID NO:19, and comprises a K197E substitution.

7. The genetically modified host cell of claim 5, wherein the genetically modified host cell is genetically modified with a heterologous nucleic acid comprising a nucleotide sequence encoding a geraniol synthase.

8. The genetically modified host cell of claim 7, wherein the geraniol synthase comprises an amino acid sequence having at least 95% amino acid sequence identity to the geraniol synthase set forth in any one of SEQ ID NOs:20-23 and 28-31.

9. The genetically modified host cell of claim 7, wherein the genetically modified host cell produces linalool and geraniol.

10. The genetically modified host cell of claim 9, wherein the linalool synthase has a length of from 530 amino acids to 550 amino acids.

11. The genetically modified host cell of claim 7, wherein the geraniol synthase does not comprise a plastid targeting sequence.

12. The genetically modified host cell of claim 1, wherein the genetically modified host cell is genetically modified with a heterologous nucleic acid comprising: a) a promoter; and b) a nucleotide sequence encoding a geraniol reductase, wherein the nucleotide sequence encoding the geraniol reductase is operably linked to the promoter, and wherein the promoter is heterologous to the nucleotide sequence encoding the geraniol reductase.

13. The genetically modified host cell of claim 12, wherein the geraniol reductase comprises an amino acid sequence having at least 85% amino acid sequence identity to the amino acid sequence set forth in SEQ ID NO:32.

14. The genetically modified host cell of claim 1, wherein the linalool synthase comprises an amino acid sequence having at least 85% amino acid sequence identity to the amino acid sequence set forth in SEQ ID NO:10.

15. The genetically modified host cell of claim 14, wherein the linalool synthase comprises an amino acid sequence having at least 95% amino acid sequence identity to the amino acid sequence set forth in SEQ ID NO:10.

16. A composition comprising:
   a) the genetically modified host cell of claim 1; and
   b) a culture medium.

17. A method of producing a fermented beverage, the method comprising culturing the composition of claim 16 for a time period and under conditions suitable for fermentation.

* * * * *

```
                             SEQUENCE LISTING

<160> NUMBER OF SEQ ID NOS: 51

<210> SEQ ID NO 1
<211> LENGTH: 95
<212> TYPE: PRT
<213> ORGANISM: Clarkia breweri

<400> SEQUENCE: 1

Met Gln Leu Ile Thr Asn Phe Ser Ser Ser Ser Glu Leu Gln Phe
1               5                   10                  15

Leu Val Asp Lys Val Lys Arg Glu Ser Leu Ser Ser Ser Ser Asn
                20                  25                  30

Thr Gln Asn Leu Phe Leu Ser Thr Ser Pro Tyr Asp Thr Ala Trp Leu
            35                  40                  45

Ala Leu Ile Pro His Pro His His His His His Gly Arg Pro Met
        50                  55                  60

Phe Glu Lys Cys Leu Gln Trp Ile Leu His Asn Gln Thr Pro Gln Gly
65                  70                  75                  80

Phe Trp Ala Ala Ala Gly Asp Asn Ile Ser Asp Thr Asp Asp Asp
                85                  90                  95

<210> SEQ ID NO 2
<211> LENGTH: 95
<212> TYPE: PRT
<213> ORGANISM: Actinidia polygama

<400> SEQUENCE: 2

Met Ala Ser Phe His Arg Phe Cys Val Ser Ser Leu Leu Val Pro Asn
1               5                   10                  15

Asn Ser Pro Gln Ile Ser Asn Ala Tyr Arg Ala Pro Ala Val Pro Ser
                20                  25                  30

Met Pro Thr Thr Gln Lys Trp Ser Ile Thr Glu Asp Leu Ala Phe Ile
            35                  40                  45

Ser Asn Pro Ser Lys Gln His Asn His Gln Thr Gly Tyr Arg Thr Phe
        50                  55                  60

Ser Asp Glu Phe Tyr Val Lys Arg Glu Lys Lys Leu Lys Asp Val Arg
65                  70                  75                  80

Arg Ala Leu Arg Glu Val Glu Glu Thr Pro Leu Glu Gly Leu Val
                85                  90                  95

<210> SEQ ID NO 3
<211> LENGTH: 95
<212> TYPE: PRT
<213> ORGANISM: Fragaria x ananassa

<400> SEQUENCE: 3

Met Pro Val His Ala Thr Pro Ala Ala Glu Ser Gln Ile Ile Ser Lys
1               5                   10                  15

Pro Glu Val Val Arg Arg Thr Ala Asn Phe Lys Pro Ser Val Trp Gly
                20                  25                  30

Asp Arg Phe Ala Asn Tyr Ala Glu Asp Ile Ile Thr Gln Thr Gln Met
            35                  40                  45
```

```
Gln Glu Gln Val Glu Glu Leu Lys Gln Val Val Arg Lys Glu Val Phe
 50                  55                  60

Thr Asn Ala Ala Asp Asp Ser Ser His Gln Leu Lys Leu Ile Asp Glu
 65                  70                  75                  80

Ile Gln Arg Leu Gly Val Ala Tyr His Phe Glu Ser Glu Ile Asp
                 85                  90                  95

<210> SEQ ID NO 4
<211> LENGTH: 95
<212> TYPE: PRT
<213> ORGANISM: Perilla frutescens

<400> SEQUENCE: 4

Met Ser Ser Met Arg Ile Tyr Val Ala Ile Met Lys Lys Pro Ser Val
 1               5                  10                  15

Lys His Val Asp Asn Val Asp Lys Lys Ala Ser Lys Pro Ser Trp Arg
                 20                  25                  30

Val Ser Ser Ala Thr Ala Gly Leu Arg Ala Ser Ser Ser Leu Gln
             35                  40                  45

Leu Asp Val Lys Lys Pro Ala Asp Glu Ile Leu Thr Ala Arg Arg Ser
 50                  55                  60

Gly Asn Tyr Gln Pro Ser Leu Trp Asp Phe Asn Tyr Leu Gln Pro Leu
 65                  70                  75                  80

Asn Thr Thr His Tyr Lys Glu Glu Arg His Leu Lys Arg Glu Ala
                 85                  90                  95

<210> SEQ ID NO 5
<211> LENGTH: 95
<212> TYPE: PRT
<213> ORGANISM: Mentha citrata

<400> SEQUENCE: 5

Met Cys Thr Ile Ile Ser Val Asn His His Val Ala Ile Leu Ser
 1               5                  10                  15

Lys Pro Lys Val Lys Leu Phe His Thr Lys Asn Lys Arg Ser Ala Ser
                 20                  25                  30

Ile Asn Leu Pro Trp Ser Leu Ser Pro Ser Ser Ala Ala Ser Arg
             35                  40                  45

Pro Ile Ser Cys Ser Ile Ser Ser Lys Leu Tyr Thr Ile Ser Ser Ala
 50                  55                  60

Gln Glu Glu Thr Arg Arg Ser Gly Asn Tyr His Pro Ser Val Trp Asp
 65                  70                  75                  80

Phe Asp Phe Ile Gln Ser Leu Asp Thr Asp His Tyr Lys Glu Glu
                 85                  90                  95

<210> SEQ ID NO 6
<211> LENGTH: 95
<212> TYPE: PRT
<213> ORGANISM: Lycopersicon esculentum

<400> SEQUENCE: 6

Met Val Ser Ile Leu Ser Asn Ile Gly Met Met Val Val Thr Phe Lys
 1               5                  10                  15

Arg Pro Ser Leu Phe Thr Ser Leu Arg Arg Ser Ala Asn Asn Ile
                 20                  25                  30

Ile Ile Thr Lys His Ser His Pro Ile Ser Thr Thr Arg Arg Ser Gly
             35                  40                  45

Asn Tyr Lys Pro Thr Met Trp Asp Phe Gln Phe Ile Gln Ser Leu His
```

```
            50                  55                  60
Asn Pro Tyr Glu Gly Asp Lys Tyr Met Lys Arg Leu Asn Lys Leu Lys
 65                  70                  75                  80

Lys Glu Val Lys Lys Met Met Met Thr Val Glu Gly Ser His Asp
                 85                  90                  95

<210> SEQ ID NO 7
<211> LENGTH: 574
<212> TYPE: PRT
<213> ORGANISM: Actinidia polygama

<400> SEQUENCE: 7

Met Ala Ser Phe His Arg Phe Cys Val Ser Ser Leu Leu Val Pro Asn
  1               5                  10                  15

Asn Ser Pro Gln Ile Ser Asn Ala Tyr Arg Ala Pro Ala Val Pro Ser
                 20                  25                  30

Met Pro Thr Thr Gln Lys Trp Ser Ile Thr Glu Asp Leu Ala Phe Ile
             35                  40                  45

Ser Asn Pro Ser Lys Gln His Asn His Gln Thr Gly Tyr Arg Thr Phe
 50                  55                  60

Ser Asp Glu Phe Tyr Val Lys Arg Glu Lys Lys Leu Lys Asp Val Arg
 65                  70                  75                  80

Arg Ala Leu Arg Glu Val Glu Glu Thr Pro Leu Glu Gly Leu Val Met
                 85                  90                  95

Ile Asp Thr Leu Gln Arg Leu Gly Ile Asp Tyr His Phe Gln Gly Glu
            100                 105                 110

Ile Gly Ala Leu Leu Gln Lys Gln Arg Lys Ser Lys Cys Asp Tyr
            115                 120                 125

Pro Glu His Asp Leu Phe Glu Val Ser Thr Arg Phe Arg Leu Leu Arg
130                 135                 140

Gln Glu Gly His Asn Val Pro Ala Asp Val Phe Asn His Phe Arg Asp
145                 150                 155                 160

Lys Lys Gly Arg Phe Lys Ser Glu Leu Ser Arg Asp Ile Arg Gly Leu
                165                 170                 175

Met Ser Leu Tyr Glu Ala Ser Gln Leu Ser Ile Gln Gly Glu Asp Ile
            180                 185                 190

Leu Asp Gln Ala Ala Asp Phe Ser Ser Gln Leu Leu Ser Gly Trp Ala
            195                 200                 205

Thr Asn Pro Asp His His Gln Ala Arg Leu Val Arg Asn Ala Leu Thr
210                 215                 220

His Pro Tyr His Lys Ser Leu Ala Thr Phe Thr Ala Arg Asn Phe His
225                 230                 235                 240

Tyr Asp Cys Lys Gly Gln Asn Gly Trp Val Asn Asn Leu Gln Glu Leu
                245                 250                 255

Ala Lys Met Asp Leu Thr Val Val Gln Ser Met His Gln Lys Glu Val
            260                 265                 270

Leu Gln Val Ser Gln Trp Trp Lys Asp Arg Gly Leu Ala Asn Glu Leu
            275                 280                 285

Lys Leu Val Arg Asn Gln Pro Leu Lys Trp Tyr Met Trp Pro Met Ala
            290                 295                 300

Ala Leu Thr Asp Pro Arg Phe Ser Glu Glu Arg Val Glu Leu Thr Lys
305                 310                 315                 320

Pro Ile Ser Phe Ile Tyr Ile Ile Asp Asp Ile Phe Asp Val Tyr Gly
                325                 330                 335
```

```
Thr Leu Glu Glu Leu Thr Leu Phe Thr Asp Ala Val Asn Arg Trp Glu
            340                 345                 350

Leu Thr Ala Val Glu Gln Leu Pro Asp Tyr Met Lys Val Cys Phe Lys
        355                 360                 365

Ala Leu Tyr Asp Ile Thr Asn Glu Ile Ala Tyr Lys Ile Tyr Lys Lys
    370                 375                 380

His Gly Trp Asn Pro Ile Asp Ser Leu Arg Arg Met Trp Ala Ser Leu
385                 390                 395                 400

Cys Asn Ala Phe Leu Val Glu Ala Lys Trp Phe Ala Ser Gly His Leu
                405                 410                 415

Pro Lys Ala Glu Glu Tyr Leu Lys Asn Gly Ile Ile Ser Ser Gly Met
            420                 425                 430

His Val Val Thr Val His Met Phe Phe Leu Leu Gly Gly Cys Phe Thr
        435                 440                 445

Asp Glu Ser Val Asn Leu Val Asp Glu His Ala Gly Ile Thr Ser Ser
    450                 455                 460

Ile Ala Thr Ile Leu Arg Leu Ser Asp Asp Leu Gly Ser Ala Lys Asp
465                 470                 475                 480

Glu Asp Gln Asp Gly Tyr Asp Gly Ser Tyr Val Glu Tyr Tyr Leu Lys
                485                 490                 495

Asp His Lys Gly Ser Ser Val Glu Asn Ala Arg Glu Glu Val Ile Arg
            500                 505                 510

Met Ile Ser Asp Ala Trp Lys Arg Leu Asn Glu Glu Cys Leu Ser Pro
        515                 520                 525

Asn Pro Phe Ser Ala Thr Phe Arg Lys Gly Cys Leu Asn Ile Ala Arg
    530                 535                 540

Met Val Pro Leu Met Tyr Ser Tyr Asp Asp Asn His Asn Leu Pro Leu
545                 550                 555                 560

Leu Glu Glu His Met Lys Ala Met Leu Tyr Asp Ser Ser Ser
                565                 570

<210> SEQ ID NO 8
<211> LENGTH: 606
<212> TYPE: PRT
<213> ORGANISM: Mentha citrata

<400> SEQUENCE: 8

Met Cys Thr Ile Ile Ser Val Asn His His Val Ala Ile Leu Ser
1               5                   10                  15

Lys Pro Lys Val Lys Leu Phe His Thr Lys Asn Lys Arg Ser Ala Ser
            20                  25                  30

Ile Asn Leu Pro Trp Ser Leu Ser Pro Ser Ser Ala Ala Ser Arg
        35                  40                  45

Pro Ile Ser Cys Ser Ile Ser Ser Lys Leu Tyr Thr Ile Ser Ser Ala
    50                  55                  60

Gln Glu Glu Thr Arg Arg Ser Gly Asn Tyr His Pro Ser Val Trp Asp
65                  70                  75                  80

Phe Asp Phe Ile Gln Ser Leu Asp Thr Asp His Tyr Lys Glu Glu Lys
                85                  90                  95

Gln Leu Glu Arg Glu Glu Glu Leu Ile Met Glu Val Lys Lys Leu Leu
            100                 105                 110

Gly Ala Lys Met Glu Ala Thr Lys Gln Leu Glu Leu Ile Asp Asp Leu
        115                 120                 125

Gln Asn Leu Gly Leu Ser Tyr Phe Phe Arg Asp Glu Ile Lys Asn Ile
    130                 135                 140
```

```
Leu Asn Ser Ile Tyr Lys Ile Phe Gln Asn Asn Ser Thr Lys Val
145                 150                 155                 160

Gly Asp Leu His Phe Thr Ser Leu Gly Phe Arg Leu Leu Arg Gln His
            165                 170                 175

Gly Phe Asn Val Ser Gln Gly Val Phe Asp Cys Phe Lys Asn Glu His
            180                 185                 190

Gly Ser Asp Phe Glu Lys Thr Leu Ile Gly Glu Asp Thr Lys Gly Val
            195                 200                 205

Leu Gln Leu Tyr Glu Ala Ser Phe Leu Leu Arg Glu Gly Glu Asp Thr
            210                 215                 220

Leu Glu Val Ala Arg Lys Phe Ser Thr Glu Phe Leu Glu Glu Lys Leu
225                 230                 235                 240

Lys Ala Gly Ile Asp Gly Asp Asn Leu Ser Ser Ser Ile Gly His Ser
            245                 250                 255

Leu Glu Ile Pro Leu His Trp Arg Ile Gln Arg Leu Glu Glu Arg Trp
            260                 265                 270

Phe Leu Asp Ala Tyr Ser Arg Arg Lys Asp Met Asn Pro Ile Ile Phe
            275                 280                 285

Glu Leu Ala Lys Leu Asp Phe Asn Ile Ile Gln Ala Thr Gln Gln Glu
            290                 295                 300

Glu Leu Lys Asp Leu Ser Arg Trp Trp Asn Asp Ser Ser Leu Pro Gln
305                 310                 315                 320

Lys Leu Pro Phe Val Arg Asp Arg Leu Val Glu Ser Tyr Tyr Trp Ala
            325                 330                 335

Leu Gly Leu Phe Glu Ala His Lys Phe Gly Tyr Glu Arg Lys Thr Ala
            340                 345                 350

Ala Lys Ile Ile Thr Leu Ile Thr Ala Leu Asp Asp Val Tyr Asp Ile
            355                 360                 365

Tyr Gly Thr Leu Asp Glu Leu Gln Leu Phe Thr His Val Ile Arg Arg
            370                 375                 380

Trp Asp Thr Glu Ser Ala Thr Gln Leu Pro Tyr Tyr Leu Gln Leu Phe
385                 390                 395                 400

Tyr Phe Val Leu Tyr Asn Phe Val Ser Glu Val Ala Tyr His Ile Leu
            405                 410                 415

Lys Glu Glu Gly Phe Ile Ser Ile Pro Phe Leu His Arg Ala Trp Val
            420                 425                 430

Asp Leu Val Glu Gly Tyr Leu Gln Glu Ala Lys Trp Tyr Tyr Thr Lys
            435                 440                 445

Tyr Thr Pro Thr Met Glu Glu Tyr Leu Asn Tyr Ala Ser Ile Thr Ile
            450                 455                 460

Gly Ala Pro Ala Val Ile Ser Gln Ile Tyr Phe Met Leu Ala Lys Ser
465                 470                 475                 480

Lys Glu Lys Pro Val Ile Glu Ser Phe Tyr Glu Tyr Asp Glu Ile Ile
            485                 490                 495

Arg Leu Ser Gly Met Leu Val Arg Leu Pro Asp Asp Leu Gly Thr Leu
            500                 505                 510

Pro Phe Glu Met Lys Arg Gly Asp Val Ala Lys Ser Ile Gln Ile Tyr
            515                 520                 525

Met Lys Glu Gln Asn Ala Thr Arg Glu Glu Ala Glu His Val Arg
            530                 535                 540

Phe Met Ile Arg Glu Ala Trp Lys Glu Met Asn Thr Thr Met Ala Ala
545                 550                 555                 560
```

Asn Ser Asp Leu Arg Gly Asp Val Val Met Ala Ala Asn Leu Gly
            565                 570                 575

Arg Asp Ala Gln Phe Met Tyr Leu Asp Gly Asp Gly Asn His Ser Gln
        580                 585                 590

Leu Gln His Arg Ile Ala Asn Leu Leu Phe Lys Pro Tyr Val
        595                 600                 605

<210> SEQ ID NO 9
<211> LENGTH: 1623
<212> TYPE: DNA
<213> ORGANISM: Artificial sequence
<220> FEATURE:
<223> OTHER INFORMATION: Synthetic nucleic acid sequence

<400> SEQUENCE: 9

| | | | | | |
|---|---|---|---|---|---|
| atgactagaa | gatccggtaa | ttatcaccca | tctgtttggg | atttcgactt | catccaatct | 60 |
| ttggataccg | accactacaa | agaagaaaag | caattggaaa | gagaagaaga | attgatcatg | 120 |
| gaagtcaaaa | agttgttggg | tgctaaaatg | gaagctacca | acaattggaa | attgatcgac | 180 |
| gacttgcaaa | acttgggttt | gtcttacttc | ttcagggacg | aaatcaagaa | catcttgaac | 240 |
| tccatctaca | agatcttcca | aaacaacaac | tctaccaagg | ttggtgactt | gcattttaca | 300 |
| tctttgggtt | tcagattatt | gagacaacac | ggtttcaacg | tttcccaagg | tgttttgat | 360 |
| tgcttcaaga | acgaacacgg | ttccgatttt | gaaaagacct | tgattggtga | agataccaag | 420 |
| ggtgtcttgc | aattatacga | agcttcattc | ttgttgagag | aaggtgaaga | tactttggaa | 480 |
| gttgccagaa | agttctctac | cgaattctta | agaaaaagt | tgaaggccgg | tatcgacggt | 540 |
| gataacttat | cttcttctat | cggtcactcc | ttggaaattc | cattgcattg | gagaattcaa | 600 |
| agattagaag | aaagatggtt | cttggacgcc | tactctagaa | gaaaggatat | gaacccaatc | 660 |
| atcttcgaat | ggccaagtt | ggatttcaac | attattcaag | ccacacaaca | agaagaattg | 720 |
| aaggacttgt | ctagatggtg | gaatgattct | tccttgccac | aaaaattgcc | attcgttaga | 780 |
| gatagattgg | tcgaatctta | ttactgggcc | ttgggtttat | ttgaagctca | taagtttggt | 840 |
| tacgaaagaa | agaccgctgc | caagattatt | actttgatta | ccgctttgga | tgacgtctac | 900 |
| gatatctatg | gtactttgga | cgaattacaa | ttattcaccc | acgtcatcag | aagatgggat | 960 |
| actgaatctg | ctactcaatt | gccttactac | ttgcaattat | tctacttcgt | cttgtacaat | 1020 |
| tcgtcagtg | aagttgccta | ccatatcttg | aagaagaag | gtttcatctc | catcccattc | 1080 |
| ttgcatagag | catgggttga | tttggttgaa | ggttacttgc | aagaagctaa | atggtactac | 1140 |
| actaagtaca | ctccaaccat | ggaagaatac | ttgaactacg | cttctattac | cattggtgct | 1200 |
| ccagctgtta | tttcccaaat | ctactttatg | ttggctaagt | ccaaagaaaa | gccagtcatc | 1260 |
| gaatctttct | acgaatacga | cgaaattatc | agattgtccg | gtatgttggt | tagattgcca | 1320 |
| gatgatttgg | gtactttgcc | tttcgaaatg | aagagaggtg | acgttgctaa | gtctattcaa | 1380 |
| atctacatga | aggaacaaaa | cgccaccaga | gaagaagcag | aagaacacgt | tagattcatg | 1440 |
| attagagaag | cctggaaaga | aatgaacact | actatggctg | ctaactccga | tttgagaggt | 1500 |
| gatgtagtta | tggctgcagc | taatttgggt | agagatgctc | aattcatgta | cttggatggt | 1560 |
| gatggtaacc | actctcaatt | gcaacataga | attgccaact | tgttgttcaa | gccatacgtc | 1620 |
| taa | | | | | | 1623 |

<210> SEQ ID NO 10
<211> LENGTH: 540
<212> TYPE: PRT

<213> ORGANISM: Artificial sequence
<220> FEATURE:
<223> OTHER INFORMATION: Synthetic polypeptide

<400> SEQUENCE: 10

```
Met Thr Arg Arg Ser Gly Asn Tyr His Pro Ser Val Trp Asp Phe Asp
1               5                   10                  15

Phe Ile Gln Ser Leu Asp Thr Asp His Tyr Lys Glu Lys Gln Leu
            20                  25                  30

Glu Arg Glu Glu Glu Leu Ile Met Glu Val Lys Lys Leu Leu Gly Ala
        35                  40                  45

Lys Met Glu Ala Thr Lys Gln Leu Glu Leu Ile Asp Asp Leu Gln Asn
50                  55                  60

Leu Gly Leu Ser Tyr Phe Phe Arg Asp Glu Ile Lys Asn Ile Leu Asn
65                  70                  75                  80

Ser Ile Tyr Lys Ile Phe Gln Asn Asn Ser Thr Lys Val Gly Asp
                85                  90                  95

Leu His Phe Thr Ser Leu Gly Phe Arg Leu Leu Arg Gln His Gly Phe
                100                 105                 110

Asn Val Ser Gln Gly Val Phe Asp Cys Phe Lys Asn Glu His Gly Ser
            115                 120                 125

Asp Phe Glu Lys Thr Leu Ile Gly Glu Asp Thr Lys Gly Val Leu Gln
    130                 135                 140

Leu Tyr Glu Ala Ser Phe Leu Leu Arg Glu Gly Glu Asp Thr Leu Glu
145                 150                 155                 160

Val Ala Arg Lys Phe Ser Thr Glu Phe Leu Glu Glu Lys Leu Lys Ala
                165                 170                 175

Gly Ile Asp Gly Asp Asn Leu Ser Ser Ser Ile Gly His Ser Leu Glu
            180                 185                 190

Ile Pro Leu His Trp Arg Ile Gln Arg Leu Glu Glu Arg Trp Phe Leu
        195                 200                 205

Asp Ala Tyr Ser Arg Arg Lys Asp Met Asn Pro Ile Ile Phe Glu Leu
    210                 215                 220

Ala Lys Leu Asp Phe Asn Ile Ile Gln Ala Thr Gln Gln Glu Glu Leu
225                 230                 235                 240

Lys Asp Leu Ser Arg Trp Trp Asn Asp Ser Ser Leu Pro Gln Lys Leu
                245                 250                 255

Pro Phe Val Arg Asp Arg Leu Val Glu Ser Tyr Tyr Trp Ala Leu Gly
            260                 265                 270

Leu Phe Glu Ala His Lys Phe Gly Tyr Glu Arg Lys Thr Ala Ala Lys
        275                 280                 285

Ile Ile Thr Leu Ile Thr Ala Leu Asp Asp Val Tyr Asp Ile Tyr Gly
    290                 295                 300

Thr Leu Asp Glu Leu Gln Leu Phe Thr His Val Ile Arg Arg Trp Asp
305                 310                 315                 320

Thr Glu Ser Ala Thr Gln Leu Pro Tyr Tyr Leu Gln Leu Phe Tyr Phe
                325                 330                 335

Val Leu Tyr Asn Phe Val Ser Glu Val Ala Tyr His Ile Leu Lys Glu
            340                 345                 350

Glu Gly Phe Ile Ser Ile Pro Phe Leu His Arg Ala Trp Val Asp Leu
        355                 360                 365

Val Glu Gly Tyr Leu Gln Glu Ala Lys Trp Tyr Tyr Thr Lys Tyr Thr
    370                 375                 380

Pro Thr Met Glu Glu Tyr Leu Asn Tyr Ala Ser Ile Thr Ile Gly Ala
```

```
                385                 390                 395                 400
        Pro Ala Val Ile Ser Gln Ile Tyr Phe Met Leu Ala Lys Ser Lys Glu
                        405                 410                 415

Lys Pro Val Ile Glu Ser Phe Tyr Glu Tyr Asp Glu Ile Ile Arg Leu
                        420                 425                 430

Ser Gly Met Leu Val Arg Leu Pro Asp Asp Leu Gly Thr Leu Pro Phe
                        435                 440                 445

Glu Met Lys Arg Gly Asp Val Ala Lys Ser Ile Gln Ile Tyr Met Lys
                        450                 455                 460

Glu Gln Asn Ala Thr Arg Glu Glu Ala Glu His Val Arg Phe Met
        465                 470                 475                 480

Ile Arg Glu Ala Trp Lys Glu Met Asn Thr Thr Met Ala Ala Asn Ser
                        485                 490                 495

Asp Leu Arg Gly Asp Val Val Met Ala Ala Asn Leu Gly Arg Asp
                        500                 505                 510

Ala Gln Phe Met Tyr Leu Asp Gly Asp Gly Asn His Ser Gln Leu Gln
                        515                 520                 525

His Arg Ile Ala Asn Leu Leu Phe Lys Pro Tyr Val
                        530                 535                 540

<210> SEQ ID NO 11
<211> LENGTH: 595
<212> TYPE: PRT
<213> ORGANISM: Thymus vulgaris

<400> SEQUENCE: 11

Met Ser Ala Thr Ile Ser Val Leu His His Ala Thr Ile Leu Pro Lys
        1               5                   10                  15

Pro Ala Asn Asp Val Val Leu Cys Lys Asn Lys Arg Ala Ser Asn Ile
                        20                  25                  30

Asn Pro Trp Thr Pro Ser Leu Ser Ile Ser Ser Lys Leu Asp Thr Lys
                        35                  40                  45

Asn Pro Gly Thr Val Lys Asp Arg Arg Arg Ser Gly Asn Tyr Arg Pro
                        50                  55                  60

Ala Leu Trp Asp Phe Ser Tyr Ile Gln Ser Leu Asn Thr His Asp His
        65                  70                  75                  80

Tyr Asn Lys Glu Val Arg Arg Gly Glu Leu Ile Val Glu Val Lys Lys
                        85                  90                  95

Leu Leu Gly Glu Glu Ile Gly Ala Val Lys Gln Leu Glu Leu Ile Asp
                        100                 105                 110

Asp Leu Lys Asn Leu Gly Leu Ser Tyr Phe Phe Gln Glu Glu Ile Arg
                        115                 120                 125

Asn Val Leu Gly Ser Ile Tyr Ala Glu His Lys Phe Phe Arg Asn Asn
                        130                 135                 140

Gln Val Glu Gly Ser Lys Asp Leu Tyr Phe Thr Ala Leu Gly Phe Arg
        145                 150                 155                 160

Leu Leu Arg Glu Ala Gly Phe Asn Ile Ser Gln Glu Val Phe Asp Arg
                        165                 170                 175

Phe Lys Asn Glu Glu Gly Ser Gly Phe Glu Glu Arg Leu Gly Glu Asp
                        180                 185                 190

Thr Lys Gly Met Leu Gln Leu Tyr Glu Ala Ser Phe Leu Leu Arg Glu
                        195                 200                 205

Gly Glu Asp Thr Leu Glu Leu Ala Arg Gln Ile Ser Thr Glu Phe Leu
                        210                 215                 220
```

```
Lys Glu Lys Leu Asp Gly Thr Glu Ile Ser Asp Gly Asn Leu Ser Ser
225                 230                 235                 240

Ser Ile Arg His Ser Leu Glu Ile Pro Leu His Trp Arg Ile Gln Arg
            245                 250                 255

Leu Glu Ala Arg Trp Phe Leu Asp Ala Tyr Ala Ala Arg Lys Asp Met
        260                 265                 270

Asn Pro Leu Ile Phe Glu Leu Ala Lys Leu Asp Phe Asn Asn Ile Gln
    275                 280                 285

Ala Thr Gln Gln Gln Glu Leu Lys Asp Leu Ser Arg Trp Trp Lys Asn
290                 295                 300

Leu Ser Leu Pro Val Lys Leu Pro Phe Val Arg Asp Arg Leu Val Glu
305                 310                 315                 320

Ser Tyr Phe Trp Ala Val Gly Leu Phe Glu Pro His Lys Phe Gly Tyr
            325                 330                 335

Gln Arg Lys Ile Ala Ala Lys Ile Ile Thr Leu Ile Thr Ser Leu Asp
        340                 345                 350

Asp Val Tyr Asp Ile Tyr Gly Thr Leu Asp Glu Leu Gln Leu Phe Thr
    355                 360                 365

Asp Ala Ile Arg Arg Trp Asp Thr Lys Ser Ala Asn Gln Leu Pro Tyr
370                 375                 380

Tyr Leu Gln Leu Phe Tyr Phe Ala Leu Tyr Thr Phe Val Ser Glu Val
385                 390                 395                 400

Ala Tyr Asp Ile Leu Lys Glu Glu Gly Phe Phe Thr Ile Pro His
            405                 410                 415

Leu Gln Arg Ala Trp Val Asp Leu Val Glu Gly Tyr Leu Gln Glu Ala
        420                 425                 430

Lys Trp Tyr His Ala Asn Tyr Thr Pro Ser Met Glu Glu Tyr Leu Asn
    435                 440                 445

Thr Ala Thr Val Thr Ile Gly Ala Pro Ala Val Ile Ser Gln Val His
450                 455                 460

Phe Val Leu Ala Lys Ser Asn Glu Lys Ala Glu Ser Leu His Glu Tyr
465                 470                 475                 480

Glu Glu Ile Ile Arg Leu Ser Gly Lys Leu Val Arg Leu Pro Asp Asp
            485                 490                 495

Leu Gly Thr Leu Pro Phe Glu Met Lys Arg Gly Asp Val Ala Lys Ser
        500                 505                 510

Ile Gln Ile Tyr Met Lys Glu His Gly Ala Ser Arg Glu Glu Ala Glu
    515                 520                 525

Glu His Val Arg Tyr Glu Ile Arg Glu Ala Trp Lys Glu Met Asn Thr
530                 535                 540

Leu Met Ala Ala Lys Ser Ala Leu Arg Asp Asp Leu Ala Met Val
545                 550                 555                 560

Val Ala Asn Leu Gly Arg Asp Ala Gln Phe Met Tyr Leu Asp Gly Asp
            565                 570                 575

Gly Asn His Ser His Leu Gln His Gln Ile Gln Asn Leu Leu Phe His
        580                 585                 590

Pro Tyr Pro
        595

<210> SEQ ID NO 12
<211> LENGTH: 607
<212> TYPE: PRT
<213> ORGANISM: Perilla frutescens

<400> SEQUENCE: 12
```

```
Met Tyr Ser Leu Arg Ile Tyr Val Ala Ile Met Lys Lys Pro Ser Ala
1               5                   10                  15

Lys His Val Asp Asn Val Asp Lys Lys Ala Ser Lys Pro Ser Trp Arg
            20                  25                  30

Val Ser Leu Ser Ser Ser Ala Gly Leu Arg Ala Ser Ser Ser Leu Gln
                35              40                  45

Leu Asp Val Lys Lys Pro Ala Asp Asp Glu Ile Leu Thr Ala Arg Arg
    50                  55                  60

Ser Gly Asn Tyr Gln Pro Ser Leu Trp Asp Phe Asn Tyr Leu Gln Ser
65                  70                  75                  80

Leu Asn Thr Thr Gln Tyr Lys Glu Val Arg His Leu Lys Arg Glu Ala
                85                  90                  95

Glu Leu Ile Glu Gln Val Lys Met Leu Leu Glu Glu Met Glu Ala
                100                 105                 110

Val Gln Gln Leu Glu Leu Val Asp Asp Leu Lys Asn Leu Gly Leu Ser
                115                 120                 125

Tyr Phe Phe Glu Asp Gln Ile Lys Gln Ile Leu Thr Phe Ile Tyr Asn
        130                 135                 140

Glu His Lys Cys Phe His Ser Asn Ser Ile Ile Glu Ala Glu Glu Ile
145                 150                 155                 160

Arg Asp Leu Tyr Phe Thr Ala Leu Gly Phe Arg Leu Leu Arg Gln His
                165                 170                 175

Gly Phe Gln Val Ser Gln Glu Val Phe Asp Cys Phe Lys Asn Glu Glu
                180                 185                 190

Gly Ser Asp Phe Lys Ala Arg Leu Gly Asp Asp Thr Lys Gly Leu Leu
        195                 200                 205

Gln Leu Tyr Glu Ala Ser Phe Leu Leu Arg Glu Gly Glu Asp Thr Leu
    210                 215                 220

Glu Leu Ala Arg Gln Tyr Ala Thr Lys Phe Leu Gln Lys Lys Val Asp
225                 230                 235                 240

His Glu Leu Ile Asp Asp Asn Asn Leu Leu Ser Trp Ile Leu His Ser
                245                 250                 255

Leu Glu Ile Pro Leu His Trp Arg Ile Gln Arg Leu Glu Ala Arg Trp
                260                 265                 270

Phe Leu Asp Arg Tyr Ala Thr Arg Arg Asp Met Asn Gln Ile Ile Leu
        275                 280                 285

Glu Leu Ala Lys Leu Asp Phe Asn Ile Ile Gln Ala Thr Gln Gln Glu
    290                 295                 300

Glu Leu Lys Asp Leu Ser Arg Trp Trp Lys Ser Thr Cys Leu Ala Glu
305                 310                 315                 320

Lys Leu Pro Phe Val Arg Asp Arg Leu Val Glu Ser Tyr Phe Trp Ala
                325                 330                 335

Ile Ala Leu Phe Glu Pro His Gln Tyr Gly Tyr His Arg Lys Val Ala
        340                 345                 350

Ala Lys Ile Ile Thr Leu Ile Thr Ser Leu Asp Asp Val Tyr Asp Ile
    355                 360                 365

Tyr Gly Thr Leu Asp Glu Leu Gln Leu Phe Thr Asp Ala Ile Gln Arg
    370                 375                 380

Trp Asp Thr Glu Ser Ile Ser Arg Leu Pro Tyr Tyr Met Gln Leu Phe
385                 390                 395                 400

Tyr Met Val Leu Tyr Asn Phe Val Ser Glu Leu Ala Tyr Asp Gly Leu
                405                 410                 415
```

```
Lys Glu Lys Gly Phe Ile Thr Ile Pro Tyr Leu Gln Arg Ser Trp Ala
            420                 425                 430

Asp Leu Val Glu Ala Tyr Leu Lys Glu Ala Lys Trp Phe Tyr Asn Gly
                435                 440                 445

Tyr Val Pro Ser Met Glu Tyr Leu Asn Asn Ala Tyr Ile Ser Ile
            450                 455                 460

Gly Ala Thr Pro Val Ile Ser Gln Val Phe Phe Thr Leu Ala Thr Ser
465                 470                 475                 480

Ile Asp Lys Pro Val Ile Asp Ser Leu Tyr Glu Tyr His Arg Ile Leu
                485                 490                 495

Arg Leu Ser Gly Met Leu Val Arg Leu Pro Asp Asp Leu Gly Thr Ser
            500                 505                 510

Pro Phe Glu Met Lys Arg Gly Asp Val Pro Lys Ala Ile Gln Leu Tyr
            515                 520                 525

Met Lys Glu Arg Asn Ala Thr Glu Ile Glu Ala Gln Glu His Val Arg
            530                 535                 540

Phe Leu Ile Arg Glu Ala Trp Lys Glu Met Asn Thr Val Thr Thr Ala
545                 550                 555                 560

Ala Asp Cys Pro Phe Thr Asp Asp Leu Val Ala Ala Thr Arg Asn Leu
                565                 570                 575

Gly Arg Ala Ala Gln Phe Met Tyr Leu Asp Gly Asp Gly Asn His Ser
            580                 585                 590

Gln Leu His Gln Arg Ile Ala Cys Leu Leu Phe Glu Pro Tyr Ala
            595                 600                 605

<210> SEQ ID NO 13
<211> LENGTH: 609
<212> TYPE: PRT
<213> ORGANISM: Solanum lysopersicum

<400> SEQUENCE: 13

Met Val Ser Ile Leu Ser Asn Ile Gly Met Met Val Val Thr Phe Lys
1               5                   10                  15

Arg Pro Ser Leu Phe Thr Ser Leu Arg Arg Arg Ser Ala Asn Asn Ile
            20                  25                  30

Ile Ile Thr Lys His Ser His Pro Ile Ser Thr Thr Arg Arg Ser Gly
        35                  40                  45

Asn Tyr Lys Pro Thr Met Trp Asp Phe Gln Phe Ile Gln Ser Leu His
    50                  55                  60

Asn Pro Tyr Glu Gly Asp Lys Tyr Met Lys Arg Leu Asn Lys Leu Lys
65                  70                  75                  80

Lys Glu Val Lys Lys Met Met Met Thr Val Glu Gly Ser His Asp Glu
                85                  90                  95

Glu Leu Glu Lys Leu Glu Leu Ile Asp Asn Leu Glu Arg Leu Gly Val
            100                 105                 110

Ser Tyr His Phe Lys Asp Glu Ile Met Gln Ile Met Arg Ser Ile Asn
        115                 120                 125

Ile Asn Ile Asn Ile Ala Pro Pro Asp Ser Leu Tyr Thr Thr Ala Leu
    130                 135                 140

Lys Phe Arg Leu Leu Arg Gln His Gly Phe His Ile Ser Gln Asp Ile
145                 150                 155                 160

Leu Asn Asp Phe Lys Asp Glu Asn Gly Asn Leu Lys Gln Ser Ile Cys
                165                 170                 175

Lys Asp Thr Lys Asp Ile Leu Asn Ser Ser Lys Asp Glu His Asp Asn
            180                 185                 190
```

```
Leu Lys Gln Ser Thr Cys Asn Asn Thr Lys Gly Leu Leu Lys Leu Tyr
        195                 200                 205

Glu Ala Ser Phe Leu Ser Ile Glu Asn Glu Ser Phe Leu Arg Asn Thr
    210                 215                 220

Thr Lys Ser Thr Leu Ala His Leu Met Arg Tyr Val Asp Gln Asn Arg
225                 230                 235                 240

Cys Gly Glu Glu Asp Asn Met Ile Val Glu Leu Val His Ala Leu
                245                 250                 255

Glu Leu Pro Arg His Trp Met Val Pro Arg Leu Glu Thr Arg Trp Tyr
            260                 265                 270

Ile Ser Ile Tyr Glu Arg Met Ser Asn Ala Asn Pro Leu Leu Leu Glu
        275                 280                 285

Leu Ala Lys Leu Asp Phe Asn Ile Val Gln Ala Thr His Gln Gln Asp
    290                 295                 300

Leu Arg Ile Leu Ser Arg Trp Trp Lys Asn Thr Gly Leu Ala Glu Lys
305                 310                 315                 320

Leu Pro Phe Ser Arg Asp Ile Leu Val Glu Asn Met Phe Trp Ala Val
                325                 330                 335

Gly Ala Leu Phe Glu Pro Gln His Ser Tyr Phe Arg Arg Leu Ile Thr
            340                 345                 350

Lys Val Ile Val Phe Ile Ser Ile Ile Asp Asp Ile Tyr Asp Val Tyr
        355                 360                 365

Gly Thr Leu Asp Glu Leu Glu Leu Phe Thr Leu Ala Ile Gln Arg Trp
    370                 375                 380

Asp Thr Lys Ala Met Glu Gln Leu Pro Asp Tyr Met Lys Val Cys Tyr
385                 390                 395                 400

Leu Ala Leu Ile Asn Ile Ile Asn Glu Val Ala Tyr Glu Val Leu Lys
                405                 410                 415

Asn His Asp Ile Asn Val Leu Pro Tyr Leu Thr Lys Ser Trp Ala Asp
            420                 425                 430

Leu Cys Lys Ser Tyr Leu Gln Glu Ala Lys Trp Tyr His Asn Gly Tyr
        435                 440                 445

Lys Pro Asn Leu Glu Glu Tyr Met Asp Asn Ala Arg Ile Ser Ile Gly
    450                 455                 460

Val Pro Met Val Leu Val His Ser Leu Phe Leu Val Thr Asn Gln Ile
465                 470                 475                 480

Thr Lys Glu Ala Leu Asp Ser Leu Thr Asn Tyr Pro Asp Ile Ile Arg
                485                 490                 495

Trp Ser Ala Thr Ile Phe Arg Leu Asn Asp Asp Leu Gly Thr Ser Ser
            500                 505                 510

Asp Glu Leu Lys Arg Gly Asp Val Ser Lys Ser Ile Gln Cys Tyr Met
        515                 520                 525

Asn Glu Lys Gly Ala Ser Glu Glu Ala Ile Glu His Ile Glu Phe
    530                 535                 540

Leu Ile Gln Glu Thr Trp Glu Ala Met Asn Thr Ala Gln Ser Lys Asn
545                 550                 555                 560

Ser Pro Leu Ser Glu Thr Phe Ile Glu Val Ala Lys Asn Ile Thr Lys
                565                 570                 575

Ala Ser His Phe Met Tyr Leu His Ser Asp Val Lys Ser Ser Ile Ser
            580                 585                 590

Lys Ile Leu Phe Glu Pro Ile Ile Ile Ser Asn Val Ala Phe Ala Leu
        595                 600                 605
```

Lys

<210> SEQ ID NO 14
<211> LENGTH: 602
<212> TYPE: PRT
<213> ORGANISM: Perilla citriodora

<400> SEQUENCE: 14

Met Ser Ser Ile Arg Ile Tyr Val Ala Ile Met Lys Lys Pro Ser Val
1               5                   10                  15

Lys His Val Asp Asn Val Asp Lys Lys Ala Ser Lys Ser Ser Trp Arg
            20                  25                  30

Val Ser Ser Ala Gly Leu Arg Ala Ser Ser Ser Gln Leu Asp
        35                  40                  45

Val Lys Lys Pro Ala Asp Glu Ile Leu Thr Ala Arg Arg Ser Gly Asn
    50                  55                  60

Tyr Gln Pro Ser Leu Trp Asp Phe Asn Tyr Leu Arg Ser Leu Asn Thr
65                  70                  75                  80

Thr His Tyr Lys Glu Glu Arg His Leu Lys Arg Glu Ala Glu Leu Ile
                85                  90                  95

Glu Gln Val Lys Met Leu Leu Asp Glu Glu Met Glu Ala Val Gln Gln
            100                 105                 110

Leu Glu Leu Val Asp Asp Leu Lys Asn Leu Gly Leu Ser Tyr Phe Phe
        115                 120                 125

Glu Asp Gln Ile Lys Gln Ile Leu Thr Phe Ile Tyr Asn Glu His Glu
    130                 135                 140

Cys Phe Arg Ser Asn Val Glu Ala Glu Arg Asp Leu Tyr Phe Thr
145                 150                 155                 160

Ala Leu Gly Phe Arg Leu Leu Arg Gln His Ser Leu Gln Val Ser Gln
                165                 170                 175

Glu Val Phe Asp Cys Phe Lys Asn Glu Glu Gly Ser Asp Phe Lys Ala
            180                 185                 190

Ser Leu Gly Asp Asp Thr Lys Gly Leu Val Gln Leu Tyr Glu Ala Ser
        195                 200                 205

Phe Leu Leu Arg Glu Gly Glu Asp Thr Leu Glu Leu Ala Arg Gln Tyr
    210                 215                 220

Ala Thr Lys Phe Leu Gln Lys Lys Val Asp His Glu Leu Ile Asp Asp
225                 230                 235                 240

Asp Asn Asn Leu Leu Ser Trp Ile Arg His Ser Leu Glu Ile Pro Leu
                245                 250                 255

His Trp Arg Ile Gln Arg Leu Glu Ala Arg Trp Phe Leu Asp Ala Tyr
            260                 265                 270

Ala Met Arg His Asp Val Asn Pro Ile Ile Leu Glu Leu Ala Lys Leu
        275                 280                 285

Asp Phe Asn Ile Ile Gln Ala Thr Gln Gln Glu Glu Leu Lys Asp Leu
    290                 295                 300

Ser Arg Trp Trp Asn Ser Thr Cys Leu Ala Glu Lys Leu Pro Phe Val
305                 310                 315                 320

Arg Asp Arg Leu Val Glu Ser Tyr Phe Trp Ala Ile Ala Leu Phe Glu
                325                 330                 335

Pro His Gln Phe Gly Tyr His Arg Lys Ile Ala Ala Lys Ile Ile Thr
            340                 345                 350

Leu Ile Thr Ser Leu Asp Asp Val Tyr Asp Ile Tyr Gly Thr Leu Asp
        355                 360                 365

```
Glu Leu Gln Leu Phe Thr Asp Ala Ile Gln Arg Trp Asp Thr Glu Ser
370                 375                 380

Ile Ser Arg Leu Pro Tyr Tyr Met Gln Leu Phe Tyr Met Val Leu Tyr
385                 390                 395                 400

Asn Phe Ile Ser Glu Leu Ala Tyr Asp Gly Leu Lys Glu Lys Gly Phe
                405                 410                 415

Ile Thr Ile Pro Tyr Leu Gln Arg Ser Trp Ala Asp Leu Val Glu Ala
                420                 425                 430

Tyr Leu Lys Glu Ala Lys Trp Phe Tyr Asn Gly Tyr Thr Pro Ser Met
                435                 440                 445

Glu Glu Tyr Leu Asn Asn Ala Tyr Ile Ser Ile Gly Ala Thr Pro Val
450                 455                 460

Ile Ser Gln Val Phe Phe Thr Leu Ala Thr Ser Ile Asp Lys Pro Val
465                 470                 475                 480

Ile Glu Ser Leu Tyr Glu Tyr His Arg Ile Leu Arg Leu Ser Gly Met
                485                 490                 495

Leu Val Arg Leu Pro Asp Asp Leu Gly Thr Ser Ser Phe Glu Met Arg
                500                 505                 510

Arg Gly Asp Val Pro Lys Ala Ile Glu Leu Tyr Met Lys Glu Arg Asn
                515                 520                 525

Ala Thr Glu Ile Glu Ala Gln Glu His Val Arg Phe Leu Ile Arg Glu
530                 535                 540

Ala Trp Lys Glu Met Asn Thr Ala Thr Thr Val Ala Asp Cys Pro Phe
545                 550                 555                 560

Thr Asp Asp Leu Val Ala Ala Ala Asn Leu Gly Arg Ala Ala Gln
                565                 570                 575

Phe Met Tyr Leu Asp Gly Asp Gly Asn His Ser Gln Leu His Gln Arg
                580                 585                 590

Ile Ala Ser Leu Leu Phe Glu Gln Tyr Ala
                595                 600

<210> SEQ ID NO 15
<211> LENGTH: 1509
<212> TYPE: DNA
<213> ORGANISM: Artificial sequence
<220> FEATURE:
<223> OTHER INFORMATION: Synthetic nucleic acid sequence

<400> SEQUENCE: 15
atggttttaa ccaataaaac agtcatttct ggatcgaaag tcaaaagttt atcatctgcg      60
caatcgagct catcaggacc ttcatcatct agtgaggaag atgattcccg cgatattgaa     120
agcttggata gaaaatacg tcctttagaa gaattagaag cattattaag tagtggaaat     180 acaaacaat tgaagaacaa agaggtcgct gccttggtta ttcacggtaa gttacctttg     240
tacgctttgg agaaaaaatt aggtgatact acgagagcgg ttgcggtacg taggaaggct     300
ctttcaattt tggcagaagc tcctgtatta gcatctgatc gtttaccata taaaaattat     360
gactacgacc gcgtatttgg cgcttgttgt gaaaatgtta taggttacat gcctttgccc     420
gttggtgtta taggcccctt ggttatcgat ggtacatctt atcatatacc aatggcaact     480
acagagggtt gtttggtagc ttctgccatg cgtggctgta aggcaatcaa tgctggcggt     540
ggtgcaacaa ctgttttaac taaggatggt atgacaagag gcccagtagt ccgtttccca     600
actttgaaaa gatctggtgc ctgtaagata tggttagact cagaagaggg acaaaacgca     660
attaaaaaag cttttaactc tacatcaaga tttgcacgtc tgcaacatat tcaaacttgt     720
```

```
ctagcaggag atttactctt catgagattt agaacaacta ctggtgacgc aatgggtatg    780
aatatgattt ctaaaggtgt cgaatactca ttaaagcaaa tggtagaaga gtatggctgg    840
gaagatatgg aggttgtctc cgtttctggt aactactgta ccgacaaaaa accagctgcc    900
atcaactgga tcgaaggtcg tggtaagagt gtcgtcgcag aagctactat tcctggtgat    960
gttgtcagaa aagtgttaaa aagtgatgtt tccgcattgg ttgagttgaa cattgctaag   1020
aatttggttg gatctgcaat ggctgggtct gttggtggat ttaacgcaca tgcagctaat   1080
ttagtgacag ctgttttctt ggcattagga caagatcctg cacaaaatgt tgaaagttcc   1140
aactgtataa cattgatgaa agaagtggac ggtgatttga gaatttccgt atccatgcca   1200
tccatcgaag taggtaccat cggtggtggt actgttctag aaccacaagg tgccatgttg   1260
gacttattag gtgtaagagg cccgcatgct accgctcctg gtaccaacgc acgtcaatta   1320
gcaagaatag ttgcctgtgc cgtcttggca ggtgaattat ccttatgtgc tgccctagca   1380
gccggccatt tggttcaaag tcatatgacc cacaacagga aacctgctga accaacaaaa   1440
cctaacaatt tggacgccac tgatataaat cgtttgaaag atgggtccgt cacctgcatt   1500
aaatcctaa                                                          1509
```

<210> SEQ ID NO 16
<211> LENGTH: 502
<212> TYPE: PRT
<213> ORGANISM: Artificial sequence
<220> FEATURE:
<223> OTHER INFORMATION: Synthetic polypeptide

<400> SEQUENCE: 16

```
Met Val Leu Thr Asn Lys Thr Val Ile Ser Gly Ser Lys Val Lys Ser
1               5                   10                  15

Leu Ser Ser Ala Gln Ser Ser Ser Gly Pro Ser Ser Ser Ser Ser Glu
            20                  25                  30

Glu Asp Asp Ser Arg Asp Ile Glu Ser Leu Asp Lys Lys Ile Arg Pro
        35                  40                  45

Leu Glu Glu Leu Glu Ala Leu Leu Ser Ser Gly Asn Thr Lys Gln Leu
    50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Gly Ala Cys
        195                 200                 205

Lys Ile Trp Leu Asp Ser Glu Glu Gly Gln Asn Ala Ile Lys Lys Ala
    210                 215                 220
```

```
Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
            245                 250                 255

Ala Met Gly Met Asn Met Ile Ser Lys Gly Val Glu Tyr Ser Leu Lys
        260                 265                 270

Gln Met Val Glu Glu Tyr Gly Trp Glu Asp Met Glu Val Val Ser Val
    275                 280                 285

Ser Gly Asn Tyr Cys Thr Asp Lys Lys Pro Ala Ala Ile Asn Trp Ile
290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
            340                 345                 350

Gly Phe Asn Ala His Ala Ala Asn Leu Val Thr Ala Val Phe Leu Ala
        355                 360                 365

Leu Gly Gln Asp Pro Ala Gln Asn Val Glu Ser Ser Asn Cys Ile Thr
    370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Gly Thr Val Leu Glu Pro Gln
                405                 410                 415

Gly Ala Met Leu Asp Leu Leu Gly Val Arg Gly Pro His Ala Thr Ala
            420                 425                 430

Pro Gly Thr Asn Ala Arg Gln Leu Ala Arg Ile Val Ala Cys Ala Val
        435                 440                 445

Leu Ala Gly Glu Leu Ser Leu Cys Ala Ala Leu Ala Ala Gly His Leu
    450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
                485                 490                 495

Val Thr Cys Ile Lys Ser
            500

<210> SEQ ID NO 17
<211> LENGTH: 352
<212> TYPE: PRT
<213> ORGANISM: Saccharomyces cerevisiae

<400> SEQUENCE: 17

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
```

```
            85                  90                  95
Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
            115                 120                 125

Ala Phe Met Leu Glu Ala Ala Ile Tyr Lys Leu Leu Lys Ser His Phe
            130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
            165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
            195                 200                 205

Leu Ala Met Tyr Val Ala Gly Ile Thr Asp Glu Lys Asp Leu Lys Gln
            210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
            245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
            275                 280                 285

Lys Lys Asp Ser Val Ala Glu Ala Lys Cys Lys Lys Ile Phe Asn Asp
            290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
            325                 330                 335

Ala Asp Val Leu Thr Ala Phe Leu Asn Lys Val Tyr Lys Arg Ser Lys
            340                 345                 350

<210> SEQ ID NO 18
<211> LENGTH: 352
<212> TYPE: PRT
<213> ORGANISM: Artificial sequence
<220> FEATURE:
<223> OTHER INFORMATION: Synthetic polypeptide

<400> SEQUENCE: 18

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
            35                  40                  45

Pro Gly Gly Lys Leu Asn Arg Gly Leu Ser Val Val Asp Thr Tyr Ala
            50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Trp
            85                  90                  95

Leu Val Ala Asp Asp Met Met Asp Lys Ser Ile Thr Arg Arg Gly Gln
```

```
                    100                 105                 110
Pro Cys Trp Tyr Lys Val Pro Glu Val Gly Glu Ile Ala Ile Trp Asp
            115                 120                 125

Ala Phe Met Leu Glu Ala Ala Ile Tyr Lys Leu Leu Lys Ser His Phe
        130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
        210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
                260                 265                 270

Glu Leu Ala Ser Ala Glu Gln Arg Lys Thr Leu Asp Glu Asn Tyr Gly
            275                 280                 285

Lys Lys Asp Ser Val Ala Glu Ala Lys Cys Lys Lys Ile Phe Asn Asp
        290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 19
<211> LENGTH: 352
<212> TYPE: PRT
<213> ORGANISM: Artificial sequence
<220> FEATURE:
<223> OTHER INFORMATION: Synthetic polypeptide

<400> SEQUENCE: 19

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
```

```
            115                 120                 125
Ala Phe Met Leu Glu Ala Ala Ile Tyr Lys Leu Leu Lys Ser His Phe
            130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                    165                 170                 175

Glu Asp Lys Val Asp Leu Ser Lys Phe Ser Leu Lys Lys His Ser Phe
                180                 185                 190

Ile Val Thr Phe Ala Thr Ala Tyr Tyr Ser Phe Tyr Leu Pro Val Ala
                    195                 200                 205

Leu Ala Met Tyr Val Ala Gly Ile Thr Asp Glu Lys Asp Leu Lys Gln
            210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                    245                 250                 255

Thr Asp Ile Gln Asp Asn Lys Cys Ser Trp Val Ile Asn Lys Ala Leu
                260                 265                 270

Glu Leu Ala Ser Ala Glu Gln Arg Lys Thr Leu Asp Glu Asn Tyr Gly
            275                 280                 285

Lys Lys Asp Ser Val Ala Glu Ala Lys Cys Lys Lys Ile Phe Asn Asp
290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
                    325                 330                 335

Ala Asp Val Leu Thr Ala Phe Leu Asn Lys Val Tyr Lys Arg Ser Lys
                340                 345                 350

<210> SEQ ID NO 20
<211> LENGTH: 603
<212> TYPE: PRT
<213> ORGANISM: Perilla citriodora geraniol

<400> SEQUENCE: 20

Met Ser Ser Ile Ser Gln Lys Val Val Ile Gly Leu Asn Lys Ala Ala
1               5                   10                  15

Ala Asn Asn Asn Leu Gln Asn Leu Asp Arg Arg Gly Phe Lys Thr Arg
            20                  25                  30

Cys Val Ser Ser Ser Lys Ala Ala Ser Cys Leu Arg Ala Ser Cys Ser
        35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Pro Ala Gln Gln Leu
            100                 105                 110

Glu Leu Ile Asp Asp Leu Asn Asn Leu Gly Leu Ser Tyr Phe Phe Gln
        115                 120                 125

Asp Arg Ile Lys Gln Ile Leu Ser Phe Ile Tyr Asp Glu Asn Gln Cys
    130                 135                 140
```

```
Phe His Ser Asn Ile Asn Asp Gln Ala Glu Lys Arg Asp Leu Tyr Phe
145                 150                 155                 160

Thr Ala Leu Gly Phe Arg Leu Leu Arg Gln His Gly Phe Asp Val Ser
            165                 170                 175

Gln Glu Val Phe Asp Cys Phe Lys Asn Asp Asn Gly Ser Asp Phe Lys
                180                 185                 190

Ala Ser Leu Ser Asp Asn Thr Lys Gly Leu Leu Gln Leu Tyr Glu Ala
        195                 200                 205

Ser Phe Leu Val Arg Glu Gly Glu Asp Thr Leu Glu Gln Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Cys Ile His His Ser Leu Glu Ile Pro Leu His Trp
                245                 250                 255

Arg Ile Gln Arg Leu Glu Ala Arg Trp Phe Leu Asp Ala Tyr Ala Thr
                260                 265                 270

Arg His Asp Met Asn Pro Val Ile Leu Glu Leu Ala Lys Leu Asp Phe
            275                 280                 285

Asn Ile Ile Gln Ala Thr His Gln Glu Glu Leu Lys Asp Val Ser Arg
290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335

Gln Tyr Gly Tyr Gln Arg Arg Val Ala Ala Lys Ile Ile Thr Leu Ala
            340                 345                 350

Thr Ser Ile Asp Asp Val Tyr Asp Ile Tyr Gly Thr Leu Asp Glu Leu
            355                 360                 365

Gln Leu Phe Thr Asp Asn Phe Arg Arg Trp Asp Thr Glu Ser Leu Gly
        370                 375                 380

Arg Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Val
                405                 410                 415

Ile Pro Tyr Leu Gln Arg Ser Trp Val Asp Leu Ala Glu Ser Phe Leu
            420                 425                 430

Lys Glu Ala Asn Trp Tyr Tyr Ser Gly Tyr Thr Pro Ser Leu Glu Glu
        435                 440                 445

Tyr Ile Asp Asn Gly Ser Ile Ser Ile Gly Ala Val Ala Val Leu Ser
    450                 455                 460

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
                485                 490                 495

Arg Leu His Asp Asp Leu Gly Thr Ser Leu Phe Glu Lys Lys Arg Gly
            500                 505                 510

Asp Val Pro Lys Ala Val Glu Ile Cys Met Lys Glu Arg Asn Val Thr
        515                 520                 525

Glu Glu Glu Ala Glu His Val Lys Tyr Leu Ile Arg Glu Ala Trp
    530                 535                 540

Lys Glu Met Asn Thr Ala Thr Thr Ala Ala Gly Cys Pro Phe Met Asp
545                 550                 555                 560

Glu Leu Asn Val Ala Ala Ala Asn Leu Gly Arg Ala Ala Gln Phe Val
```

```
                       565                 570                 575
Tyr Leu Asp Gly Asp Gly His Gly Val Gln His Ser Lys Ile His Gln
                   580                 585                 590

Gln Met Gly Gly Leu Met Phe Glu Pro Tyr Val
                   595                 600

<210> SEQ ID NO 21
<211> LENGTH: 603
<212> TYPE: PRT
<213> ORGANISM: Perilla frutescens

<400> SEQUENCE: 21

Met Ser Ser Ile Ser Gln Lys Val Val Ile Gly Leu Asn Lys Ala Ala
1               5                   10                  15

Ala Asn Asn Leu Gln Asn Leu Asp Arg Arg Gly Phe Lys Thr Arg
                20                  25                  30

Cys Val Ser Ser Lys Ala Ala Ser Cys Leu Arg Ala Ser Cys Ser
            35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile Val
                85                  90                  95

Gln Val Lys Pro Leu Leu Glu Lys Lys Met Glu Ala Ala Gln Gln Leu
            100                 105                 110

Glu Leu Ile Asp Asp Leu Asn Asn Leu Gly Leu Ser Tyr Phe Phe Gln
        115                 120                 125

Asp Arg Ile Lys Gln Ile Leu Ser Phe Ile Tyr Asp Glu Asn Gln Cys
    130                 135                 140

Phe His Ser Asn Ile Asn Asp Gln Ala Glu Lys Arg Asp Leu Tyr Phe
145                 150                 155                 160

Thr Ala Leu Gly Phe Arg Ile Leu Arg Gln His Gly Phe Asp Val Ser
                165                 170                 175

Gln Glu Val Phe Asp Cys Phe Lys Asn Asp Ser Gly Ser Asp Phe Lys
            180                 185                 190

Ala Ser Leu Ser Asp Asn Thr Lys Gly Leu Leu Gln Leu Tyr Glu Ala
        195                 200                 205

Ser Phe Leu Val Arg Glu Gly Glu Asp Thr Leu Glu Gln Ala Arg Gln
    210                 215                 220

Phe Ala Thr Lys Phe Leu Arg Arg Lys Leu Asp Glu Ile Asp Asp Asn
225                 230                 235                 240

His Leu Leu Ser Cys Ile His His Ser Leu Glu Ile Pro Leu His Trp
                245                 250                 255

Arg Ile Gln Arg Leu Glu Ala Arg Trp Phe Leu Asp Ala Tyr Ala Thr
            260                 265                 270

Arg His Asp Met Asn Pro Val Ile Leu Glu Leu Ala Lys Leu Asp Phe
        275                 280                 285

Asn Ile Ile Gln Ala Thr His Gln Glu Glu Leu Lys Asp Val Ser Arg
    290                 295                 300

Trp Trp Gln Asn Thr Arg Leu Ala Glu Lys Leu Pro Phe Val Arg Asp
305                 310                 315                 320

Arg Leu Val Glu Ser Tyr Phe Trp Ala Ile Ala Leu Phe Glu Pro His
                325                 330                 335
```

Gln Tyr Gly Tyr Gln Arg Arg Val Ala Ala Lys Ile Ile Thr Leu Ala
                340                 345                 350

Thr Ser Ile Asp Asp Val Tyr Asp Ile Tyr Gly Thr Leu Asp Glu Leu
            355                 360                 365

Gln Leu Phe Thr Asp Asn Phe Arg Arg Trp Asp Thr Glu Ser Leu Gly
        370                 375                 380

Arg Leu Pro Tyr Ser Met Gln Leu Phe Tyr Met Val Ile His Asn Phe
385                 390                 395                 400

Val Ser Glu Leu Ala Tyr Glu Ile Leu Lys Glu Lys Gly Phe Ile Val
                405                 410                 415

Ile Pro Tyr Leu Gln Arg Ser Trp Val Asp Leu Ala Glu Ser Phe Leu
            420                 425                 430

Lys Glu Ala Asn Trp Tyr Tyr Ser Gly Tyr Thr Pro Ser Leu Glu Glu
        435                 440                 445

Tyr Ile Asp Asn Gly Ser Ile Ser Ile Gly Ala Val Ala Val Leu Ser
450                 455                 460

Gln Val Tyr Phe Thr Leu Ala Asn Ser Ile Glu Lys Pro Lys Ile Glu
465                 470                 475                 480

Ser Met Tyr Lys Tyr His His Ile Leu Arg Leu Ser Gly Leu Leu Val
                485                 490                 495

Arg Leu His Asp Asp Leu Gly Thr Ser Leu Phe Glu Lys Lys Arg Gly
            500                 505                 510

Asp Val Pro Lys Ala Val Glu Ile Cys Met Lys Glu Arg Asn Val Thr
        515                 520                 525

Glu Glu Glu Ala Glu Glu His Val Lys Tyr Leu Ile Arg Glu Ala Trp
530                 535                 540

Lys Glu Met Asn Thr Ala Thr Thr Ala Ala Gly Cys Pro Phe Met Asp
545                 550                 555                 560

Glu Leu Asn Val Ala Ala Ala Asn Leu Gly Arg Ala Ala Gln Phe Val
                565                 570                 575

Tyr Leu Asp Gly Asp Gly His Gly Val Gln His Ser Lys Ile His Gln
            580                 585                 590

Gln Met Gly Gly Leu Met Phe Glu Pro Tyr Val
        595                 600

<210> SEQ ID NO 22
<211> LENGTH: 594
<212> TYPE: PRT
<213> ORGANISM: Camptotheca acuminate

<400> SEQUENCE: 22

Met Ala Cys Met Ser Val Ser Ser Leu Ser Gln Ser Thr Arg Ile Ser
1               5                   10                  15

Thr His Cys Asn Ile Ile Gly Arg Phe Gly Val Pro Ser Arg Gly Leu
                20                  25                  30

Ser Gln Trp Ile Lys Thr Ser Ser Ser Ser Ser Ser Leu Arg Ser
            35                  40                  45

Ser Ser Trp His Cys Met Cys Thr Thr Leu Pro Ser Pro Ala Thr Ser
        50                  55                  60

Thr Ala Thr Ile Gly Asp Thr Asp Ser Leu Leu Lys Ser Gln Arg Gln
65                  70                  75                  80

Phe Thr Val Tyr Leu Pro Ala His Glu Ala Asp Lys Asp Arg Lys Ile
                85                  90                  95

Glu Glu Ile Met Glu Lys Thr Gln Gly Glu Leu Glu Lys Thr Ser Asp
                100                 105                 110

-continued

```
Pro Thr Ser Val Met Lys Phe Ile Asp Thr Leu Glu Arg Leu Gly Ile
            115                 120                 125

Ala Tyr His Phe Glu Glu Ile Asn Ser Leu Leu Gln Gly Phe Leu
    130                 135                 140

Ala Asn Gly Tyr Ser His Tyr Pro Gln Asp Leu Phe Thr Thr Ala Leu
145                 150                 155                 160

Arg Phe Arg Leu Leu Arg His Asn Gly Tyr His Ile Ser Ala Asp Val
                165                 170                 175

Phe Gln Lys Phe Val Asp Lys Asn Gly Lys Phe Lys Glu Ser Leu Arg
                180                 185                 190

Glu Asp Thr Gln Gly Met Leu Ser Leu Tyr Glu Ala Ser Tyr Leu Gly
            195                 200                 205

Ala Asn Gly Glu Asp Ile Leu Ser Gln Ala Met Glu Phe Thr Glu Thr
        210                 215                 220

His Phe Lys Gln Ser Ile Pro Leu Met Ala Ala Val Pro Gln Leu Glu
225                 230                 235                 240

Gln Ala Leu Glu Leu Pro Arg His Leu Arg Met Ala Arg Leu Glu Ala
                245                 250                 255

Arg Arg Phe Ile Glu Glu Tyr Ile Arg Glu Ser Asp His Ser Ser Ala
                260                 265                 270

Leu Leu Glu Leu Ala Lys Leu Asp Tyr Asn Lys Val Gln Leu Leu His
            275                 280                 285

Gln Ser Glu Leu Asn Glu Ile Ser Arg Trp Trp Lys Gln Leu Gly Leu
        290                 295                 300

Val Glu Asn Leu Gly Phe Gly Arg Asp Arg Pro Leu Glu Cys Phe Leu
305                 310                 315                 320

Trp Thr Val Gly Ile Leu Pro Glu Pro Lys Tyr Ser Gly Cys Arg Ile
                325                 330                 335

Glu Leu Thr Lys Thr Ile Ala Val Leu Leu Val Leu Asp Asp Ile Phe
            340                 345                 350

Asp Ser Phe Gly Thr Leu Asp Glu Leu Val Arg Phe Thr His Ala Ile
        355                 360                 365

Arg Arg Trp Asp Leu Ser Ala Met Glu Gln Leu Pro Gly Tyr Met Lys
    370                 375                 380

Val Cys Tyr Met Ala Leu Tyr Asn Thr Thr Asn Glu Ile Gly Tyr Lys
385                 390                 395                 400

Ile Leu Lys Glu His Gly Trp Asn Val Val Pro Tyr Leu Lys Arg Thr
                405                 410                 415

Trp Ile Asp Met Ile Glu Gly Phe Gln Ala Glu Ala Asn Trp Cys Ser
            420                 425                 430

Ser Gly Tyr Val Pro Ser Leu Glu Glu Tyr Ile Glu Asn Gly Val Thr
        435                 440                 445

Thr Ala Gly Ser Tyr Met Ala Leu Val His Leu Phe Phe Leu Met Gly
    450                 455                 460

Gln Gly Val Thr Asp Glu Thr Ile Gly Met Leu Glu Pro Tyr Pro Lys
465                 470                 475                 480

Phe Phe Ser Ser Ser Gly Arg Ile Leu Arg Leu Trp Asp Asp Leu Gly
                485                 490                 495

Thr Ala Ser Glu Glu Gln Glu Arg Gly Asp Ile Ala Ser Ser Ile Glu
            500                 505                 510

Leu Phe Met Arg Glu Lys Asp Leu Ser Ser Gln Gly Glu Ala Arg Lys
        515                 520                 525
```

Tyr Val Lys Gln Val Ile Tyr Ser Leu Trp Lys Glu Leu Asn Gly Glu
530                 535                 540

Leu Met Ala Ser Lys Ala Met Pro Leu Pro Leu Ile Lys Ala Ala Phe
545                 550                 555                 560

Asn Met Ala Arg Thr Ser Gln Val Ile Tyr Gln His Gly Asp Asp Asn
                565                 570                 575

Ser Phe Pro Ser Val Asp Gln Cys Val Gln Ser Leu Phe Phe Thr Pro
            580                 585                 590

Ile Leu

<210> SEQ ID NO 23
<211> LENGTH: 612
<212> TYPE: PRT
<213> ORGANISM: Citrus jambhiri

<400> SEQUENCE: 23

Met Ser Ser Ser Ile Asn Pro Ser Thr Leu Val Thr Ser Val Asn Gly
1               5                   10                  15

Phe Lys Cys Leu Pro Leu Thr Thr Asn Lys Ala Ala Ile Arg Ile Met
                20                  25                  30

Ala Lys Asn Lys Pro Leu Gln Cys Leu Val Ser Ala Lys Tyr Asp Asn
            35                  40                  45

Leu Thr Val Asp Arg Arg Ser Ala Asn Tyr Gln Pro Ser Ile Trp Asp
50                  55                  60

His Asp Phe Leu Gln Ser Leu Asn Ser Lys Tyr Thr Asp Glu Ala Tyr
65                  70                  75                  80

Lys Arg Arg Ala Glu Gly Leu Lys Gly Lys Val Lys Ile Ala Ile Lys
                85                  90                  95

Asp Val Ile Glu Pro Leu Asp Gln Leu Glu Leu Ile Asp Asn Leu Gln
            100                 105                 110

Arg Leu Gly Leu Ala His Arg Phe Glu Thr Glu Ile Arg Asn Ile Leu
        115                 120                 125

Asn Asn Ile Tyr Asn Asn Asn Lys Asp Tyr Asn Trp Arg Lys Glu Asn
130                 135                 140

Leu Tyr Ala Thr Ser Leu Glu Phe Arg Leu Leu Arg Gln His Gly Tyr
145                 150                 155                 160

Pro Val Ser Gln Glu Val Phe Asn Gly Leu Lys Asp Gly Gln Gly Gly
                165                 170                 175

Phe Ile Cys Asp Asp Phe Lys Gly Ile Leu Ser Leu His Glu Ala Ser
            180                 185                 190

Tyr Tyr Ser Leu Glu Gly Glu Ser Ile Met Glu Glu Ala Trp Gln Phe
        195                 200                 205

Thr Ser Lys His Leu Lys Glu Val Met Ile Ser Lys Ser Lys Glu Glu
210                 215                 220

His Val Phe Val Ala Glu Gln Ala Lys Arg Ala Leu Glu Leu Pro Leu
225                 230                 235                 240

His Trp Lys Val Pro Met Leu Glu Ala Arg Trp Phe Ile His Val Tyr
                245                 250                 255

Glu Lys Arg Glu Asp Lys Asn His Leu Leu Leu Glu Leu Ala Lys Leu
            260                 265                 270

Glu Phe Asn Thr Leu Gln Ala Ile Tyr Gln Glu Glu Leu Lys Asp Ile
        275                 280                 285

Ser Gly Trp Trp Lys Glu Thr Gly Leu Gly Glu Lys Leu Ser Phe Ala
290                 295                 300

Arg Asp Ser Leu Val Ala Ser Phe Leu Trp Ser Met Gly Ile Gly Ser
305                 310                 315                 320

Glu Pro Gln Phe Ala Tyr Cys Arg Arg Ile Val Thr Ile Ala Ile Ala
            325                 330                 335

Leu Ile Thr Val Ile Asp Asp Ile Tyr Asp Val Tyr Gly Thr Leu Asp
        340                 345                 350

Glu Leu Glu Leu Phe Thr Ala Ala Val Ala Arg Trp Asp Ile His Tyr
    355                 360                 365

Ala Leu Asn His Leu Pro Asp Tyr Met Lys Leu Cys Phe Phe Ala Leu
370                 375                 380

Tyr Asn Phe Val Asn Glu Phe Ala Tyr Tyr Val Leu Lys Lys Gln Asp
385                 390                 395                 400

Phe Asp Met Leu Arg Ser Ile Lys Asn Ser Trp Leu Gly Leu Leu Gln
                405                 410                 415

Ala Cys Leu Val Glu Ala Lys Trp Tyr His Thr Lys Tyr Thr Pro Thr
            420                 425                 430

Leu Gly Glu Phe Leu Glu Asn Gly Leu Val Ser Ile Gly Gly Pro Met
        435                 440                 445

Gly Ile Met Thr Ala Tyr Leu Ser Gly Thr Asn Pro Ile Ile Glu Lys
    450                 455                 460

Glu Leu Glu Phe Leu Glu Ser Asn Gln Asp Ile Ile His Trp Ser Cys
465                 470                 475                 480

Lys Ile Phe Arg Leu Gln Asp Asp Leu Gly Thr Ser Ser Asp Glu Ile
                485                 490                 495

Gln Arg Gly Asp Val Pro Lys Ser Ile Glu Cys Tyr Met His Glu Thr
            500                 505                 510

Gly Ala Ser Glu Glu Val Ala Arg Glu His Ile Lys Asp Met Met Arg
        515                 520                 525

Gln Met Trp Lys Lys Val Asn Ala Tyr Arg Ala Asp Lys Asp Ser Pro
    530                 535                 540

Leu Ser Gln Asn Thr Val Asp Phe Met Leu Asn Leu Val Arg Met Ser
545                 550                 555                 560

His Phe Met Tyr Leu Arg Gly Asp Gly His Gly Ala Gln Asn Gln Glu
                565                 570                 575

Thr Met Asp Val Ala Ser Thr Trp Leu Phe Gln Pro Ile Pro Leu Glu
            580                 585                 590

Asp Lys His Met Ala Phe Thr Ala Pro Lys Ala Asp Glu Phe Pro Glu
        595                 600                 605

Tyr Ser Phe Ser
    610

<210> SEQ ID NO 24
<211> LENGTH: 571
<212> TYPE: PRT
<213> ORGANISM: Saccharomyces cerevisiae

<400> SEQUENCE: 24

Met Asp Ser Arg Thr Val Gly Ile Leu Gly Gly Gly Gln Leu Gly Arg
1               5                   10                  15

Met Ile Val Glu Ala Ala Asn Arg Leu Asn Ile Lys Thr Val Ile Leu
            20                  25                  30

Asp Ala Glu Asn Ser Pro Ala Lys Gln Ile Ser Asn Ser Asn Asp His
        35                  40                  45

Val Asn Gly Ser Phe Ser Asn Pro Leu Asp Ile Glu Lys Leu Ala Glu
    50                  55                  60

```
Lys Cys Asp Val Leu Thr Ile Glu Ile Glu His Val Asp Val Pro Thr
 65                  70                  75                  80

Leu Lys Asn Leu Gln Val Lys His Pro Lys Leu Lys Ile Tyr Pro Ser
                 85                  90                  95

Pro Glu Thr Ile Arg Leu Ile Gln Asp Lys Tyr Ile Gln Lys Glu His
            100                 105                 110

Leu Ile Lys Asn Gly Ile Ala Val Thr Gln Ser Val Pro Val Glu Gln
        115                 120                 125

Ala Ser Glu Thr Ser Leu Leu Asn Val Gly Arg Asp Leu Gly Phe Pro
130                 135                 140

Phe Val Leu Lys Ser Arg Thr Leu Ala Tyr Asp Gly Arg Gly Asn Phe
145                 150                 155                 160

Val Val Lys Asn Lys Glu Met Ile Pro Glu Ala Leu Glu Val Leu Lys
                165                 170                 175

Asp Arg Pro Leu Tyr Ala Glu Lys Trp Ala Pro Phe Thr Lys Glu Leu
            180                 185                 190

Ala Val Met Ile Val Arg Ser Val Asn Gly Leu Val Phe Ser Tyr Pro
        195                 200                 205

Ile Val Glu Thr Ile His Lys Asp Asn Ile Cys Asp Leu Cys Tyr Ala
210                 215                 220

Pro Ala Arg Val Pro Asp Ser Val Gln Leu Lys Ala Lys Leu Leu Ala
225                 230                 235                 240

Glu Asn Ala Ile Lys Ser Phe Pro Gly Cys Gly Ile Phe Gly Val Glu
                245                 250                 255

Met Phe Tyr Leu Glu Thr Gly Glu Leu Leu Ile Asn Glu Ile Ala Pro
            260                 265                 270

Arg Pro His Asn Ser Gly His Tyr Thr Ile Asp Ala Cys Val Thr Ser
        275                 280                 285

Gln Phe Glu Ala His Leu Arg Ser Ile Leu Asp Leu Pro Met Pro Lys
290                 295                 300

Asn Phe Thr Ser Phe Ser Thr Ile Thr Thr Asn Ala Ile Met Leu Asn
305                 310                 315                 320

Val Leu Gly Asp Lys His Thr Lys Asp Lys Glu Leu Glu Thr Cys Glu
                325                 330                 335

Arg Ala Leu Ala Thr Pro Gly Ser Ser Val Tyr Leu Tyr Gly Lys Glu
            340                 345                 350

Ser Arg Pro Asn Arg Lys Val Gly His Ile Asn Ile Ile Ala Ser Ser
        355                 360                 365

Met Ala Glu Cys Glu Gln Arg Leu Asn Tyr Ile Thr Gly Arg Thr Asp
370                 375                 380

Ile Pro Ile Lys Ile Ser Val Ala Gln Lys Leu Asp Leu Glu Ala Met
385                 390                 395                 400

Val Lys Pro Leu Val Gly Ile Ile Met Gly Ser Asp Ser Asp Leu Pro
                405                 410                 415

Val Met Ser Ala Ala Cys Ala Val Leu Lys Asp Phe Gly Val Pro Phe
            420                 425                 430

Glu Val Thr Ile Val Ser Ala His Arg Thr Pro His Arg Met Ser Ala
        435                 440                 445

Tyr Ala Ile Ser Ala Ser Lys Arg Gly Ile Lys Thr Ile Ile Ala Gly
        450                 455                 460

Ala Gly Gly Ala Ala His Leu Pro Gly Met Val Ala Ala Met Thr Pro
465                 470                 475                 480
```

```
Leu Pro Val Ile Gly Val Pro Val Lys Gly Ser Cys Leu Asp Gly Val
                485             490             495

Asp Ser Leu His Ser Ile Val Gln Met Pro Arg Gly Val Pro Val Ala
            500             505             510

Thr Val Ala Ile Asn Asn Ser Thr Asn Ala Ala Leu Leu Ala Val Arg
            515             520             525

Leu Leu Gly Ala Tyr Asp Ser Ser Tyr Thr Thr Lys Met Glu Gln Phe
            530             535             540

Leu Leu Lys Gln Glu Glu Val Leu Val Lys Ala Gln Lys Leu Glu
545             550             555             560

Thr Val Gly Tyr Glu Ala Tyr Leu Glu Asn Lys
            565             570

<210> SEQ ID NO 25
<211> LENGTH: 1367
<212> TYPE: PRT
<213> ORGANISM: Streptococcus pyogenes

<400> SEQUENCE: 25

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Leu
            20                  25                  30

Lys Val Leu Gly Asn Thr Asp Arg His Gly Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Val Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
            290                 295                 300
Ile Leu Arg Val Asn Ser Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Ala Lys Leu Asn Arg Glu Asp Leu Leu Arg
385                 390                 395                 400
Lys Gln Arg Thr Phe Asp Asn Gly Ser Ile Pro Tyr Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Thr Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
610                 615                 620
Leu Phe Glu Asp Lys Glu Met Ile Glu Glu Arg Leu Lys Lys Tyr Ala
625                 630                 635                 640
Asn Leu Phe Asp Asp Lys Val Met Lys Gln Leu Lys Arg Arg His Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile Asn Asp Asp Ser Leu Thr Phe
        690                 695                 700
```

-continued

Lys Glu Ala Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
            725                 730                 735

Ile Leu Gln Thr Val Lys Ile Val Asp Glu Leu Val Lys Val Met Gly
        740                 745                 750

His Lys Pro Glu Asn Ile Val Ile Glu Met Ala Arg Glu Asn Gln Thr
    755                 760                 765

Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
        820                 825                 830

Ser Asp Tyr Asp Val Asp His Ile Val Pro Gln Ser Phe Leu Lys Asp
    835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
        900                 905                 910

Ala Gly Phe Ile Lys Arg Gln Leu Val Glu Thr Arg Gln Ile Thr Lys
    915                 920                 925

His Val Ala Gln Ile Leu Asp Ser Arg Met Asn Thr Lys Tyr Asp Glu
930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
        980                 985                 990

Gly Thr Ala Leu Ile Lys Lys Tyr Pro Lys Leu Glu Ser Glu Phe Val
    995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys

```
                     1115                1120                1125

Lys Tyr Gly Gly Phe Asp Ser Pro Thr Val Ala Tyr Ser Val Leu
        1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Arg Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Lys Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Glu Arg Asn Arg Tyr Lys Ser Ile
    1325                1330                1335

Lys Glu Val Leu Asp Ala Thr Leu Ile His Gln Ser Ile Thr Gly
    1340                1345                1350

Leu Tyr Glu Ile Arg Ile Asp Leu Ser Gln Leu Gly Gly Asp
    1355                1360                1365

<210> SEQ ID NO 26
<211> LENGTH: 1053
<212> TYPE: PRT
<213> ORGANISM: Staphylococcus aureus

<400> SEQUENCE: 26

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110
```

-continued

```
Ala Lys Arg Arg Gly Val His Asn Val Asn Glu Val Glu Glu Asp Thr
            115                 120                 125
Gly Asn Glu Leu Ser Thr Lys Glu Gln Ile Ser Arg Asn Ser Lys Ala
        130                 135                 140
Leu Glu Glu Lys Tyr Val Ala Glu Leu Gln Leu Glu Arg Leu Lys Lys
145                 150                 155                 160
Asp Gly Glu Val Arg Gly Ser Ile Asn Arg Phe Lys Thr Ser Asp Tyr
                165                 170                 175
Val Lys Glu Ala Lys Gln Leu Leu Lys Val Gln Lys Ala Tyr His Gln
            180                 185                 190
Leu Asp Gln Ser Phe Ile Asp Thr Tyr Ile Asp Leu Leu Glu Thr Arg
        195                 200                 205
Arg Thr Tyr Tyr Glu Gly Pro Gly Glu Gly Ser Pro Phe Gly Trp Lys
    210                 215                 220
Asp Ile Lys Glu Trp Tyr Glu Met Leu Met Gly His Cys Thr Tyr Phe
225                 230                 235                 240
Pro Glu Glu Leu Arg Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
            260                 265                 270
Glu Lys Leu Glu Tyr Tyr Glu Lys Phe Gln Ile Ile Glu Asn Val Phe
        275                 280                 285
Lys Gln Lys Lys Lys Pro Thr Leu Lys Gln Ile Ala Lys Glu Ile Leu
290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
        355                 360                 365
Thr Asn Leu Asn Ser Glu Leu Thr Gln Glu Glu Ile Glu Gln Ile Ser
    370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
        435                 440                 445
Val Val Lys Arg Ser Phe Ile Gln Ser Ile Lys Val Ile Asn Ala Ile
    450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
            500                 505                 510
Gly Lys Glu Asn Ala Lys Tyr Leu Ile Glu Lys Ile Lys Leu His Asp
        515                 520                 525
Met Gln Glu Gly Lys Cys Leu Tyr Ser Leu Glu Ala Ile Pro Leu Glu
```

```
            530                 535                 540
Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                    565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
        610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                    645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
        690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                    725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
        770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                    805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
        850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                    885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
        930                 935                 940

Lys Cys Tyr Glu Glu Ala Lys Lys Leu Lys Lys Ile Ser Asn Gln Ala
945                 950                 955                 960
```

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 27
<211> LENGTH: 1123
<212> TYPE: PRT
<213> ORGANISM: Francisella tularensis

<400> SEQUENCE: 27

Met Asn Val Lys Ile Leu Pro Ile Ala Ile Asp Leu Asp Val Lys Asn
1               5                   10                  15

Thr Gly Val Phe Ser Ala Phe Tyr Gln Lys Gly Thr Ser Leu Glu Lys
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Lys Arg Arg Gly
    50                  55                  60

Ile Asp Arg Lys Gln Leu Val Lys Arg Leu Phe Lys Leu Val Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Thr Glu Tyr Leu Asn Ile Val Pro Glu Gln Val Lys Ala Ile Leu Met
        115                 120                 125

Asp Ile Phe Asp Asp Tyr Asn Gly Glu Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Arg Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205

Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Glu Ile Leu Gly Thr Leu Leu Thr
                245                 250                 255

Asp Asp Phe Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Thr Gln

```
                275                 280                 285
Ala His Leu His His Phe Val Phe Val Val Asn Lys Ile Lys Ser Glu
290                 295                 300
Met Ala Ser Gly Gly Arg His Arg Ser Gln Tyr Phe Gln Glu Ile Thr
305                 310                 315                 320
Asn Val Leu Asp Glu Asn Asn His Gln Glu Gly Tyr Leu Lys Asn Phe
                325                 330                 335
Cys Glu Asn Leu His Asn Lys Lys Tyr Ser Asn Leu Ser Val Lys Asn
                340                 345                 350
Leu Val Asn Leu Val Gly Asn Leu Ser Asn Leu Glu Leu Lys Pro Leu
                355                 360                 365
Arg Lys Tyr Phe Asn Asp Lys Ile His Ala Lys Ala Asp His Trp Asp
370                 375                 380
Glu Gln Lys Phe Thr Glu Thr Tyr Cys His Trp Ile Leu Gly Glu Trp
385                 390                 395                 400
Arg Val Gly Val Lys Asp Gln Asp Lys Lys Asp Gly Ala Lys Tyr Ser
                405                 410                 415
Tyr Lys Asp Leu Cys Asn Glu Leu Lys Gln Lys Val Thr Lys Ala Gly
                420                 425                 430
Leu Ile Asp Phe Leu Leu Glu Leu Asp Pro Cys Arg Thr Ile Pro Pro
                435                 440                 445
Tyr Leu Asp Asn Asn Arg Lys Pro Pro Lys Cys Gln Ser Leu Ile
450                 455                 460
Leu Asn Pro Lys Phe Leu Asp Asn Gln Tyr Pro Asn Trp Gln Gln Tyr
465                 470                 475                 480
Leu Gln Glu Leu Lys Lys Leu Gln Ser Ile Gln Asp Tyr Leu Asp Ser
                485                 490                 495
Phe Glu Thr Asp Leu Lys Asp Leu Lys Ser Ser Lys Asp Gln Pro Tyr
                500                 505                 510
Phe Val Glu Tyr Lys Ser Ser Asn Gln Gln Met Ala Ser Gly Gln Arg
                515                 520                 525
Asp Tyr Lys Asp Leu Asp Ala Arg Ile Leu Gln Phe Ile Phe Asp Arg
530                 535                 540
Val Lys Ala Ser Asp Glu Leu Leu Leu Asn Glu Ile Tyr Phe Gln Ala
545                 550                 555                 560
Lys Lys Leu Lys Gln Lys Ala Ser Ser Glu Leu Glu Lys Leu Glu Ser
                565                 570                 575
Ser Lys Lys Leu Asp Glu Val Ile Ala Asn Ser Gln Leu Ser Gln Ile
                580                 585                 590
Leu Lys Ser Gln His Thr Asn Gly Ile Phe Glu Gln Gly Thr Phe Leu
                595                 600                 605
His Leu Val Cys Lys Tyr Tyr Lys Gln Arg Gln Arg Ala Arg Asp Ser
610                 615                 620
Arg Leu Tyr Ile Met Pro Glu Tyr Arg Tyr Asp Lys Lys Leu Asp Lys
625                 630                 635                 640
Tyr Asn Asn Thr Gly Arg Phe Asp Asp Asn Asn Gln Leu Leu Thr Tyr
                645                 650                 655
Cys Asn His Lys Pro Arg Gln Lys Arg Tyr Gln Leu Leu Asn Asp Leu
                660                 665                 670
Ala Gly Val Leu Gln Val Ser Arg Asn Gln Leu Leu Ser Ser Val Glu
                675                 680                 685
Glu Trp Phe Gln Gln Ala Gln Arg Val Gly Glu Ile Ser Lys Ser Gln
                690                 695                 700
```

```
Asp Glu Gln Ile Phe Glu Trp Leu Lys Ser Phe Lys Ile Ala Ser Tyr
705                 710                 715                 720

Cys Lys Ala Ala Val Glu Met Gln Lys Gln Tyr Arg Gly Thr Leu Lys
            725                 730                 735

Asn Ala Ile Gln Thr Ala Ile Phe Arg Gln Ser Glu Asn Ile Asn Lys
        740                 745                 750

Asn Lys Asn Thr Gly Asn Gln Gln Ala Leu Ser Glu Asn Ser Lys
    755                 760                 765

Asp Val Lys Ser Leu Thr Ala Asp Glu Lys Lys Leu Leu Lys Leu Ile
770                 775                 780

Glu Asn Ile Ala Lys Ala Ser Gln Lys Ile Gly Glu Ser Leu Gly Leu
785                 790                 795                 800

Asn Asp Lys Gln Ile Lys Lys Phe Asn Ser Ile Tyr Ser Phe Ala Gln
            805                 810                 815

Ile Gln Gln Ile Ala Phe Ala Lys Arg Lys Gly Asn Ala Asn Thr Cys
            820                 825                 830

Ala Val Cys Ser Ala Asp Asn Ala His Arg Met Gln Ile Lys Ile
        835                 840                 845

Thr Glu Leu Val Glu Asp Asn Lys Asp Asn Ile Ile Leu Ser Ala Lys
    850                 855                 860

Ala Gln Arg Leu Pro Ala Ile Pro Thr Arg Ile Val Asp Gly Ala Val
865                 870                 875                 880

Lys Lys Met Ala Thr Ile Leu Ala Lys Asn Ile Val Asp Asp Asn Trp
            885                 890                 895

Gln Asn Ile Lys Gln Val Leu Ser Ala Lys His Gln Leu His Ile Pro
            900                 905                 910

Ile Ile Thr Glu Ser Asn Ala Phe Glu Phe Glu Pro Ala Leu Ala Asp
        915                 920                 925

Val Lys Gly Lys Ser Leu Lys Asp Arg Arg Lys Lys Ala Leu Glu Arg
    930                 935                 940

Ile Ser Pro Glu Asn Ile Phe Lys Asp Lys Asn Asn Arg Ile Lys Glu
945                 950                 955                 960

Phe Ala Lys Gly Ile Ser Ala Tyr Ser Gly Ala Asn Leu Thr Asp Gly
            965                 970                 975

Asp Phe Asp Gly Ala Lys Glu Glu Leu Asp His Ile Ile Pro Arg Ser
        980                 985                 990

His Lys Lys Tyr Gly Thr Leu Asn Asp Glu Ala Asn Leu Ile Cys Val
    995                 1000                1005

Thr Arg Asp Asp Asn Lys Asn  Ile Phe Ala Ile Asp  Thr Ser Lys
    1010            1015                1020

Trp Phe Glu Ile Glu Thr Pro  Ser Asp Leu Arg Asp  Ile Gly Val
    1025            1030                1035

Ala Thr Ile Gln Tyr Lys Ile  Asp Asn Asn Ser Arg  Pro Lys Val
    1040            1045                1050

Arg Val Lys Leu Asp Tyr Val  Ile Asp Asp Ser  Lys Ile Asn
    1055            1060                1065

Tyr Phe Met Asn His Ser Leu  Leu Lys Ser Arg Tyr  Pro Asp Lys
    1070            1075                1080

Val Leu Glu Ile Leu Lys Gln  Ser Thr Ile Ile Glu  Phe Glu Ser
    1085            1090                1095

Ser Gly Phe Asn Lys Thr Ile  Lys Glu Met Leu Gly  Met Thr Leu
    1100            1105                1110
```

-continued

Ala Gly Ile Tyr Asn Glu Thr Ser Asn Asn
    1115                1120

<210> SEQ ID NO 28
<211> LENGTH: 583
<212> TYPE: PRT
<213> ORGANISM: Olea europaea

<400> SEQUENCE: 28

Met Asp Cys Thr Met Thr Ser Ile Ser Leu Phe Ser Gln Ser Ser Asn
1               5                   10                  15

Gly Ile Ser Gly Thr Ala Arg Ser Pro Phe Gln Trp Pro Ile Asn His
            20                  25                  30

Arg Phe Ser Ser Gly Gln Arg Asp Phe Ile Cys Lys Ser Leu Pro Val
        35                  40                  45

Ser Ser Pro Ser Ala Thr Pro Leu Ile Pro Ala Glu Asn Gly Ala Met
    50                  55                  60

Tyr Asn Tyr Ile Arg Gln Pro Val Ile Val Thr Pro Glu Val Asp Asp
65                  70                  75                  80

Gly Thr Lys His Ser Glu Leu Val Glu Arg Thr Arg Arg Glu Leu Gln
                85                  90                  95

Arg Ser Thr Lys Pro Val Glu Thr Leu Lys Leu Ile Asp Asn Leu Gln
            100                 105                 110

Arg Leu Gly Ile Ala Tyr Tyr Phe Glu Asp Asp Ile Asn Ala Ile Leu
        115                 120                 125

Asp Gln Phe Ser Asp Gly Leu Pro Asp Glu Asp Leu Phe Thr Thr Ala
    130                 135                 140

Leu Cys Phe Arg Leu Leu Arg Asp Gln Arg Leu Gln Thr Gly Ser Asp
145                 150                 155                 160

Val Phe Leu Lys Phe Met Glu Lys Asn Met Lys Phe Lys Glu His Leu
                165                 170                 175

Ala Gln Asp Thr Ile Gly Leu Val Ser Leu Tyr Glu Ala Ser Ser Met
            180                 185                 190

Gly Ala Asn Gly Glu Glu Ile Leu Ser Glu Ala Lys Glu Phe Thr Glu
        195                 200                 205

Met His Leu Arg Gln Ser Met Pro Gln Leu Ala Pro Gln Leu Arg Arg
    210                 215                 220

Gln Val Ser Ser Ala Leu Glu Leu Pro Arg His Leu Arg Met Ala Arg
225                 230                 235                 240

Leu Glu Ala Arg Arg Tyr Ile Glu Glu Tyr Gly Asn Glu Ser Asp His
                245                 250                 255

Asp Pro Ala Leu Leu Glu Leu Ala Arg Leu Asp Tyr Asn Lys Val Gln
            260                 265                 270

Leu Gln His Gln Met Glu Leu Ala Glu Ile Thr Arg Trp Trp Lys Gln
        275                 280                 285

Leu Gly Leu Val Glu Lys Leu Ser Phe Ala Arg Asp Arg Pro Leu Glu
    290                 295                 300

Cys Phe Leu Trp Thr Val Gly Leu Leu Pro Glu Pro Lys Tyr Ser Ser
305                 310                 315                 320

Cys Arg Ile Glu Leu Ala Lys Thr Ile Ala Ile Leu Leu Val Ile Asp
                325                 330                 335

Asp Ile Phe Asp Thr Tyr Gly Lys Met Glu Glu Leu Val Leu Phe Thr
            340                 345                 350

Glu Ala Ile Gln Arg Trp Asp Leu Asp Glu Leu Glu Thr Leu Pro Pro
        355                 360                 365

```
Tyr Met Arg Ile Cys Tyr Met Ala Leu Tyr Asn Thr Thr Asn Glu Ile
        370                 375                 380

Cys Tyr Lys Ile Leu Lys Glu Tyr Gly Phe Cys Val Leu Pro Tyr Leu
385                 390                 395                 400

Lys Ser Thr Trp Ile Asp Met Ile Glu Gly Phe Met Val Glu Ala Asn
                405                 410                 415

Trp Phe Asn Gly Gly His Gly Pro Asn Leu Glu Glu Tyr Ile Glu Asn
            420                 425                 430

Gly Val Ser Thr Ala Gly Ala Tyr Met Ala Leu Val His Leu Phe Phe
            435                 440                 445

Leu Ile Gly Glu Gly Val Thr Asn Glu Asn Ile Ala Lys Leu Leu Arg
450                 455                 460

Lys Pro Tyr Pro Lys Leu Phe Ser Ala Ala Gly Arg Ile Leu Arg Leu
465                 470                 475                 480

Trp Asp Asp Leu Gly Thr Ala Lys Glu Glu Glu Arg Gly Asp Leu
                485                 490                 495

Ala Ser Cys Met Gln Ile Leu Met Arg Glu Lys Asn Ile Asp Cys Glu
                500                 505                 510

Asn Glu Gly Arg Asn Tyr Ile Leu Lys Ala Ile Asn Gly Leu Trp Lys
            515                 520                 525

Asp Leu Asn Asp Glu Leu Ile Ser Pro Asn Ala Met Pro Leu Ala Ile
530                 535                 540

Thr Lys Val Ala Leu Asn Met Ala Arg Ala Phe Glu Val Val Tyr Lys
545                 550                 555                 560

His Glu Glu Asp Ser Tyr Phe Ser Val Asp Asn Tyr Val Gln Ala
                565                 570                 575

Leu Phe Phe Thr Pro Ile Asn
            580

<210> SEQ ID NO 29
<211> LENGTH: 584
<212> TYPE: PRT
<213> ORGANISM: Phyla dulcis

<400> SEQUENCE: 29

Met Ala Ser Ala Arg Ser Thr Ile Ser Leu Ser Ser Gln Ser Ser His
1               5                   10                  15

His Gly Phe Ser Lys Asn Ser Phe Pro Trp Gln Leu Arg His Ser Arg
            20                  25                  30

Phe Val Met Gly Ser Arg Ala Arg Thr Cys Ala Cys Met Ser Ser Ser
        35                  40                  45

Val Ser Leu Pro Thr Ala Thr Thr Ser Ser Val Ile Thr Gly Asn
50                  55                  60

Asp Ala Leu Leu Lys Tyr Ile Arg Gln Pro Met Val Ile Pro Leu Lys
65                  70                  75                  80

Glu Lys Glu Gly Thr Lys Arg Arg Glu Tyr Leu Leu Glu Lys Thr Ala
                85                  90                  95

Arg Glu Leu Gln Gly Thr Thr Glu Ala Ala Glu Lys Leu Lys Phe Ile
            100                 105                 110

Asp Thr Ile Gln Arg Leu Gly Ile Ser Cys Tyr Phe Glu Asp Glu Ile
        115                 120                 125

Asn Gly Ile Leu Gln Ala Glu Leu Ser Asp Thr Asp Gln Leu Glu Asp
    130                 135                 140

Gly Leu Phe Thr Thr Ala Leu Arg Phe Arg Leu Leu Arg His Tyr Gly
```

```
            145                 150                 155                 160
Tyr Gln Ile Ala Pro Asp Val Phe Leu Lys Phe Thr Asp Gln Asn Gly
                165                 170                 175

Lys Phe Lys Glu Ser Leu Ala Asp Asp Thr Gln Gly Leu Val Ser Leu
            180                 185                 190

Tyr Glu Ala Ser Tyr Met Gly Ala Asn Gly Glu Asn Ile Leu Glu Glu
            195                 200                 205

Ala Met Lys Phe Thr Lys Thr His Leu Gln Gly Arg Gln His Ala Met
        210                 215                 220

Arg Glu Val Ala Glu Ala Leu Glu Leu Pro Arg His Leu Arg Met Ala
225                 230                 235                 240

Arg Leu Glu Ala Arg Arg Tyr Ile Glu Gln Tyr Gly Thr Met Ile Gly
                245                 250                 255

His Asp Lys Asp Leu Leu Glu Leu Val Ile Leu Asp Tyr Asn Asn Val
            260                 265                 270

Gln Ala Gln His Gln Ala Glu Leu Ala Glu Ile Ala Arg Trp Trp Lys
        275                 280                 285

Glu Leu Gly Leu Val Asp Lys Leu Thr Phe Ala Arg Asp Arg Pro Leu
    290                 295                 300

Glu Cys Phe Leu Trp Thr Val Gly Leu Leu Pro Glu Pro Lys Tyr Ser
305                 310                 315                 320

Ala Cys Arg Ile Glu Leu Ala Lys Thr Ile Ala Ile Leu Leu Val Ile
                325                 330                 335

Asp Asp Ile Phe Asp Thr Tyr Gly Lys Met Glu Glu Leu Ala Leu Phe
            340                 345                 350

Thr Glu Ala Ile Arg Arg Trp Asp Leu Glu Ala Met Glu Thr Leu Pro
        355                 360                 365

Glu Tyr Met Lys Ile Cys Tyr Met Ala Leu Tyr Asn Thr Thr Asn Glu
    370                 375                 380

Ile Cys Tyr Lys Val Leu Lys Lys Asn Gly Trp Ser Val Leu Pro Tyr
385                 390                 395                 400

Leu Arg Tyr Thr Trp Met Asp Met Ile Glu Gly Phe Met Val Glu Ala
                405                 410                 415

Lys Trp Phe Asn Gly Gly Ser Ala Pro Asn Leu Glu Glu Tyr Ile Glu
            420                 425                 430

Asn Gly Val Ser Thr Ala Gly Ala Tyr Met Ala Leu Val His Leu Phe
        435                 440                 445

Phe Leu Ile Gly Glu Gly Val Ser Ala Gln Asn Ala Gln Ile Leu Leu
    450                 455                 460

Lys Lys Pro Tyr Pro Lys Leu Phe Ser Ala Ala Gly Arg Ile Leu Arg
465                 470                 475                 480

Leu Trp Asp Asp Leu Gly Thr Ala Lys Glu Glu Gly Arg Gly Asp
                485                 490                 495

Leu Ala Ser Ser Ile Arg Leu Phe Met Lys Glu Lys Asn Leu Thr Thr
            500                 505                 510

Glu Glu Glu Gly Arg Asn Gly Ile Gln Glu Glu Ile Tyr Ser Leu Trp
        515                 520                 525

Lys Asp Leu Asn Gly Glu Leu Ile Ser Lys Gly Arg Met Pro Leu Ala
    530                 535                 540

Ile Ile Lys Val Ala Leu Asn Met Ala Arg Ala Ser Gln Val Val Tyr
545                 550                 555                 560

Lys His Asp Glu Asp Ser Tyr Phe Ser Cys Val Asp Asn Tyr Val Glu
                565                 570                 575
```

```
Ala Leu Phe Phe Thr Pro Leu Leu
            580

<210> SEQ ID NO 30
<211> LENGTH: 595
<212> TYPE: PRT
<213> ORGANISM: Vitis vinifera

<400> SEQUENCE: 30

Met Ala Phe Asn Met Ser Arg Phe Val Thr Met Pro Ser His Val Leu
1               5                   10                  15

Pro Ser Ser Phe Val Ala Pro Ser Leu Gln Val Ser Ser Ser Pro Cys
            20                  25                  30

Ser Trp Arg Thr Arg Pro Ser Pro Cys Thr Ser Cys His Leu Ser Pro
            35                  40                  45

Ser Ser Ser Ser Lys Pro Leu Leu Gly Ser His Asp Tyr Ser Leu Leu
    50                  55                  60

Lys Ser Leu Thr Leu Ser Pro His Ala Val Asn Ser Glu Ala Asp Ser
65                  70                  75                  80

Ser Thr Arg Arg Met Lys Glu Val Lys Glu Arg Thr Trp Glu Ala Phe
                85                  90                  95

Tyr Arg Ala Trp Asp Ser Arg Ala Ala Met Glu Met Val Asp Thr Val
            100                 105                 110

Glu Arg Leu Gly Leu Ser Tyr His Phe Glu Asp Glu Ile Asn Ala Leu
            115                 120                 125

Leu Gln Arg Phe Cys Asp Trp Asn Ala Ser Glu Asp Leu Phe Thr Thr
    130                 135                 140

Ala Leu Arg Phe Arg Leu Leu Arg Gln Asn Gly Phe Pro Thr His Ser
145                 150                 155                 160

Asp Val Phe Gly Lys Phe Met Asp Lys Asn Gly Lys Phe Lys Glu Ser
                165                 170                 175

Leu Thr Glu Asp Ile Arg Gly Met Leu Ser Leu His Glu Ala Ser His
            180                 185                 190

Leu Gly Ala Lys Asn Glu Glu Val Leu Ala Glu Ala Lys Glu Phe Thr
            195                 200                 205

Arg Ile His Leu Ile Gln Ser Met Pro His Met Glu Pro His Phe Ser
    210                 215                 220

Ser His Val Gly Arg Ala Leu Glu Leu Pro Arg His Leu Arg Met Val
225                 230                 235                 240

Arg Leu Glu Ala Arg Asn Tyr Ile Gly Glu Tyr Ser Arg Glu Ser Asn
                245                 250                 255

Pro Asn Leu Ala Phe Leu Glu Leu Ala Lys Leu Asp Phe Asp Met Val
            260                 265                 270

Gln Ser Leu His Gln Lys Glu Leu Ala Glu Ile Leu Arg Trp Trp Lys
            275                 280                 285

Gln Leu Gly Leu Val Asp Lys Leu Asp Phe Ala Arg Asp Arg Pro Met
    290                 295                 300

Glu Cys Phe Leu Trp Thr Val Gly Ile Phe Pro Asp Pro Arg His Ser
305                 310                 315                 320

Ser Cys Arg Ile Glu Leu Thr Lys Ala Ile Ala Ile Leu Leu Val Ile
                325                 330                 335

Asp Asp Ile Tyr Asp Ser Tyr Gly Ser Leu Asp Glu Leu Ala Leu Phe
            340                 345                 350

Thr Asp Ala Val Lys Arg Trp Asp Leu Gly Ala Met Asp Gln Leu Pro
```

```
                355                 360                 365
Glu Tyr Met Lys Ile Cys Tyr Met Ala Leu Tyr Asn Thr Thr Asn Asp
370                 375                 380

Ile Ala Tyr Arg Ile Leu Lys Glu His Gly Trp Ser Val Ile Glu His
385                 390                 395                 400

Leu Lys Arg Thr Trp Met Asp Ile Phe Gly Ala Phe Leu Ala Glu Ala
            405                 410                 415

Tyr Cys Phe Lys Gly Gly His Val Pro Ser Leu Glu Glu Tyr Leu Thr
                420                 425                 430

Asn Ala Val Thr Thr Gly Gly Thr Tyr Met Ala Leu Val His Ala Phe
            435                 440                 445

Phe Leu Met Gly Gln Gly Val Thr Arg Glu Asn Met Ala Met Leu Lys
        450                 455                 460

Pro Tyr Pro Asn Ile Phe Ser Cys Ser Gly Lys Ile Leu Arg Leu Trp
465                 470                 475                 480

Asp Asp Leu Gly Thr Ala Arg Glu Glu Gln Glu Arg Gly Asp Asn Ala
                485                 490                 495

Ser Ser Ile Glu Cys Tyr Lys Arg Glu Arg Glu Met Asp Thr Val Leu
            500                 505                 510

Glu Asp Glu Ala Cys Arg Lys His Ile Arg Gln Met Ile Gln Ser Leu
        515                 520                 525

Trp Val Glu Leu Asn Gly Glu Leu Val Ala Ser Ser Ala Leu Pro Leu
    530                 535                 540

Ser Ile Ile Lys Ala Ala Phe Asn Leu Ser Arg Thr Ala Gln Val Ile
545                 550                 555                 560

Tyr Gln His Gly Asp Asp Asn Lys Thr Ser Ser Val Glu Asp His Val
                565                 570                 575

Gln Ala Leu Leu Phe Arg Pro Val Ser Ser Asn Gly His Ala Gln Ile
            580                 585                 590

Thr Met His
        595

<210> SEQ ID NO 31
<211> LENGTH: 567
<212> TYPE: PRT
<213> ORGANISM: Ocimum basilicum

<400> SEQUENCE: 31

Met Ser Cys Ala Arg Ile Thr Val Thr Leu Pro Tyr Arg Ser Ala Lys
1               5                   10                  15

Thr Ser Ile Gln Arg Gly Ile Thr His Tyr Pro Ala Leu Ile Arg Pro
            20                  25                  30

Arg Phe Ser Ala Cys Thr Pro Leu Ala Ser Ala Met Pro Leu Ser Ser
        35                  40                  45

Thr Pro Leu Ile Asn Gly Asp Asn Ser Gln Arg Lys Asn Thr Arg Gln
    50                  55                  60

His Met Glu Glu Ser Ser Ser Lys Arg Arg Glu Tyr Leu Leu Glu Glu
65                  70                  75                  80

Thr Thr Arg Lys Leu Gln Arg Asn Asp Thr Glu Ser Val Glu Lys Leu
                85                  90                  95

Lys Leu Ile Asp Asn Ile Gln Gln Leu Gly Ile Gly Tyr Tyr Phe Glu
            100                 105                 110

Asp Ala Ile Asn Ala Val Leu Arg Ser Pro Phe Ser Thr Gly Glu Glu
        115                 120                 125
```

```
Asp Leu Phe Thr Ala Ala Leu Arg Phe Arg Leu Leu Arg His Asn Gly
    130                 135                 140

Ile Glu Ile Ser Pro Glu Ile Phe Leu Lys Phe Lys Asp Glu Arg Gly
145                 150                 155                 160

Lys Phe Asp Glu Ser Asp Thr Leu Gly Leu Leu Ser Leu Tyr Glu Ala
                165                 170                 175

Ser Asn Leu Gly Val Ala Gly Glu Glu Ile Leu Glu Glu Ala Met Glu
                180                 185                 190

Phe Ala Glu Ala Arg Leu Arg Arg Ser Leu Ser Glu Pro Ala Ala Pro
                195                 200                 205

Leu His Gly Glu Val Ala Gln Ala Leu Asp Val Pro Arg His Leu Arg
    210                 215                 220

Met Ala Arg Leu Glu Ala Arg Arg Phe Ile Glu Gln Tyr Gly Lys Gln
225                 230                 235                 240

Ser Asp His Asp Gly Asp Leu Leu Glu Leu Ala Ile Leu Asp Tyr Asn
                245                 250                 255

Gln Val Gln Ala Gln His Gln Ser Glu Leu Thr Glu Ile Ile Arg Trp
                260                 265                 270

Trp Lys Glu Leu Gly Leu Val Asp Lys Leu Ser Phe Gly Arg Asp Arg
    275                 280                 285

Pro Leu Glu Cys Phe Leu Trp Thr Val Gly Leu Leu Pro Glu Pro Lys
    290                 295                 300

Tyr Ser Ser Val Arg Ile Glu Leu Ala Lys Ala Ile Ser Ile Leu Leu
305                 310                 315                 320

Val Ile Asp Asp Ile Phe Asp Thr Tyr Gly Glu Met Asp Asp Leu Ile
                325                 330                 335

Leu Phe Thr Asp Ala Ile Arg Arg Trp Asp Leu Glu Ala Met Glu Gly
                340                 345                 350

Leu Pro Glu Tyr Met Lys Ile Cys Tyr Met Ala Leu Tyr Asn Thr Thr
                355                 360                 365

Asn Glu Val Cys Tyr Lys Val Leu Arg Asp Thr Gly Arg Ile Val Leu
    370                 375                 380

Leu Asn Leu Lys Ser Thr Trp Ile Asp Met Ile Glu Gly Phe Met Glu
385                 390                 395                 400

Glu Ala Lys Trp Phe Asn Gly Gly Ser Ala Pro Lys Leu Glu Glu Tyr
                405                 410                 415

Ile Glu Asn Gly Val Ser Thr Ala Gly Ala Tyr Met Ala Phe Ala His
                420                 425                 430

Ile Phe Phe Leu Ile Gly Glu Gly Val Thr His Gln Asn Ser Gln Leu
                435                 440                 445

Phe Thr Gln Lys Pro Tyr Pro Lys Val Phe Ser Ala Ala Gly Arg Ile
    450                 455                 460

Leu Arg Leu Trp Asp Asp Leu Gly Thr Ala Lys Glu Glu Gln Glu Arg
465                 470                 475                 480

Gly Asp Leu Ala Ser Cys Val Gln Leu Phe Met Lys Glu Lys Ser Leu
                485                 490                 495

Thr Glu Glu Glu Ala Arg Ser Arg Ile Leu Glu Glu Ile Lys Gly Leu
                500                 505                 510

Trp Arg Asp Leu Asn Gly Glu Leu Val Tyr Asn Lys Asn Leu Pro Leu
                515                 520                 525

Ser Ile Ile Lys Val Ala Leu Asn Met Ala Arg Ala Ser Gln Val Val
    530                 535                 540

Tyr Lys His Asp Gln Asp Thr Tyr Phe Ser Ser Val Asp Asn Tyr Val
```

Asp Ala Leu Phe Phe Thr Gln
545             550             555             565

<210> SEQ ID NO 32
<211> LENGTH: 400
<212> TYPE: PRT
<213> ORGANISM: Saccharomyces cerevisiae

<400> SEQUENCE: 32

Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Gln His Pro Gly Asn Ile
        35                  40                  45

Pro Asn Arg Asp Trp Ala Val Glu Tyr Tyr Ala Gln Arg Ala Gln Arg
    50                  55                  60

Pro Gly Thr Leu Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Lys Lys Ser Phe Ala
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Asn Gly Gly Ser Asn Glu Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

```
Ser Asn Pro Asp Leu Val Asp Arg Leu Glu Lys Gly Leu Pro Leu Asn
        355                 360                 365

Lys Tyr Asp Arg Asp Thr Phe Tyr Lys Met Ser Ala Glu Gly Tyr Ile
    370                 375                 380

Asp Tyr Pro Thr Tyr Glu Glu Ala Leu Lys Leu Gly Trp Asp Lys Asn
385                 390                 395                 400

<210> SEQ ID NO 33
<211> LENGTH: 680
<212> TYPE: DNA
<213> ORGANISM: Saccharomyces cerevisiae

<400> SEQUENCE: 33
cagttcgagt ttatcattat caatactgcc atttcaaaga atacgtaaat aattaatagt    60
agtgattttc ctaactttat ttagtcaaaa aattagcctt ttaattctgc tgtaacccgt   120
acatgcccaa ataggggggc gggttacaca gaatatataa catcgtaggt gtctgggtga   180
acagtttatt cctggcatcc actaaatata atggagcccg cttttaagc tggcatccag    240 aaaaaaaaag aatcccagca ccaaaatatt gttttcttca ccaaccatca gttcataggt   300
ccattctctt agcgcaacta cagagaacag gggcacaaac aggcaaaaaa cgggcacaac   360
ctcaatggag tgatgcaacc tgcctggagt aaatgatgac acaaggcaat tgacccacgc   420
atgtatctat ctcattttct tacaccttct attaccttct gctctctctg atttggaaaa   480
agctgaaaaa aaaggttgaa accagttccc tgaaattatt cccctacttg actaataagt   540
atataaagac ggtaggtatt gattgtaatt ctgtaaatct atttcttaaa cttcttaaat   600
tctactttta tagttagtct ttttttttagt tttaaaacac caagaactta gtttcgaata   660
aacacacata aacaaacaaa                                              680

<210> SEQ ID NO 34
<211> LENGTH: 700
<212> TYPE: DNA
<213> ORGANISM: Saccharomyces cerevisiae

<400> SEQUENCE: 34
taagggcatg atagaattgg attatgtaaa aggtgaagat accattgtag aagcaaccag    60
cacgtcgccg tggctgatga agtctcctct tgcccgggcc gcagaaaaga ggggcagtgg   120 cctgttttc gacataaatg aggggcatgg ccagcaccaa gacgtcattg ttgcatatgg    180
cgtatccaag ccgaaacggc gctcgcctca tccccacggg aataaggcag ccgacaaaag   240
aaaaacgacc gaaaaggaac cagaaagaaa aagaggggtg ggcgcgccgc ggacgtgtaa   300
aaagatatgc atccagcttc tatatcgctt taactttacc gttttgggca tcgggaacgt   360
atgtaacatt gatctcctct tgggaacggt gagtgcaacg aatgcgatat agcaccgacc   420
atgtgggcaa attcgtaata aattcggggt gaggggatt caagacaagc aaccttgtta   480
gtcagctcaa acagcgattt aacggttgag taacacatca aaacaccgtt cgaggtcaag   540
cctggcgtgt ttaacaagtt cttgatatca tatataaatg taataagaag tttggtaata   600
ttcaattcga agtgttcagt cttttacttc tcttgtttta tagaagaaaa aacatcaaga   660
aacatcttta acatacacaa acacatacta tcagaataca                        700

<210> SEQ ID NO 35
<211> LENGTH: 700
<212> TYPE: DNA
<213> ORGANISM: Saccharomyces cerevisiae
```

<400> SEQUENCE: 35

```
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaaaaaac ccagacacgc   240
tcgacttcct gtcatcctat tgattgcagc ttccaatttc gtcacacaac aaggtcctag   300
cgacggctca caggttttgt aacaagcaat cgaaggttct ggaatggcgg gaaagggttt   360
agtaccacat gctatgatgc ccactgtgat ctccagagca aagttcgttc gatcgtactg   420
ttactctctc tctttcaaac agaattgtcc gaatcgtgtg acaacaacag cctgttctca   480
cacactcttt tcttctaacc aagggggtgg tttagtttag tagaacctcg tgaaacttac   540
atttacatat atataaactt gcataaattg gtcaatgcaa gaaatacata tttggtcttt   600
tctaattcgt agttttttcaa gttcttagat gctttctttt tctcttttttt acagatcatc   660
aaggaagtaa ttatctactt tttacaacaa atataaaaca                          700
```

<210> SEQ ID NO 36
<211> LENGTH: 700
<212> TYPE: DNA
<213> ORGANISM: Saccharomyces cerevisiae

<400> SEQUENCE: 36

```
ccttgccaac agggagttct tcagagacat ggaggctcaa aacgaaatta ttgacagcct    60
agacatcaat agtcatacaa cagaaagcga ccacccaact ttggctgata atagcgtata   120
aacaatgcat actttgtacg ttcaaaatac aatgcagtag atatatttat gcatattaca   180
tataatacat atcacatagg aagcaacagg cgcgttggac ttttaatttt cgaggaccgc   240
gaatccttac atcacaccca atcccccaca agtgatcccc cacacaccat agcttcaaaa   300
tgtttctact ccttttttac tcttccagat tttctcggac tccgcgcatc gccgtaccac   360
tcaaaacac ccaagcacag catactaaat ttcccctctt tcttcctcta gggtgtcgtt    420
aattacccgt actaaaggtt tggaaaagaa aaaagacacc gcctcgtttc tttttcttcg   480
tcgaaaaagg caataaaaat ttttatcacg tttcttttc ttgaaaattt ttttttttga    540
ttttttctc tttcgatgac ctcccattga tatttaagtt aataaacggt catcaatttc    600
tcaagtttca gtttcatttt tcttgttcta ttacaacttt ttttacttct tgctcattag   660
aaagaaagca tagcaatcta atctaagttt taattacaaa                          700
```

<210> SEQ ID NO 37
<211> LENGTH: 700
<212> TYPE: DNA
<213> ORGANISM: Saccharomyces cerevisiae

<400> SEQUENCE: 37

```
ttgataggtc aagatcaatg taaacaatta ctttgttatg tagagttttt ttagctacct    60
atattccacc ataacatcaa tcatgcggtt gctggtgtat ttaccaataa tgtttaatgt   120
atatatatat atatatatat ggggccgtat acttacatat agtagatgtc aagcgtaggc   180
gcttcccctg ccggctgtga gggcgccata accaaggtat ctatagaccg ccaatcagca   240
aactacctcc gtacattcat gttgcaccca cacatttata cacccagacc gcgacaaatt   300
acccataagg ttgtttgtga cggcgtcgta caagagaacg tgggaacttt ttaggctcac   360
caaaaaagaa agaaaaaata cgagttgctg acagaagcct caagaaaaaa aaaattcttc   420
```

```
ttcgactatg ctggaggcag agatgatcga gccggtagtt aactatatat agctaaattg      480
gttccatcac cttcttttct ggtgtcgctc cttctagtgc tatttctggc ttttcctatt      540
tttttttttc catttttctt tctctctttc taatatataa attctcttgc attttctatt      600
tttctctcta tctattctac ttgtttattc ccttcaaggt tttttttttaa ggagtacttg     660 tttttagaat atacggtcaa cgaactataa ttaactaaac                            700
```

<210> SEQ ID NO 38
<211> LENGTH: 700
<212> TYPE: DNA
<213> ORGANISM: Saccharomyces cerevisiae

<400> SEQUENCE: 38

```
cacccatgaa ccacacggtt agtccaaaag gggcagttca gattccagat gcgggaatta      60
gcttgctgcc accctcacct cactaacgct gcggtgtgcg gatacttcat gctatttata     120
gacgcgcgtg tcggaatcag cacgcgcaag aaccaaatgg gaaaatcgga atgggtccag     180
aactgctttg agtgctggct attggcgtct gatttccgtt ttgggaatcc tttgccgcgc     240 gccctctca aaactccgca caagtcccag aaagcgggaa agaaataaaa cgccaccaaa      300 aaaaaaaaa taaaagccaa tcctcgaagc gtgggtggta ggccctggat tatcccgtac      360
aagtatttct caggagtaaa aaaaccgtttt gttttggaat ttcccatttc gcggccacct     420
acgccgctat ctttgcaaca actatctgcg ataactcagc aaattttgca tattcgtgtt     480
gcagtattgc gataatggga gtcttacttc aacataacg gcagaaagaa atgtgagaaa      540
attttgcatc ctttgcctcc gttcaagtat ataaagtcgg catgcttgat aatctttctt      600
tccatcctac attgttctaa ttattcttat tctcctttat tctttcctaa cataccaaga     660
aattaatctt ctgtcattcg cttaaacact atatcaataa                            700
```

<210> SEQ ID NO 39
<211> LENGTH: 700
<212> TYPE: DNA
<213> ORGANISM: Saccharomyces cerevisiae

<400> SEQUENCE: 39

```
tcttggggcc ttaccaccag tggactttct tgctgtttgc tttgttctgg ccattgtttg      60
cgtttatata tttatgttag atgttttttct tattaactag aaagaaagaa tataaaaggt    120
tgaggaaaga gatgtatccc gaagaataca cagtctttta tatatgtatt tcaacaagga    180
gccgtggagg gtactaaaaa gaaaaatcgc ccgggcattt cgttatcttc cacgctaaaa    240
gtcaaggaga gatattacgg ccaggatcgc aaaggtgcag agcaaggaaa tgtgagaaat    300
tgtgagaacg ataatgtatg ggacaatgcg aaaatgtgag aacgagagca aaaatctttt    360
ttgtatctcc ccgccgaatt tggaaaccgc gttctgaaaa cttcgcatct tcacatagta    420
aaactgttcc gagcgcttct ccccataatg gttagtggta aaaaccgaag ttgtttactt    480
tagcaaatgc ccgcgaatac ggtggtaaat tgccacccccc ccttccccat tcattgggta    540
aagaccaatt tgatggataa attggttgtg gaaaaggtct aattcttttt cctataaata    600
ccgagatatt ttttctatat gatggtttcc gtcgcattat tgtactctat agtactaaag    660
caacaaacaa aaacaagcaa caaatataat atagtaaaat                            700
```

<210> SEQ ID NO 40
<211> LENGTH: 676
<212> TYPE: DNA

<213> ORGANISM: Saccharomyces cerevisiae

<400> SEQUENCE: 40

```
tgtggagtgt tgcttggat tctttagtaa aaggggaaga acagttggaa gggccaaagt    60
ggaagtcaca aaacagtggt cctatataaa agaacaagaa aaagattatt tatatacaac   120
tgcggtcaca agaagcaacg cgagagagca caacacgctg ttatcacgca aactatgttt   180
tgacaccgag ccatagccgt gattgtgcgt cacattgggc gataatgaac gctaaatgac   240
caactcccat ccgtaggagc cccttagggc gtgccaatag tttcacgcgc ttaatgcgaa   300
gtgctcggaa cggacaactg tggtcgtttg gcaccgggaa agtggtacta gaccgagagt   360
ttcgcatttg tatggcagga cgttctggga gcttcgcgtc taaagctttt tcgggcgcga   420
aatgcagacc agaccagaac aaaacaactg acaagaaggc gtttaattta atatgttgtt   480
cactcgcgcc tgggctgttg ttattcggct agatacatac gtgtttgtgc gtatgtagtt   540
atatcatata taagtatatt aggatgaggc ggtgaaagag attttttttt tttcgcttaa   600
tttattcttt tctctatctt ttttcctaca tcttgttcaa aagagtagca aaacaacaa    660
tcaatacaat aaaata                                                   676
```

<210> SEQ ID NO 41
<211> LENGTH: 700
<212> TYPE: DNA
<213> ORGANISM: Saccharomyces cerevisiae

<400> SEQUENCE: 41

```
aaggcaagcc cagaaaaata tcgcaagcac ctttggtctt acagtgccaa ctttggcct    60
gccgacgtta agagtacaaa gctgatggca atgtacgaca agataacaga gtctcaaaag   120
aagtgaaaca attttctttc accacatttt ccattgttcc ttccccccat aactataaac   180
gtatttatgt atatatattt gcgtgtaagt gtgtgtacta tagggcaccg taaagtaata   240
atgcttaatt agttactact atgaccatat aagaggtcat actgtatgaa gccacaaagc   300
agatagatca atcatgttta acgaaaactg ttaatcgaag attatttctt tttttttttc   360
tctttccttt ttacaaagaa aatttttttt gcgcttttg ccatcaccat cgcaagttct    420
gggacaattg ttctctttcg ctccagttcc aaggaaagag gtttctgttt tacttaatag   480
aaagtgtcat cttgtatttt atatctcttc tttcttgtgt aaaattctt agttttgatt    540
ttgtattttt aggacagtga gctacgaagt aacatttta cttaataacc gtttgaagca   600
tagagcaggc cctggtatca ccacctaata tctggctttt tattcaataa aaactcaaaa   660
aaaaaaatcc aaaaaaaact aaaaaaccaa taaaaataaa                         700
```

<210> SEQ ID NO 42
<211> LENGTH: 700
<212> TYPE: DNA
<213> ORGANISM: Saccharomyces cerevisiae

<400> SEQUENCE: 42

```
aagaggatgt ccaatatttt ttttaaggaa taaggatact tcaagactag attccccct    60
gcattcccat cagaaccgta aaccttggcg ctttccttgg gaagtattca agaagtgcct   120
tgtccggttt ctgtggctca caaccagcg cgcccgatat ggctttcttt tcacttatga    180
atgtaccagt acgggacaat tagaacgctc ctgtaacaat ctctttgcaa atgtggggtt   240
acattctaac catgtcacac tgctgacgaa attcaaagta aaaaaaaatg ggaccacgtc   300
ttgagaacga tagattttct ttattttaca ttgaacagtc gttgtctcag cgcgctttat   360
```

```
gttttcattc atacttcata ttataaaata acaaaagaag aatttcatat tcacgcccaa      420
gaaatcaggc tgctttccaa atgcaattga cacttcatta gccatcacac aaaactcttt      480
cttgctggag cttcttttaa aaaagacctc agtacaccaa acacgttacc cgacctcgtt      540
attttacgac aactatgata aaattctgaa gaaaaaataa aaaatttttc atacttcttg      600
cttttattta aaccattgaa tgatttcttt tgaacaaaac tacctgtttc accaaaggaa      660
atagaaagaa aaaatcaatt agaagaaaac aaaaaacaaa                            700
```

<210> SEQ ID NO 43
<211> LENGTH: 700
<212> TYPE: DNA
<213> ORGANISM: Saccharomyces cerevisiae

<400> SEQUENCE: 43

```
ggatatcgta acaaaggcg ttaccataga aatgtactga ttggcagaat tactcttcag       60
gagaatcttt catacaaagg tattccattg gggaaaatct cgttaccaag tcaatgctga     120
actttctatg gcctttgttt actatcgtta attattttac gaccacttct gggtagaaat     180
atttcgtagc cctggaacga gcttgtttac gcgttttatc ccattatatg gcacccaaat     240
caaatttaaa aagaaaaaac gcgtaaacag tgtcgggtaa gttcatcctc tgttacttta     300
attgcttctt tttttgaaat tctaagtaaa cgcgtcattt tgatcctcag gacacagaaa     360
tccttgcaga atcttattgg gtgttgaata gaggacgcgt aaaaacgata tggaaatttt     420
tttcatatag tgtagaaaga ataggttggc gtaggtagtt tcgtgtttga tagaaacctc     480
caacaaagtc tgcaactcac gttttagaat aacaagttta gagtttatct tgttgccttt     540
gttaagtcag taccattgaa taaaaattat ataaaggagc taatatttca ttgttggaaa     600
attactctac cataattgaa gcatatctca tccttttcat ccttttcaac gcaagagaga     660
caccaacgaa caacacttta tttgttgata tattaacatc                           700
```

<210> SEQ ID NO 44
<211> LENGTH: 700
<212> TYPE: DNA
<213> ORGANISM: Saccharomyces cerevisiae

<400> SEQUENCE: 44

```
agtcgaacaa gaagcaggca aagtttagag cactgcccct ccgcactcaa aaaagaaaaa      60
actaggagga aaataaaatt ctcaaccaca caaacacata aacacataca aatacaaata     120
caagcttatt tacttgacat cgcgcgatct tccactattc agcgccgtcc gccctctctc     180
gtgttttttg tttacgcgac aactatgcga aatccggagc aacgggcaac cgtttgggga     240
aagaccacac ccacgcgcga tcgccatggc aacgaggtcg cacacgcccc acacccagac     300
ctccctgcga gcgggcatgg gtacaatgtc cccgttgcca cagacaccac ttcgtagcac     360
agcgcagagc gtagcgtgtt gttgctgctg acaaagaaaa atttttctta gcaaagcaaa     420
ggaggggaag cacgggcaga tagcaccgta ccatacccct tggaaactcga atgaacgaa     480 gcaggaaatg agagaatgag agttttgtag gtatatatag cggtagtgtt tgcgcgttac     540
catcatcttc tggatctatc tattgttctt ttcctcatca ctttcccctt tttcgctctt     600
cttcttgtct tttatttctt tcttttttttt aattgttccc tcgattggct atctaccaaa     660
gaatccaaac ttaatacacg tatttatttg tccaattacc                            700
```

<210> SEQ ID NO 45

```
<211> LENGTH: 699
<212> TYPE: DNA
<213> ORGANISM: Saccharomyces cerevisiae

<400> SEQUENCE: 45
tatatattaa atttgctctt gttctgtact ttcctaattc ttatgtaaaa agacaagaat      60
ttatgatact atttaataac aaaaaactac ctaagaaaag catcatgcag tcgaaattga     120
aatcgaaaag taaaactta acggaacatg tttgaaattc taagaaagca tacatcttca     180
tcccttatat atagagttat gtttgatatt agtagtcatg ttgtaatctc tggcctaagt     240
atacgtaacg aaaatggtag cacgtcgcgt ttatggcccc caggttaatg tgttctctga     300
aattcgcatc actttgagaa ataatgggaa caccttacgc gtgagctgtg cccaccgctt     360
cgcctaataa agcggtgttc tcaaaatttc tccccgtttt caggatcacg agcgccatct     420
agttctggta aaatcgcgct tacaagaaca aagaaaagaa acatcgcgta atgcaacagt     480
gagacacttg ccgtcatata taaggttttg gatcagtaac cgttatttga gcataacaca     540 ggttttaaa tatattatta tatatcatgg tatatgtgta aaatttttt gctgactggt     600 tttgtttatt tatttagctt tttaaaaatt ttactttctt cttgttaatt ttttctgatt     660
gctctatact caaaccaaca acaacttact ctacaacta                            699

<210> SEQ ID NO 46
<211> LENGTH: 95
<212> TYPE: PRT
<213> ORGANISM: Citrus jambhiri

<400> SEQUENCE: 46

Met Ser Ser Ser Ile Asn Pro Ser Thr Leu Val Thr Ser Val Asn Gly
1               5                   10                  15

Phe Lys Cys Leu Pro Leu Thr Thr Asn Lys Ala Ala Ile Arg Ile Met
            20                  25                  30

Ala Lys Asn Lys Pro Leu Gln Cys Leu Val Ser Ala Lys Tyr Asp Asn
        35                  40                  45

Leu Thr Val Asp Arg Arg Ser Ala Asn Tyr Gln Pro Ser Ile Trp Asp
    50                  55                  60

His Asp Phe Leu Gln Ser Leu Asn Ser Lys Tyr Thr Asp Glu Ala Tyr
65                  70                  75                  80

Lys Arg Arg Ala Glu Gly Leu Lys Gly Lys Val Lys Ile Ala Ile
                85                  90                  95

<210> SEQ ID NO 47
<211> LENGTH: 95
<212> TYPE: PRT
<213> ORGANISM: Olea europaea

<400> SEQUENCE: 47

Met Asp Cys Thr Met Thr Ser Ile Ser Leu Phe Ser Gln Ser Asn
1               5                   10                  15

Gly Ile Ser Gly Thr Ala Arg Ser Pro Phe Gln Trp Pro Ile Asn His
            20                  25                  30

Arg Phe Ser Ser Gly Gln Arg Asp Phe Ile Cys Lys Ser Leu Pro Val
        35                  40                  45

Ser Ser Pro Ser Ala Thr Pro Leu Ile Pro Ala Glu Asn Gly Ala Met
    50                  55                  60

Tyr Asn Tyr Ile Arg Gln Pro Val Ile Val Thr Pro Glu Val Asp Asp
65                  70                  75                  80
```

```
Gly Thr Lys His Ser Glu Leu Val Glu Arg Thr Arg Arg Glu Leu
                85                  90                  95

<210> SEQ ID NO 48
<211> LENGTH: 95
<212> TYPE: PRT
<213> ORGANISM: Perilla frutescens

<400> SEQUENCE: 48

Met Ser Ser Ile Ser Gln Lys Val Val Ile Gly Leu Asn Lys Ala Ala
1               5                   10                  15

Ala Asn Asn Leu Gln Asn Leu Asp Arg Arg Gly Phe Lys Thr Arg
                20                  25                  30

Cys Val Ser Ser Lys Ala Ala Ser Cys Leu Arg Ala Ser Cys Ser
            35                  40                  45

Leu Gln Leu Asp Val Lys Pro Val Gln Glu Gly Arg Arg Ser Gly Asn
    50                  55                  60

Tyr Gln Pro Ser Ile Trp Asp Phe Asn Tyr Val Gln Ser Leu Asn Thr
65                  70                  75                  80

Pro Tyr Lys Glu Glu Arg Tyr Leu Thr Arg His Ala Glu Leu Ile
                85                  90                  95

<210> SEQ ID NO 49
<211> LENGTH: 95
<212> TYPE: PRT
<213> ORGANISM: Phyllostachys dulcis

<400> SEQUENCE: 49

Met Ala Ser Ala Arg Ser Thr Ile Ser Leu Ser Ser Gln Ser Ser His
1               5                   10                  15

His Gly Phe Ser Lys Asn Ser Phe Pro Trp Gln Leu Arg His Ser Arg
                20                  25                  30

Phe Val Met Gly Ser Arg Ala Arg Thr Cys Ala Cys Met Ser Ser Ser
            35                  40                  45

Val Ser Leu Pro Thr Ala Thr Thr Ser Ser Ser Val Ile Thr Gly Asn
    50                  55                  60

Asp Ala Leu Leu Lys Tyr Ile Arg Gln Pro Met Val Ile Pro Leu Lys
65                  70                  75                  80

Glu Lys Glu Gly Thr Lys Arg Arg Glu Tyr Leu Leu Glu Lys Thr
                85                  90                  95

<210> SEQ ID NO 50
<211> LENGTH: 95
<212> TYPE: PRT
<213> ORGANISM: Vitis vinifera

<400> SEQUENCE: 50

Met Ser Arg Phe Val Thr Met Pro Ser His Val Leu Pro Ser Ser Phe
1               5                   10                  15

Val Ala Pro Ser Leu Gln Val Ser Ser Pro Cys Ser Trp Arg Thr
                20                  25                  30

Arg Pro Ser Pro Cys Thr Ser Cys His Leu Ser Pro Ser Ser Ser
            35                  40                  45

Lys Pro Leu Leu Gly Ser His Asp Tyr Ser Leu Leu Lys Ser Leu Thr
    50                  55                  60

Leu Ser Pro His Ala Val Asn Ser Glu Ala Asp Ser Ser Thr Arg Arg
65                  70                  75                  80

Met Lys Glu Val Lys Glu Arg Thr Trp Glu Ala Phe Tyr Arg Ala
```

-continued

```
<210> SEQ ID NO 51
<211> LENGTH: 95
<212> TYPE: PRT
<213> ORGANISM: Ocimum basilicum

<400> SEQUENCE: 51

Met Ser Cys Ala Arg Ile Thr Val Thr Leu Pro Tyr Arg Ser Ala Lys
1               5                   10                  15

Thr Ser Ile Gln Arg Gly Ile Thr His Tyr Pro Ala Leu Ile Arg Pro
            20                  25                  30

Arg Phe Ser Ala Cys Thr Pro Leu Ala Ser Ala Met Pro Leu Ser Ser
        35                  40                  45

Thr Pro Leu Ile Asn Gly Asp Asn Ser Gln Arg Lys Asn Thr Arg Gln
    50                  55                  60

His Met Glu Glu Ser Ser Ser Lys Arg Arg Glu Tyr Leu Leu Glu Glu
65                  70                  75                  80

Thr Thr Arg Lys Leu Gln Arg Asn Asp Thr Glu Ser Val Glu Lys
                85                  90                  95
```